United States Patent
Walen

(10) Patent No.: US 11,793,536 B2
(45) Date of Patent: Oct. 24, 2023

(54) SURGICAL TOOL HAVING CABLES FOR SELECTIVELY STEERING AND LOCKING A SHAFT IN A BEND

(71) Applicant: Stryker Corporation, Kalamazoo, MI (US)

(72) Inventor: James G. Walen, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 334 days.

(21) Appl. No.: 17/002,108

(22) Filed: Aug. 25, 2020

(65) Prior Publication Data

US 2020/0383697 A1 Dec. 10, 2020

Related U.S. Application Data

(63) Continuation of application No. 15/293,506, filed on Oct. 14, 2016, now Pat. No. 10,786,271, which is a
(Continued)

(51) Int. Cl.
*A61B 17/00* (2006.01)
*A61B 17/29* (2006.01)

(52) U.S. Cl.
CPC ........ *A61B 17/29* (2013.01); *A61B 17/00234* (2013.01); *A61B 2017/003* (2013.01);
(Continued)

(58) Field of Classification Search
CPC .............. A61B 17/29; A61B 17/00234; A61B 2017/003; A61B 2017/2925; A61B 2017/2929; A61B 2017/2946
See application file for complete search history.

(56) References Cited

U.S. PATENT DOCUMENTS 4,850,354 A 7/1989 Mcgurk-Burleson et al.
5,271,381 A 12/1993 Ailinger et al.
(Continued)

FOREIGN PATENT DOCUMENTS

EP 2151204 A1 2/2010
KR 2013120900 A * 11/2013 ......... A61B 1/00085
(Continued)

OTHER PUBLICATIONS

"PCT "International Search Report and Written Opinion" for PCT/US2015/026149, dated Jun. 5, 2015."

*Primary Examiner* — Gary Jackson
*Assistant Examiner* — Sebastian X Lukjan
(74) *Attorney, Agent, or Firm* — Howard & Howard Attorneys PLLC

(57) ABSTRACT

A surgical tool with cable-based steering assembly and lock assembly. An outer tube is coupled to a handle, and an inner member includes a tissue working member. The inner member may be an inner tube rotatably disposed in the outer tube and including a flexible neck aligned with links coupled to the outer tube. A steering unit is configured to be actuated to simultaneously tension and slacken steering cables to cause relative pivoting of the links so as to provide a bend or curve. The lock assembly is configured to be actuated to place simultaneous tension on the steering cables to compress the links against each other and inhibit further pivoting of the links against side loading from the tissue. The links may be shaped to have a frame that is tube-shaped with the frames of the links have the same inner and outer diameters as the outer tube.

20 Claims, 38 Drawing Sheets

Related U.S. Application Data continuation of application No. PCT/US2015/026149, filed on Apr. 16, 2015.

(60) Provisional application No. 61/992,506, filed on May 13, 2014, provisional application No. 61/980,763, filed on Apr. 17, 2014.

(52) U.S. Cl.
CPC .......... *A61B 2017/2925* (2013.01); *A61B 2017/2929* (2013.01); *A61B 2017/2946* (2013.01)

(56) References Cited

U.S. PATENT DOCUMENTS

| | | | |
|---|---|---|---|
| 5,286,253 A | 2/1994 | Fucci | |
| 5,411,514 A | 5/1995 | Fucci et al. | |
| 5,454,827 A | 10/1995 | Aust et al. | |
| 5,540,706 A | 7/1996 | Aust et al. | |
| 5,601,583 A | 2/1997 | Donahue et al. | |
| 5,618,294 A | 4/1997 | Aust et al. | |
| 5,669,926 A | 9/1997 | Aust et al. | |
| 5,741,287 A | 4/1998 | Alden et al. | |
| 5,755,731 A | 5/1998 | Grinberg | |
| 5,766,199 A | 6/1998 | Heisler et al. | |
| 5,843,106 A | 12/1998 | Heisler | |
| 5,885,288 A | 3/1999 | Aust et al. | |
| 5,899,914 A | 5/1999 | Zirps et al. | |
| 5,922,003 A | 7/1999 | Anctil et al. | |
| 5,938,678 A | 8/1999 | Zirps et al. | |
| 5,976,074 A | 11/1999 | Moriyama | |
| 6,217,598 B1 | 4/2001 | Berman et al. | |
| 6,464,711 B1 | 10/2002 | Emans et al. | |
| 6,503,263 B2 | 1/2003 | Adams | |
| RE38,018 E | 3/2003 | Anctil et al. | |
| 6,533,749 B1 | 3/2003 | Mitusina et al. | |
| 6,620,180 B1 | 9/2003 | Bays et al. | |
| 6,656,195 B2 | 12/2003 | Peters et al. | |
| 6,958,071 B2 | 10/2005 | Carusillo et al. | |
| 7,179,223 B2 | 2/2007 | Motoki et al. | |
| 7,250,027 B2 | 7/2007 | Barry | |
| 7,338,495 B2 | 3/2008 | Adams | |
| 7,699,846 B2 | 4/2010 | Ryan | |
| 7,854,736 B2 | 12/2010 | Ryan | |
| 7,927,361 B2 | 4/2011 | Oliver et al. | |
| 8,052,706 B2 | 11/2011 | Mitusina | |
| 8,109,956 B2 | 2/2012 | Shadeck | |
| 8,202,288 B2 | 6/2012 | Adams et al. | |
| 8,277,474 B2 | 10/2012 | Norman et al. | |
| 8,287,469 B2 | 10/2012 | Stefanchik et al. | |
| 8,292,803 B2 | 10/2012 | Watanabe | |
| 8,336,754 B2 | 12/2012 | Cappola et al. | |
| 8,388,520 B2 | 3/2013 | Stefanchik et al. | |
| 8,403,926 B2 | 3/2013 | Nobis et al. | |
| 8,409,235 B2 | 4/2013 | Rubin | |
| 8,419,768 B2 | 4/2013 | Marczyk | |
| 8,435,259 B2 | 5/2013 | Dierck | |
| 8,496,152 B2 | 7/2013 | Viola | |
| 8,623,266 B2 | 1/2014 | Adams | |
| 8,758,379 B2 | 6/2014 | Rubin | |
| 8,801,752 B2 | 8/2014 | Fortier et al. | |
| 8,870,867 B2 | 10/2014 | Walberg et al. | |
| 8,906,053 B2 | 12/2014 | Oliver et al. | |
| 8,968,355 B2 | 3/2015 | Malkowski et al. | |
| 9,089,344 B2 | 7/2015 | Rubin | |
| 9,198,685 B2 | 12/2015 | Edwards et al. | |
| 9,308,013 B2 | 4/2016 | Casey et al. | |
| 9,381,032 B2 | 7/2016 | Edwards et al. | |
| 9,402,645 B2 | 8/2016 | Norman et al. | |
| 9,687,254 B2 | 6/2017 | Shadeck et al. | |
| 10,022,144 B2 | 7/2018 | Nguyen et al. | |
| 10,166,013 B2 | 1/2019 | Nguyen et al. | |
| 10,206,706 B2 | 2/2019 | Nguyen | |
| 10,321,929 B2 | 6/2019 | Willhite et al. | |
| 2003/0036748 A1 | 2/2003 | Cooper et al. | |
| 2003/0125716 A1 | 7/2003 | Wang et al. | |
| 2004/0054322 A1 | 3/2004 | Vargas | |
| 2004/0243163 A1 | 12/2004 | Casiano et al. | |
| 2005/0090849 A1 | 4/2005 | Adams | |
| 2005/0277970 A1* | 12/2005 | Norman | A61B 17/32002 606/180 |
| 2006/0058582 A1 | 3/2006 | Maahs et al. | |
| 2007/0250113 A1 | 10/2007 | Hegeman et al. | |
| 2008/0208194 A1 | 8/2008 | Bickenbach | |
| 2009/0227842 A1 | 9/2009 | Ando | |
| 2010/0030018 A1* | 2/2010 | Fortier | A61B 18/1445 600/104 |
| 2010/0041945 A1 | 2/2010 | Isbell, Jr. | |
| 2010/0131005 A1* | 5/2010 | Conlon | F16C 1/101 606/167 |
| 2011/0230875 A1 | 9/2011 | Walberg et al. | |
| 2012/0010629 A1 | 1/2012 | Mire et al. | |
| 2012/0109186 A1 | 5/2012 | Parrott et al. | |
| 2012/0286019 A1 | 11/2012 | Hueil et al. | |
| 2012/0289946 A1* | 11/2012 | Steger | A61B 34/30 606/1 |
| 2012/0323077 A1 | 12/2012 | Verbeek | |
| 2013/0023882 A1 | 1/2013 | Fabro et al. | |
| 2013/0023915 A1 | 1/2013 | Mueller | |
| 2013/0102846 A1 | 4/2013 | Sjostrom et al. | |
| 2013/0144274 A1 | 6/2013 | Stefanchik et al. | |
| 2013/0150831 A1 | 6/2013 | Griffiths | |
| 2013/0197490 A1 | 8/2013 | Stanton et al. | |
| 2014/0114300 A1 | 4/2014 | Orczy-Timko et al. | |
| 2014/0288560 A1 | 9/2014 | Rubin | |
| 2016/0174999 A1 | 6/2016 | Casey et al. | |
| 2017/0027597 A1 | 2/2017 | Walen | |
| 2019/0133632 A1 | 5/2019 | Nguyen | |
| 2019/0175162 A1 | 6/2019 | Nguyen et al. | |
| 2019/0216473 A1 | 7/2019 | Edwards | |
| 2019/0298403 A1 | 10/2019 | Willhite et al. | |

FOREIGN PATENT DOCUMENTS

| | | |
|---|---|---|
| WO | 2003001986 A2 | 1/2003 |
| WO | 2012058213 A2 | 5/2012 |

\* cited by examiner

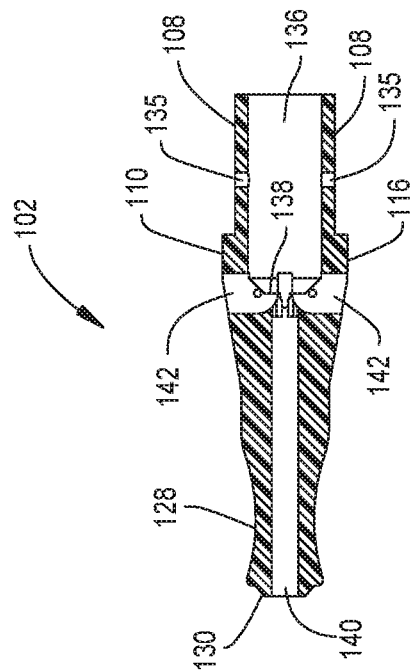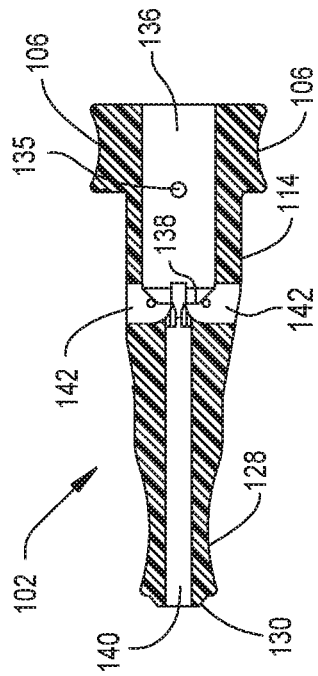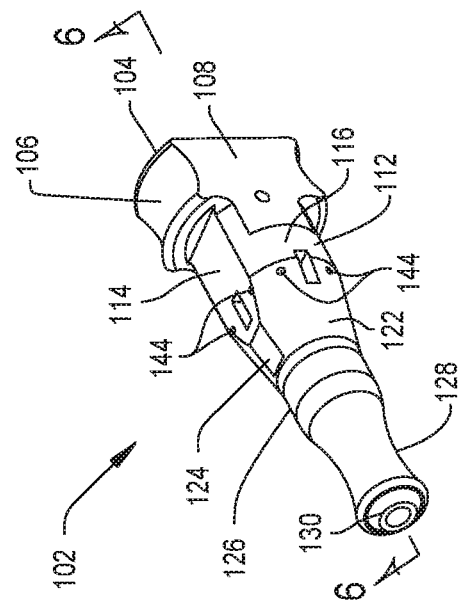

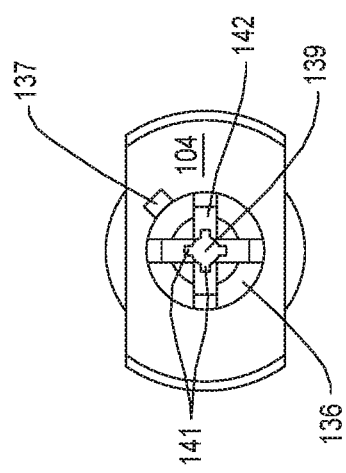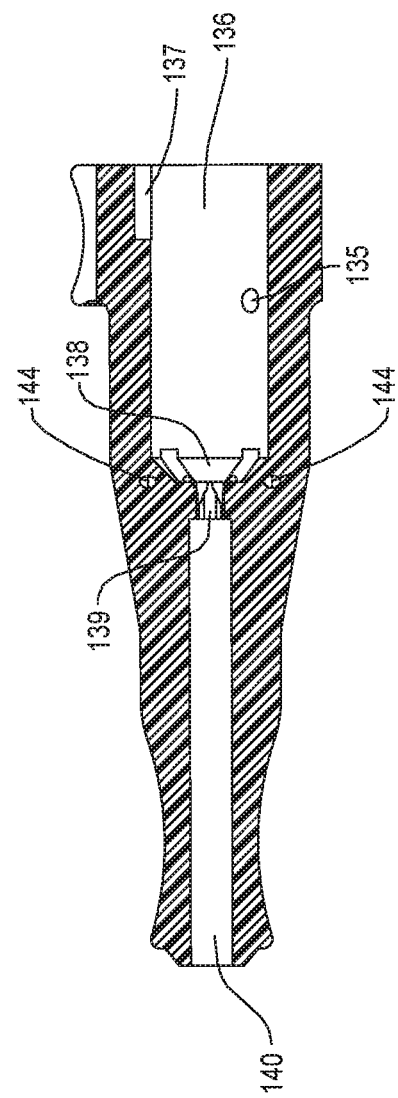

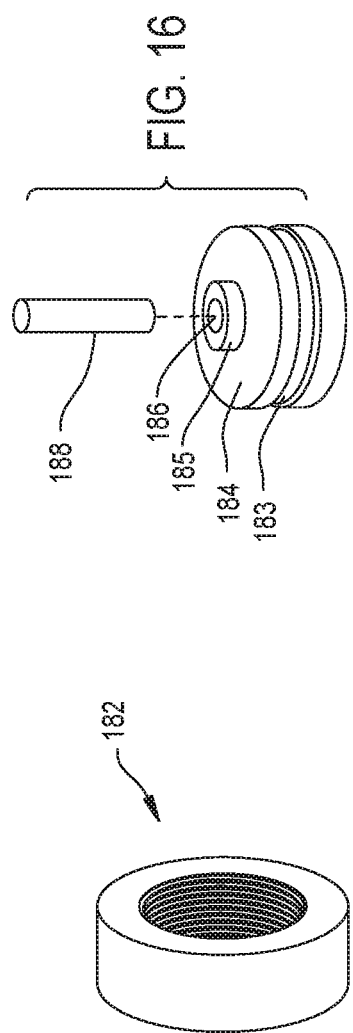
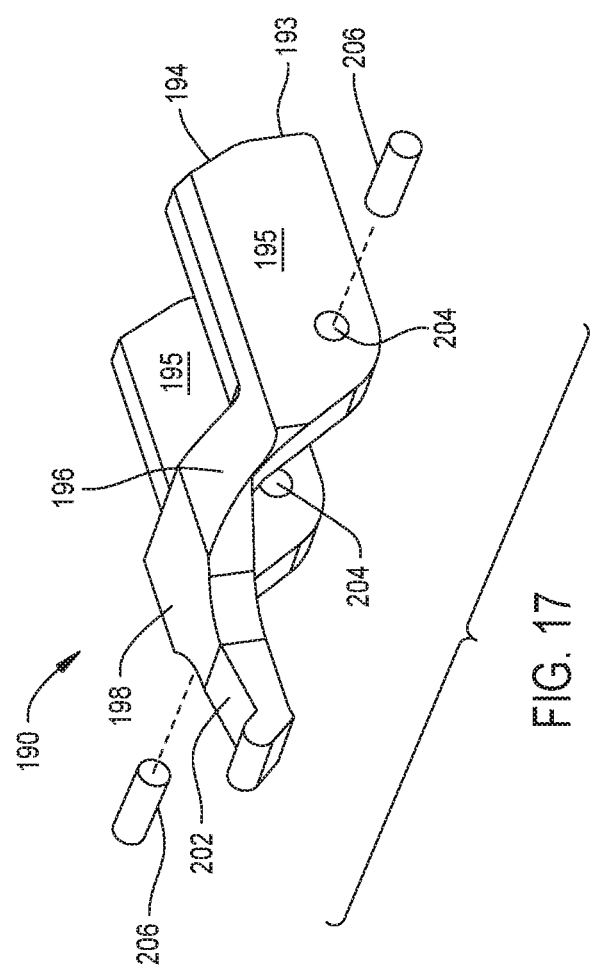

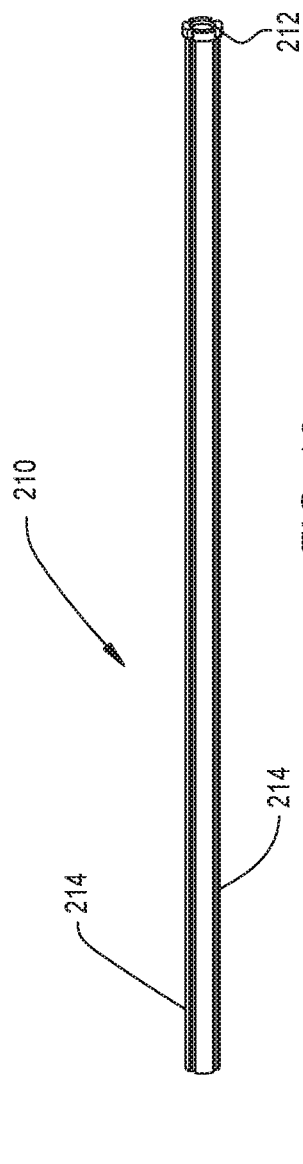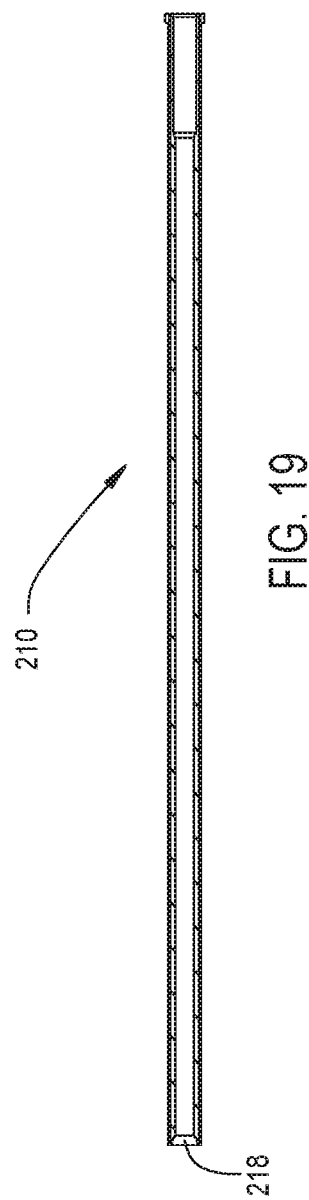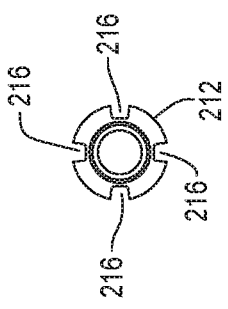

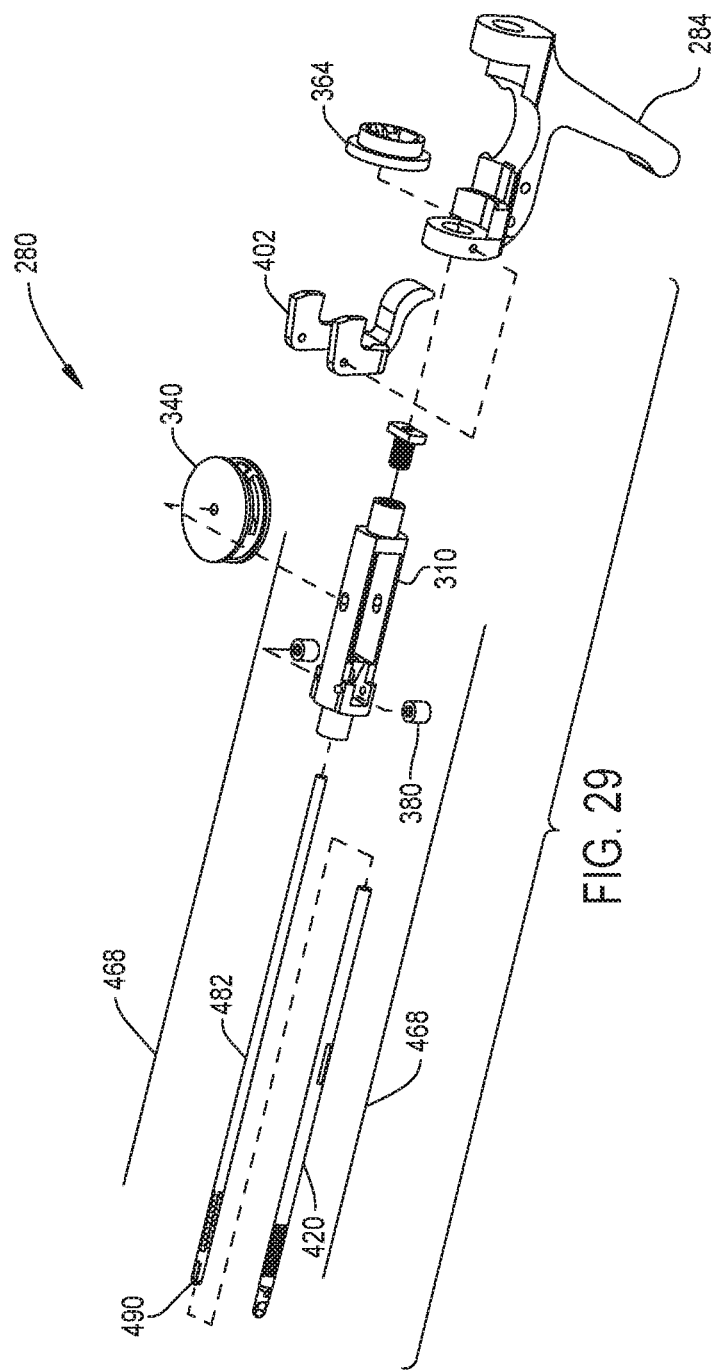

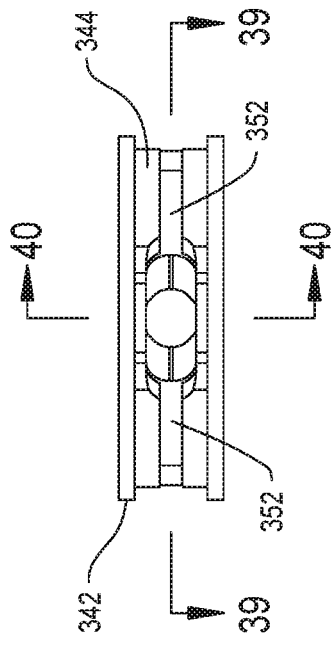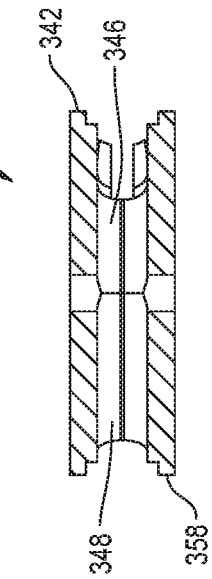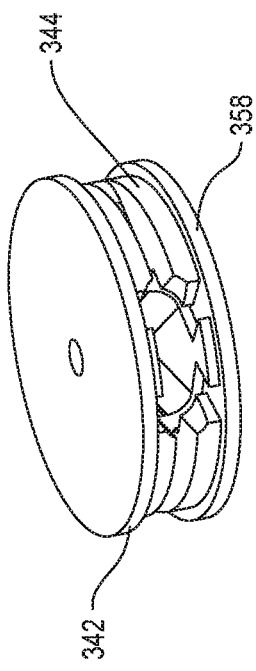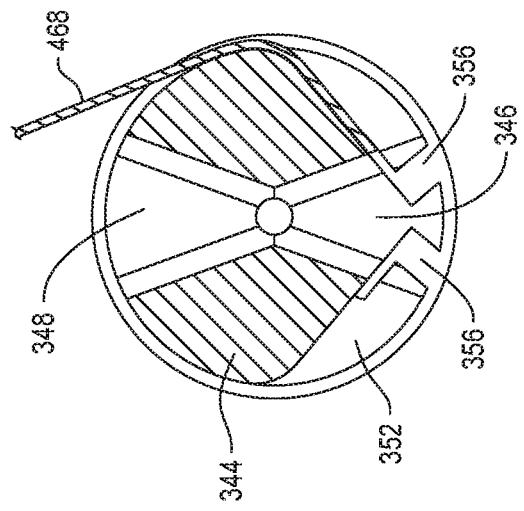

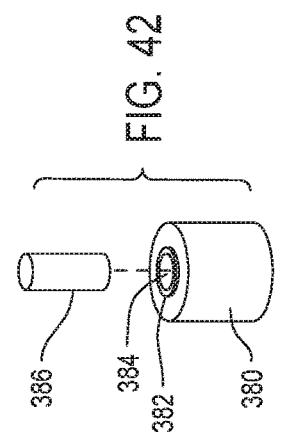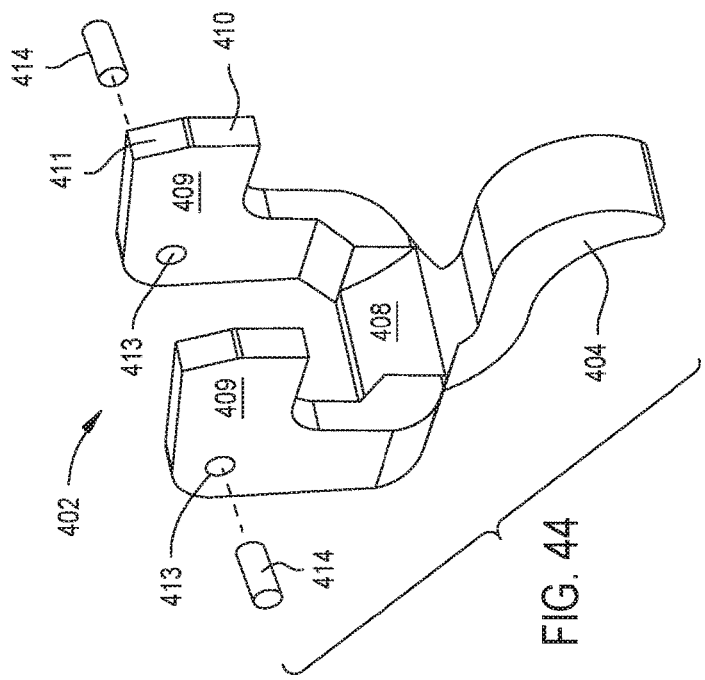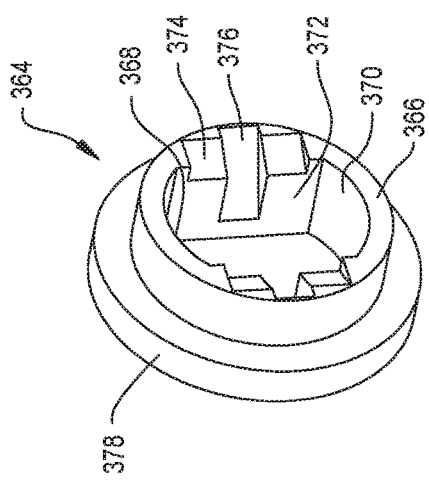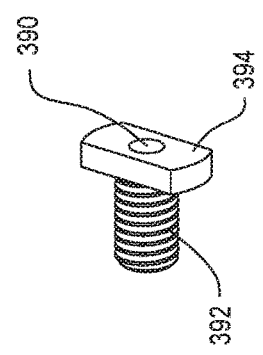

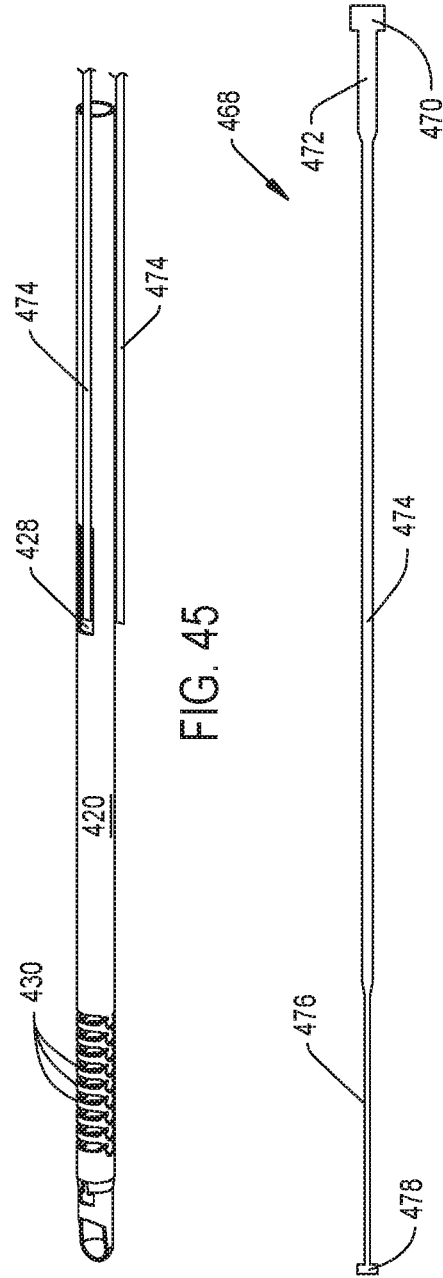

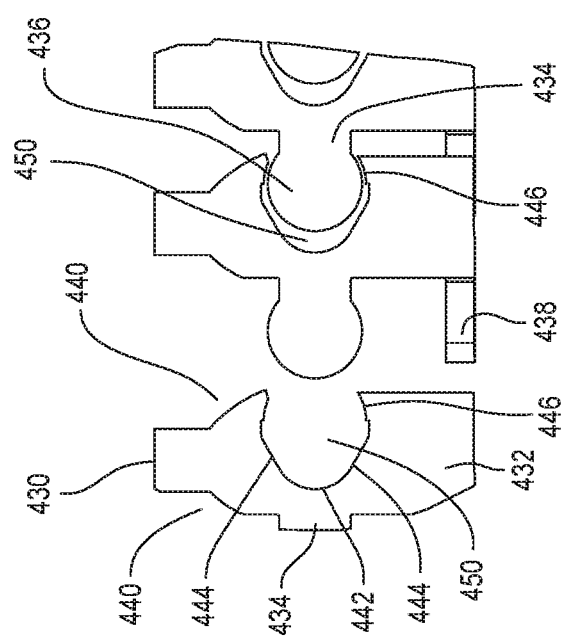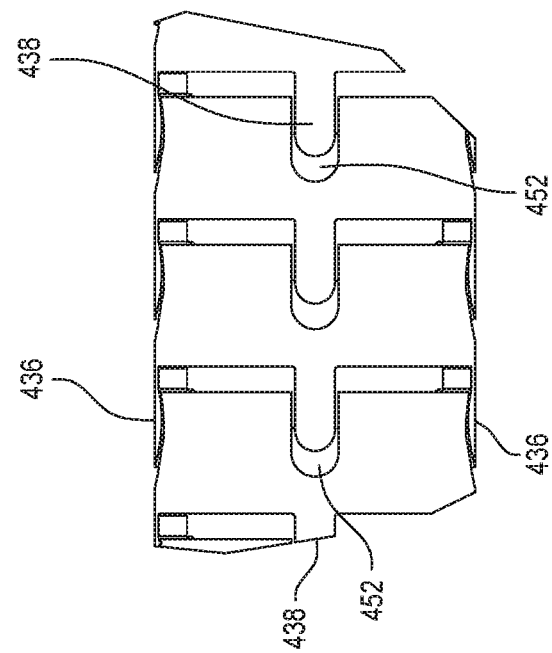

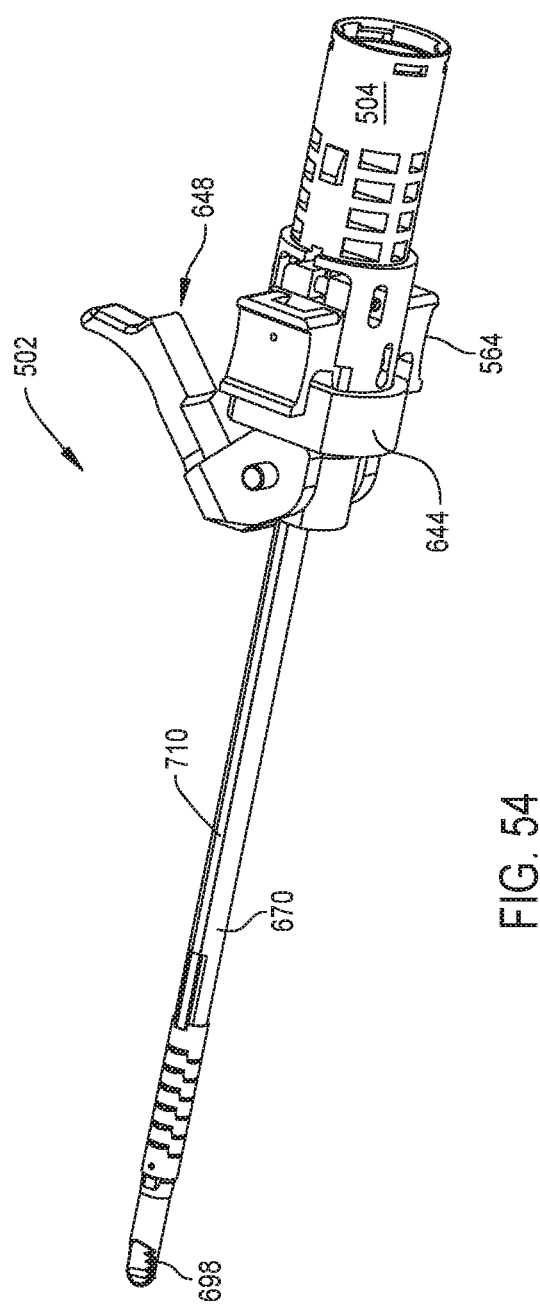
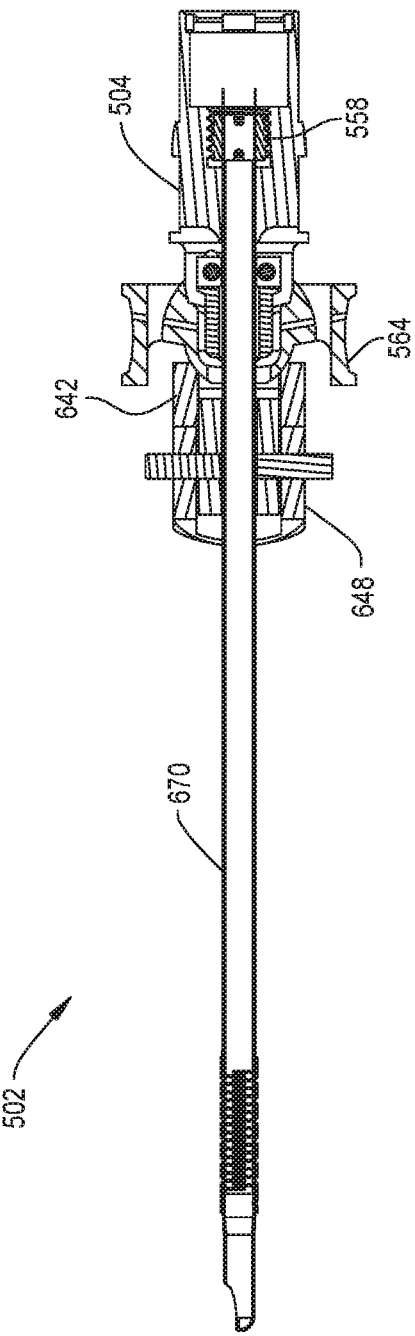

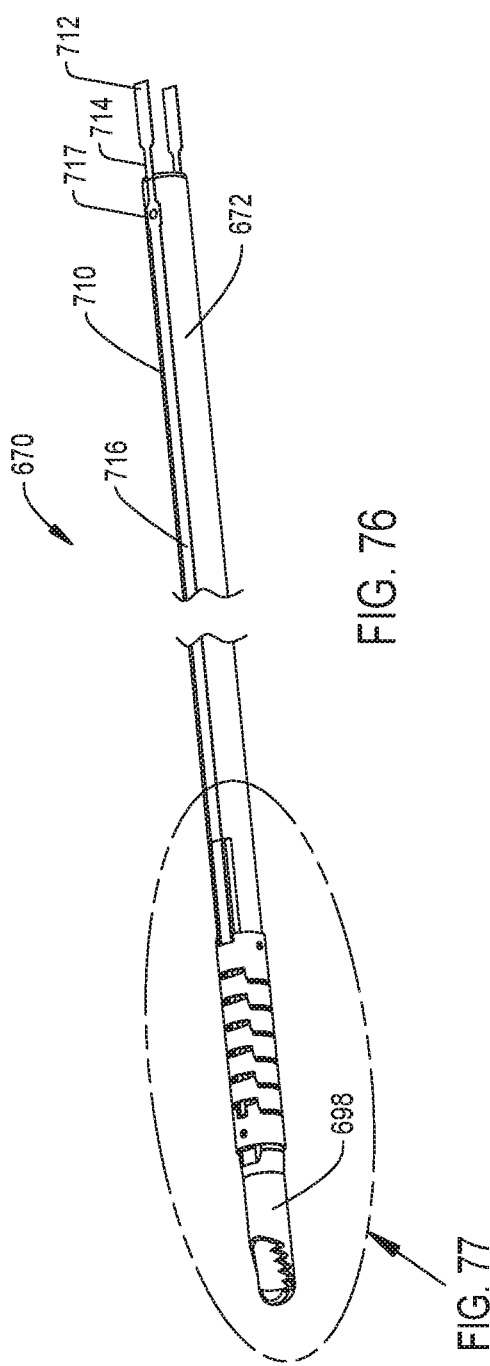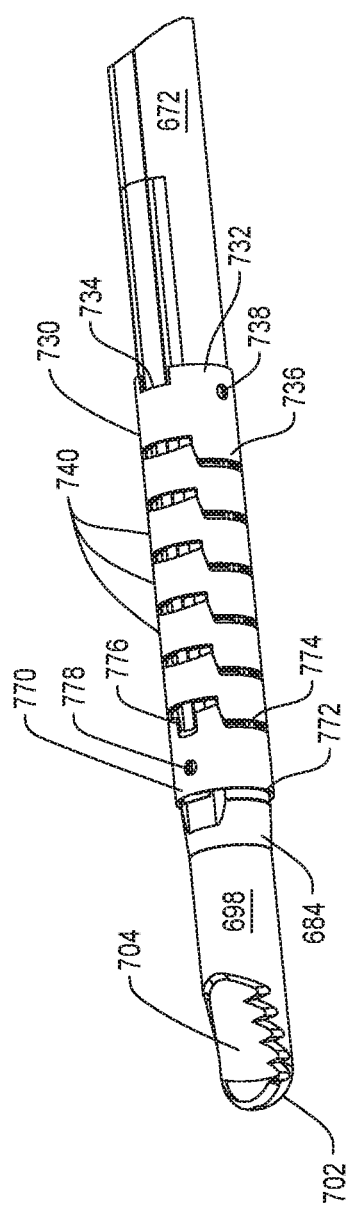
FIG. 76
FIG. 77

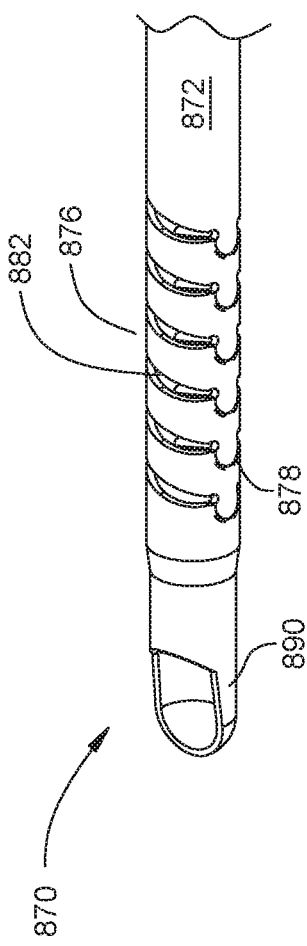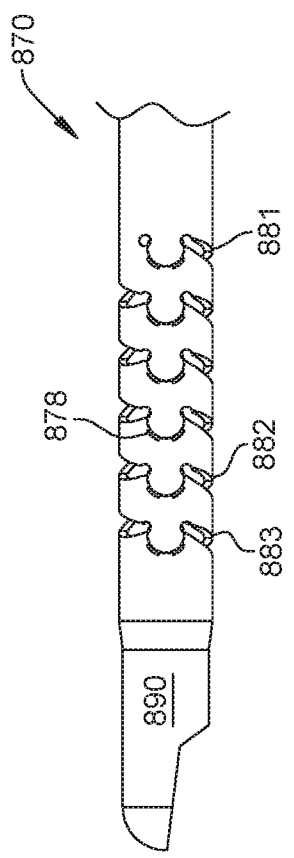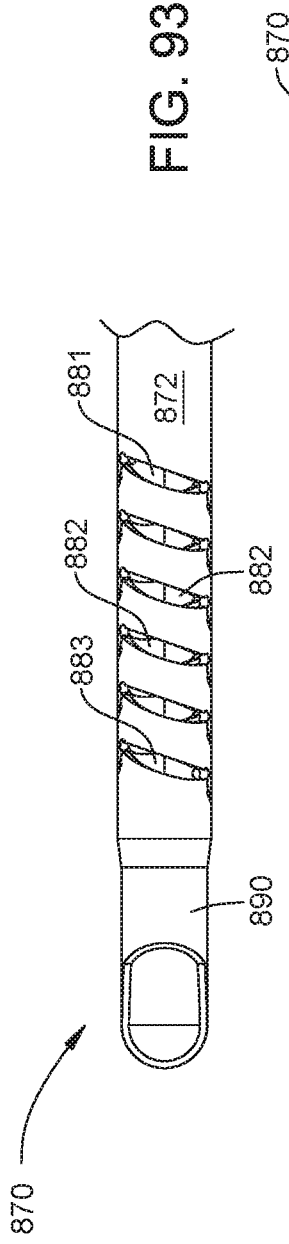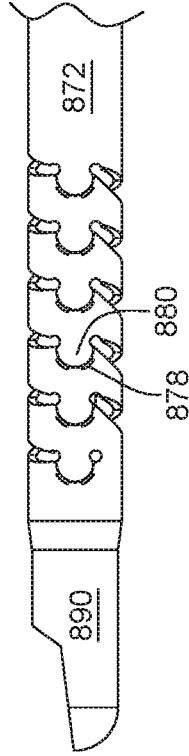

SURGICAL TOOL HAVING CABLES FOR SELECTIVELY STEERING AND LOCKING A SHAFT IN A BEND

PRIORITY CLAIM

This is a continuation of co-pending U.S. application Ser. No. 15/293,506, filed Oct. 14, 2016, which is a continuation of International Application No. PCT/US2015/026149, filed Apr. 16, 2015, which claims priority and all the benefits of U.S. Provisional Patent Application No. 61/992,506, filed May 13, 2014, and U.S. Provisional Patent Application No. 61/980,763, filed Apr. 17, 2014. The entire contents of each of the above applications are hereby incorporated by reference.

FIELD OF THE INVENTION

This invention is generally related to a medical or surgical tool that has elongated shaft that can be bent so as to have a specific curvature. More particularly, this invention is directed to a tool with an elongated shaft that can be bent and that, when exposed to a load, resists buckling.

BACKGROUND OF THE INVENTION

A number of different medical and surgical tools include elongated shafts. A device for performing a medical or surgical procedure or a diagnostic evaluation is located at the distal end of the shaft, the end spaced from the practitioner using the tool. Providing the tool with shaft makes it possible to position the device that performs the procedure in the patient at location that is 5 cm or more below the skin. The presence of the shaft makes it possible to perform a procedure on the patient without having to make a large incision so that the location at which the procedure is performed is essentially exposed to the ambient environment. Exemplary surgical tools with this type of shaft include burs, shavers, forceps, staplers, ultrasonic vibrators, RF tissue ablation and/or cauterization electrodes and cameras used to view inside the patient.

When this type of tool is used, the tool is often directed to the site at which the procedure is to be formed through a portal or channel in the patient. This portal may be one that is established as part of the procedure. Alternatively, the portal may be part of channel that natural exists in the patient. Nostrils are an example of one set of naturally present portals in a patient It is a known practice to provide this type of tool with a shaft that, once inserted in the patient is selectively curved. This is because there are many situations in which it is simply not desirable or even possible to perform the procedure by simply positioning the distal end of the shaft at the site at which the procedure is performed. For example, in some procedures the portal itself curves. This means that after at least partially inserting the shaft in the portal, the practitioner needs to bend the tool shaft so as to further insert the shaft. In some procedures the practitioner may want to curve the distal end of the shaft to obtain a minimally obstructed view of the application of the working component to the site to which the component is applied.

One species of a tool with a selectively curved shaft is provided with multiple adjacent segments that each bendable relative to each other. At least one cable extends through the shaft to a distally located segment. Some tools are provided with two, three or four cables. The cables are connected to an anchor adjacent the proximal end of the shaft, the end opposite the distal end. The anchor typically is able to rotate around at least one axis. A number of these tools are further designed so that the position of the anchor is manually set. The practitioner bends the tool by rotating the anchor to cause the selective tensioning and flexing of the cables. This flexing and tensioning of the cables places a longitudinal load on the shaft from the distal end of the shaft. This load is not uniformly imposed on the shaft. There is an arcuate section of the shaft that is subjected to greater loading. The portions of the segments forming this part of the shaft so loaded are compressed or bent towards each other. The bending of these segments is what provides the shaft with its practitioner selected curve.

It is further feature to provide this type of tool with a mechanism to lock the anchor in place. This lock is set once the anchor is positioned so the shaft has a bend with the desired curvature. The rational for locking the position of the anchor is that, by extension, the positions of the cables are set. The locking of the cables is ideally intended to hold the shaft in the bent position desired by the practitioner.

In practice, even with cables firmly locked in position, the segments of the tool shaft may still flex relative to each other. This is because if the segments are subjected to loading, especially side loading, the cables, though fixed in length relative a static location along the tool may not appreciably oppose this side loading. If this event occurs, the tool develops a bend that deviates from the practitioner desired bend. Should this happen in the procedure the practitioner may have to interrupt the use of the tool to reposition tool to ensure that the distal end components are properly positioned. If this flexure from the desired bend is significant, the time it takes to have to reposition and rebend the tool can start to add to the overall time it takes to perform the procedure.

What makes this inability of a tool to buckle under side loading especially disadvantageous is that in order to use this type it is often necessary to press the tool against tissue. This exposes the tool to the side loading that, as discussed above, has a tendency to distort the practitioner desired bend.

SUMMARY OF THE INVENTION

This invention is directed to a new and useful surgical tool with an elongated shaft that is selectively bendable. The surgical tool of this invention is further designed so that, once the shaft is bent to the desired shape, the tool is set to resist the loading that may cause the shaft to flex from the practitioner set shape.

The tool of this invention includes an elongated shaft. At the proximal, end the shaft is connected to a handle or a handpiece. At the distal end of the shaft there is at least one if not multiple links. Each link is able to pivot relative to at least one adjacent portion of the shaft. At least two cables or reins extend from the handle towards the distal end of the shaft. The cables are connected to the most distally located link. At the handle end, the cables are attached to steering unit. The steering unit is actuated to set the extent to which the cables extend forward from the handle.

The tool of this invention is further designed so the steering unit moves longitudinally relative to the handle. An actuator mounted to the handle controls the positioning of the steering assembly along the handle. In some versions of the invention, the actuator is a manually set lever.

A tool of this invention is used by directing the distal end of the shaft to the site to which the tool is to be applied. The shaft is bent to the desired shape by using the steering assembly to set the lengths of the cables. The setting of the lengths of the cables places an asymmetric load on the links. This causes each link to selectively pivot relative to the adjacent component of the tool. As a result of the pivoting of the links, the shaft develops a bend with a curvature desired by the practitioner.

Once the shaft is bent so as to have the shape, the curvature, desired by the practitioner, the actuator is employed to move the steering assembly proximally away from the handle. This shift in the position of the steering assembly causes the cables to go into tension between the steering assembly and the distally located component to which the cables are connected. The tensioning of the cables causes the pivoted links to compress against each other.

The compression of the links against each other holds the links in fixed orientations relative to each other. Thus, when exposed to a load, the links resist movement relative to each other. This means that when exposed to a load or force, the tool of this invention maintains the curved shaped desired by the practitioner.

In some versions of the invention, the shaft and links are separate components. The individual links may also be separate from each other. In other versions of the invention, the shaft and links are a single piece component that is shaped to form these individual features. Alternatively, the shaft and links are separate from each and the link are formed as a single-piece unit.

While this invention is primarily designed as a surgical tool, the invention may have applications outside of the field of medicine and surgery.

BRIEF DESCRIPTION OF THE DRAWINGS

The invention is pointed out with particularity in the claims. The above and further features of this invention may be better understood by reference to the following description taken in conjunction with the accompanying drawings in which:

FIG. 5 is a perspective view of the handle or body of the tool of FIG. 1;

FIG. 6 is a cross sectional view of the tool handle of FIG. 4 taken along line 6-6;

FIG. 7 is a cross-sectional view of the tool handle taken along a plane perpendicular to the plane of the view of FIG. 6;

FIG. 8 is a cross-sectional view of the tool handle taken along a plane between the planes of FIGS. 6 and 7;

FIG. 9 is a plan view looking distally of the proximal end of the tool handle;

FIG. 15 is a perspective view of the lock collar;

FIG. 16 is an exploded view of one of the rollers internal to the handle and the pin to which the roller is mounted;

FIG. 17 is a perspective view of the lock lever and the pins that hold the lever to the handle;

FIG. 18 is a perspective view of the tool shaft;

FIG. 19 is a cross sectional view of the tool shaft;

FIG. 20 is a plan view of the proximal end of the tool shaft;

FIG. 29 is an exploded view of the first alternative surgical tool;

FIG. 37 is a second perspective view of the steering wheel;

FIG. 38 is a plan view of the proximally directed surfaces of the steering wheel;

FIG. 39 is a cross sectional view of the steering wheel taken along line 39-39 of FIG. 38 and of a steering rein mounted to the wheel;

FIG. 40 is a cross sectional view of the steering wheel taken along line 40-40 of FIG. 38;

FIG. 41 is a perspective view of the lock ring of the first alternative surgical tool;

FIG. 42 is an exploded view of one of the rollers internal to the first alternative surgical tool and of the pin that holds the roller to the tool handpiece;

FIG. 43 is a perspective view of the set screw of the first alternative surgical tool;

FIG. 44 is an exploded view of the lock lever of the first alternative surgical tool and the pins that hold the lever to the tool handle;

FIG. 45 is a perspective view of the outer bendable tube of the first alternative surgical tool and the reins that bend the tube;

FIG. 50 is a partially exploded view of the sides of adjacent links integral with shaft of FIG. 45;

FIG. 51 is a view of the rear facing surfaces of the links of FIG. 45;

FIG. 52 is a plan view of a steering rein;

FIG. 54 is a perspective view of a second alternative surgical tool of this invention;

FIG. 55 is a cross sectional view of the tool of FIG. 54;

FIG. 76 is a perspective view of the outer tube of the tool of FIG. 54 and the reins mounted to the tube;

FIG. 77 is an enlarged view of the distal end of the outer shaft seen in FIG. 76;

FIG. 91 is a perspective view of another alternative shaft or outer tube of this invention;

FIG. 92 is a first side plan view of the alternative tube of FIG. 91;

FIG. 93 is a top plan view of the alternative tube of FIGS. 91; and

FIG. 94 is a second side plan view of the alternative tube of FIG. 91.

DETAILED DESCRIPTION

I. First Embodiment

Figure 1:
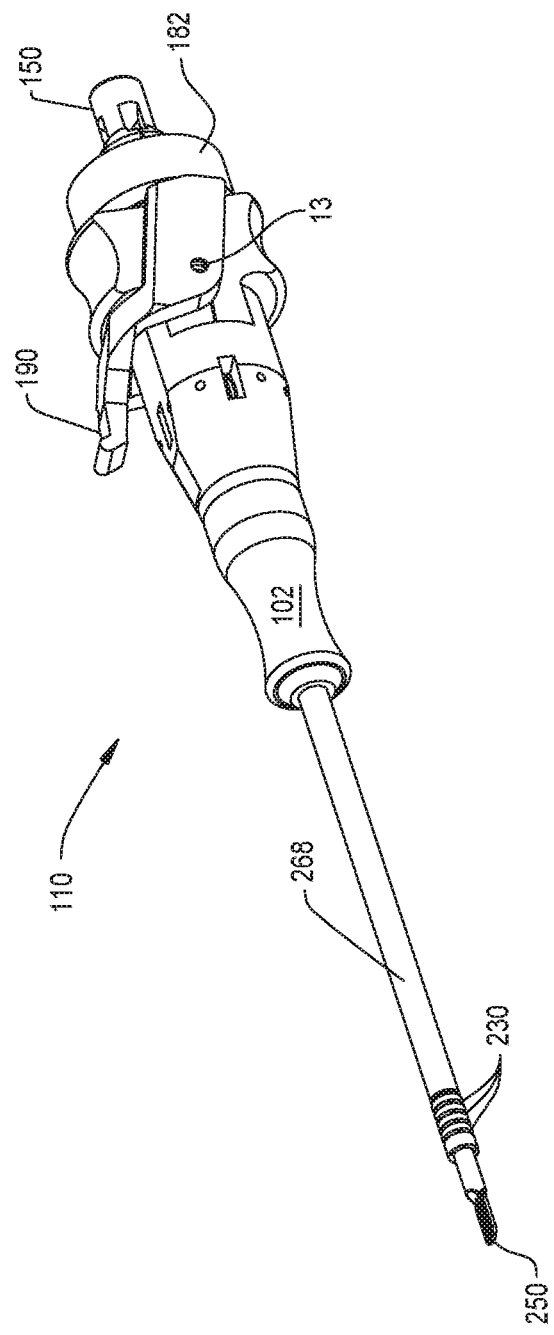
FIG. 1 is a perspective view of a surgical tool constructed in accordance with this invention.
Figure 2:
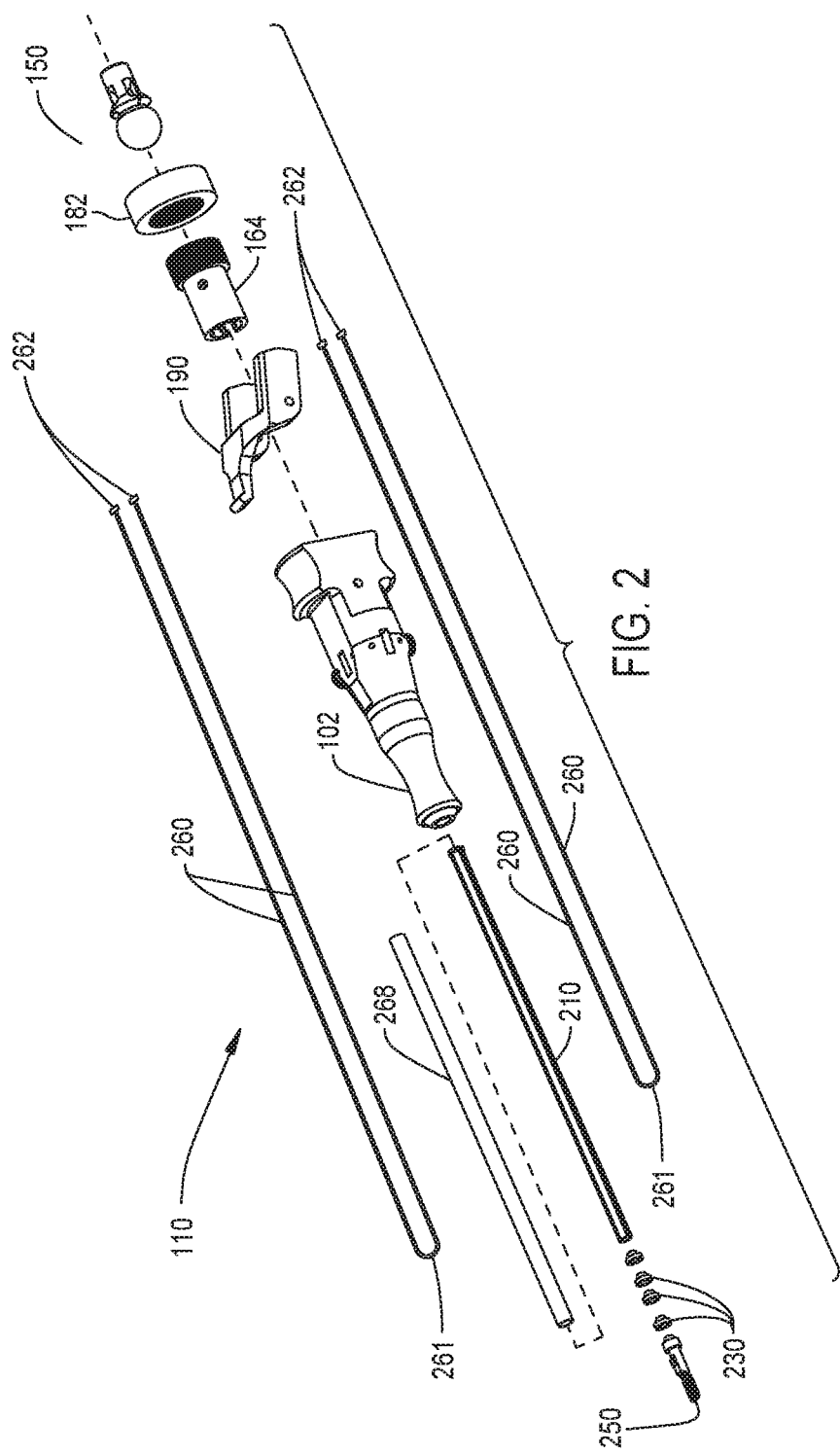
FIG. 2 is an exploded view of the surgical tool of FIG. 1.
Figure 3:
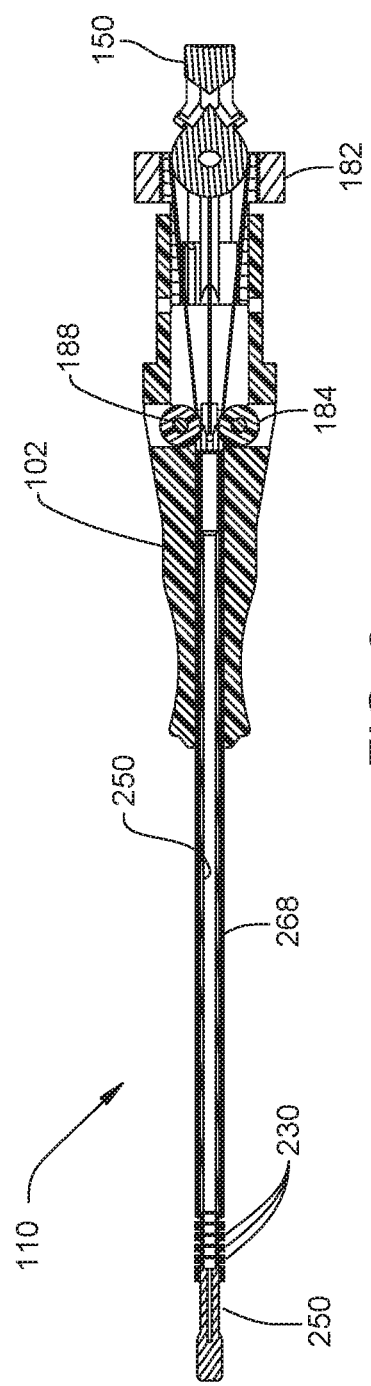
FIG. 3 is a cross sectional view of the surgical tool of FIG. 1.

One version of a surgical tool 110 of this invention is now generally described by reference to FIGS. 1-4 includes a handle 102. A shaft 210 extends distally forward from the handle 102. ("Distal" is understood to mean away from the practitioner holding the tool, towards the site to which the tool is applied. "Proximal" is understood to mean towards the practitioner, away from the site to which the tool is applied.) A tissue working member 250 is located forward of the distal end of the shaft 210. A set of links 230 connects the tissue working member 250 to the shaft 210. Each link 230 is able to pivot relative to the adjacent link. The pivoting of the links 230 is controlled by the selective tensioning of steering cables 260 that extend to the links. The proximal end of the cables 260 are connected to a steering arm 150 that is pivotally and slidably mounted to the handle 102. The pivotal movement of the steering arm 150 controls the tensioning of the cables so to selectively pivot the links 230.

A lock lever 190 is pivotally attached to the handle 102. The setting of the lock lever 190 sets the position of the steering arm 150 relative to the handle 102. Specifically, the lock lever 190 is set between a bending enabled position and a locked position. When lock lever 190 is in the bending enabled position, it is possible to flex the cables 260 so the set of links 230 form a practitioner selective bent assembly. When the lock lever 190 is in the locked position, links 230 are pressed together so as resist being flexed out of the practitioner selected bent shape.

The tool handle 102, now described by reference to FIGS. 5-9, is formed from a plastic such as a PEEK plastic. The handle 102 is shaped to have a head 104 that forms the most proximal portion of the handle. The head 104 is formed have two curve surfaces 106 that are diametrically opposed to each other relative to the proximal-to-distal longitudinal axis through the handle 102. Curved surfaces 106 are further formed so that, longitudinally along the handle, the surfaces are concave. Head 104 is further formed to have two diametrically opposed parallel flat surfaces 108. Each flat surface 108 connects one end of a curved surface 106 the adjacent end of the other curved surface 106. Distally forward of the head 104, handle 102 has a neck 112. Neck 112 is formed to have two diametrically opposed flat surfaces 114 and two diametrically opposed curved surfaces 116. The handle 102 is formed so that each neck flat surface 114 extends forward from a location adjacent one of the head curved surfaces 106. The neck flat surfaces 114 are thus perpendicular to head flat surfaces 108. The neck flat surfaces 114 are spaced apart from each other so as to be within the circle defined by the head curved surfaces 106. Neck curved surfaces 116 extend radially outwardly from head flat surfaces 108. The handle 102 is further formed so that each head flat surface 108 extends distally forward so as to and partially through the neck 112 so as to interrupt the adjacent neck curved surface 116.

Forward of the neck 112, handle 102 has a torso 122. The torso 122 is generally frusto-conical in shape. Extending distally from the neck curved surfaces 116, the diameter of the torso 122 decreases. While the torso 122 is generally conic neck flat surfaces 114 extend over the adjacent portions of the torso 122 to interrupt the curve of the torso. Forward of each neck flat surface 114 there is a small addition flat 124 (one flat 124 identified in FIG. 5). As each flat 124 extends distally, the flat angles towards the longitudinal axis of the handle 102.

Distal to the torso 122, the handle 102 has a waist 126. Not identified is the transition region between the torso 122 and the waist 126. Waist 126 is circular in cross section and of constant diameter in length. A leg 128 extends forward from waist 126. In cross section, leg 128 is circular in shape. The diameter of the leg is not constant along the length of the leg. Specifically, the leg 128 is shaped so that extending longitudinally along the outer surface of the leg the leg has a concave profile. The handle 102 is dimensioned so that the leg, at least at is smallest diameter portion can be held between two fingers. A small foot 130 forms the most distal portion of the tool handle 102. Foot 130 is approximately in shape of slice section of a sphere. The handle is shaped so that in planes perpendicular to the longitudinal axis, the largest diameter portion of foot 130 is adjacent the leg 128. The smallest diameter portion of the foot 130 is spaced from the leg.

The tool handle 102 is formed with a number of bores. A proximal bore 136 extends distally from the proximal face of the handle head 104. Bore 136 extends through the head 104 and most of the adjacent portion of neck 112. The bore 136 is of constant diameter. The proximal end of the handle 102 is formed with a notch 137 that extends radially outwardly from proximal bore 136. Notch 137 extends distally from the proximal open end of bore 136. The notch 137 does not extend the whole length of bore 137. Instead the notch 137 terminates in a section of the bore proximal to the distal end of handle head 104.

First and second torso bores 138 and 139, respectively, extend distally forward of proximal bore 136. Both torso bores 138 and 139 are disposed with the handle torso 122. First torso bore 138 extends forward from the distal end of proximal bore 136. Extending distally from the proximal bore 136, the diameter of the first torso bore 138 decreases. Second torso bore 139 extends is contiguous with and extends forward from the first torso bore 138. The handle 102 is formed so that second torso bore 139 is constant along the length of the bore 139. A distal bore, bore 140, extends forward from second torso bore 139. Distal bore 140 has a diameter larger than the diameter of the second torso bore 139. The distal bore 140 extends through the handle torso 122, waist 126, leg 128 and foot 130. Distal bore 140 has a constant diameter and this diameter is less than the diameter of the adjacent distal end of the middle bore. The handle is further formed so that four equiangularly spaced apart grooves 141, seen best in FIG. 9, extend radially outwardly from the second torso bore 139. Each groove extends from the first torso bore 138 to distal bore 140.

The handle 102 has two coaxial bores 135. Each bore 135 extends inwardly from a portion of flat surface 108 within the distal section of the neck 112. Each bore 135 opens into proximal bore 136.

Handle 102 is further formed to have four equiangularly spaced apart rectangularly shaped bores 142. Each bore 142 extends inwardly from the outer surface of the torso 122 and the adjacent portion of the handle neck 112. The major axes of the bores 142 are parallel with the longitudinal axis through the handle 102. Two of the bores 142 extend inwardly from the opposed flat surfaces 114. The remaining two bores extend inwardly from the curved surfaces of the handle 102. Each bore 142 opens into and partially overlaps the first and second torso bores 138 and 139, respectively. The plane through the center of each bore 142 that extends from the longitudinal axis of the handle is also the plane around which a separate one of the grooves 141 is centered. Each bore 142 is wider than the associated groove 141. Thus, each groove 141 can be considered to extend forward from the associated bore 142.

The handle 102 is further formed so a bore 144 is perpendicular to and intersects each bore 142. Bores 144 are circular in cross section. Two bores 144 each between the flat surfaces 114. Each of these bores 144 intersects a separate one of the bores 142 that projects inwardly from the curved surface of the torso 122. The remaining two bores 144 each extend between opposed curved faces of the torso 122. Each of these bores 144 intersects a separate one of the bores 142 that extends inwardly from the flat surfaces 114.

Figure 11:
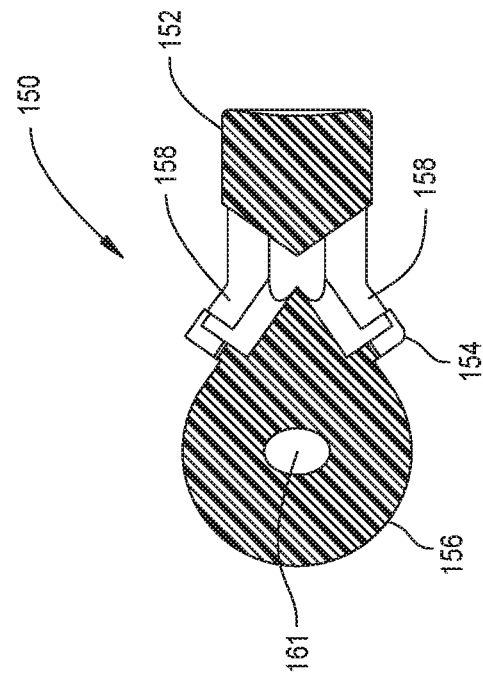
FIG. 11 is a cross sectional view of the steering arm.
Figure 10:
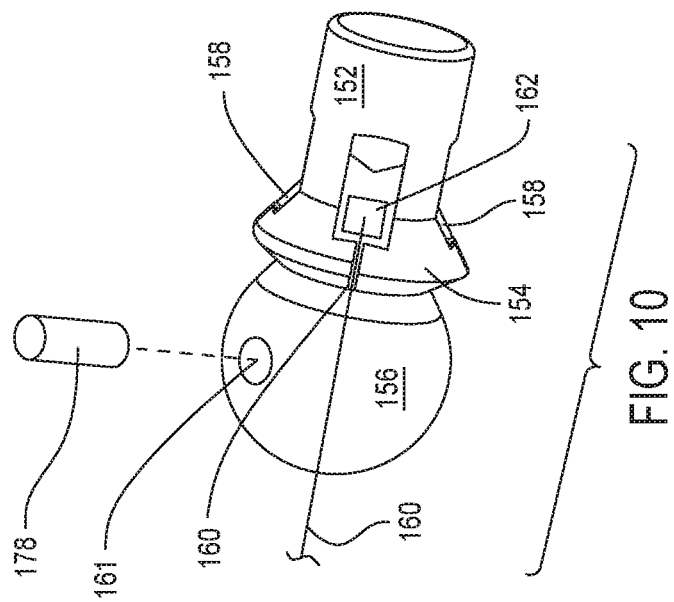
FIG. 10 is an exploded view of some of the components forming the steering assembly.

As seen in FIGS. 10 and 11, the steering arm 150 includes a generally cylindrical stem 152 that forms the most proximal end of the arm. Stem 152 extends to a ball 156 that forms the most distal portion of the arm 150. A ring 154 integrally formed with the stem 152 protrudes outwardly and circumferentially around the section of the stem adjacent the ball 156. In cross section in a plane along which the longitudinal axis of the arm extends, ring 154 has a triangular shape wherein the apex of the ring is spaced furthest from the outer surface of the stem.

Steering arm 150 is formed to have four equiangularly spaced apart recesses 158, two identified in FIG. 11. Each recess 158 extends inwardly from the distal portion of the stem 152 and the adjacent portion of the ring 154 proximal to the apex of the ring. Each recess 158 appears from the outside to be rectangularly shaped. For reasons of manufacture, the recesses 158 may meet within the stem 152. A slot 160, one identified in FIG. 10, extends distally forward from the distal end of each recess 158. Each slot 160 extends longitudinally through the ring 154. A bore 161 extends inwardly from the outer surface of ball 156.

Figure 13:
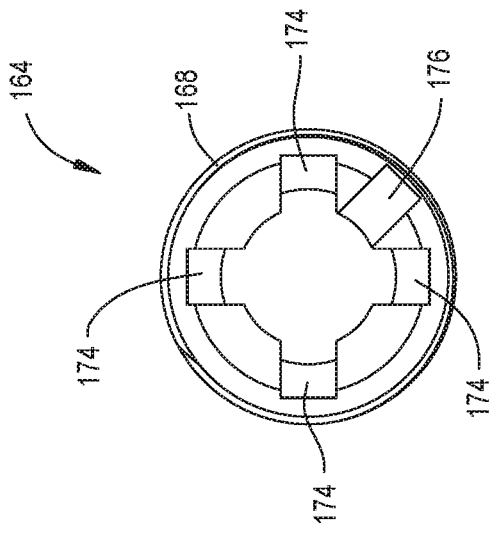
FIG. 13 is a plan view of the proximal end face of the slide.
Figure 14:
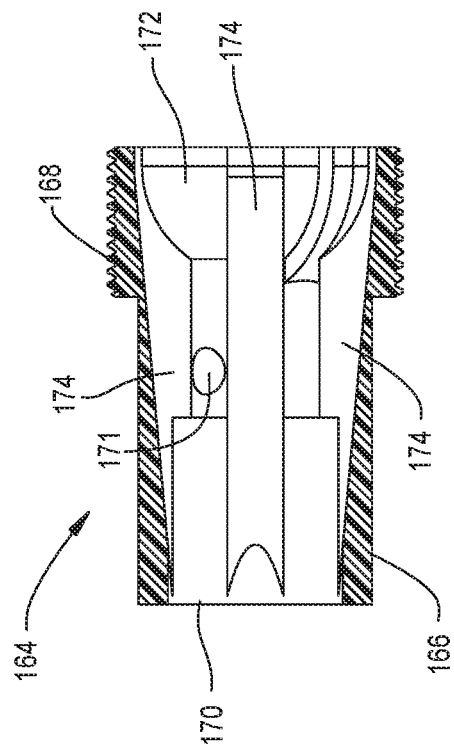
FIG. 14 is a cross sectional view of the slide.

The steering arm 150 is mounted to a slide 164 that is moveably disposed in the proximal bore 136 internal to handle 102. The slide 164, as now described by reference to FIGS. 12-14 includes a cylindrically shaped stem 166. Stem 166 has a diameter that facilitates slip fitting and longitudinal movement of the stem in handle proximal bore 136. A head 168 is located at the proximal end of the stem 166 and forms the most proximal portion of the slide 164. The slide 164 is formed so that the head 168 has an outer diameter greater than that of both the stem 166 and the handle proximal bore 136. Slide 164 is further formed so there is threading (not identified) around the outer cylindrical surface of the head 168.

Slide 164 is formed so a cylindrical bore 170 extends proximally rearward from the distal end of stem 166. Bore 170 extends through stem 166 and a short distance into head 168. The bore 170 opens up into another void internal to the slide 164, socket 172. The slide 164 is formed so that the socket is in the form of a slice section through a sphere. More specifically, the slide 164 is formed so that socket 172 can receive the steering arm ball 156 and the ball can rotate within the socket. The slide 164 is also formed to have a bore 171, seen in FIG. 14, that extends radially outwardly from bore 170.

The slide 164 is formed so that five grooves extend inwardly from the inners surfaces of the slide that define bore 170 and socket 172 Each of these grooves in lateral cross section is rectangularly shaped. There are four equi-angularly spaced apart grooves 174. Each groove 174 extends from the proximal end of slide head 168 to a location proximally rearward of the distal end face of stem 166. Each groove 174 thus has a base defined by a surface internal to the slide that, extending proximally to distally along the length of the slide 164, angles towards the longitudinal axis of the slide The fifth groove, groove 176, only extends outwardly from the inner wall of the slide that defines socket 172. The groove 176 is located between two grooves 174.

Figure 12:
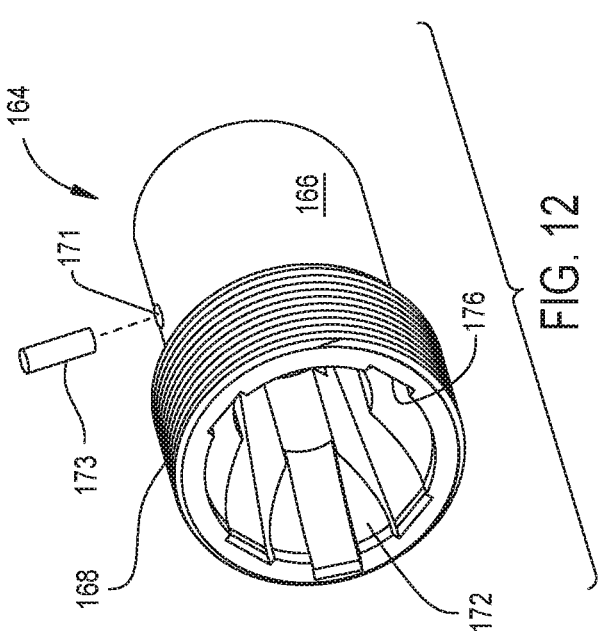
FIG. 12 is an exploded view of the slide and the pin that restricts movement of the slide.

As part of the process of assembling tool 110 of this invention, a pin 173, seen only in FIG. 12 is seated in slide bore 171. The pin 173 projects outwardly from the slide 164. When slide 164 is seated in the handle proximal bore 136, pin 173 is slidably disposed in handle notch 137. The presence of pin 173 in the notch 137 allows the slide to translate in the handle proximal bore 136 while preventing the rotation of the slide relative in the bore 136. A pin 178, seen only in FIG. 10, is also seated in bore 161 integral with the steering arm ball 156. Pin 178 protrudes out of the ball 156. During a later part of the assembly of the tool, the ball 156 is seated in the slide socket 172 so the pin 178 seats in groove 176. When the steering arm is so positioned, it is possible to displace the arm stem 152 such that the stem will pivot around the center axis of the ball 156. However, as a result of the seating of the pin 178 in the socket, rotational movement of the stem 152 around the longitudinal axis of the stem and like movement of the ball around this axis is blocked.

A collar 182, seen best is FIG. 15, is disposed around slide head 168. Collar 182 is generally ring shaped. The inners surface of the collar is provided with threading, (not identified). The collar 182 is formed so the inner threaded surface of the collar can thread on to the outer threaded surface of the slide head 168.

Figure 4:
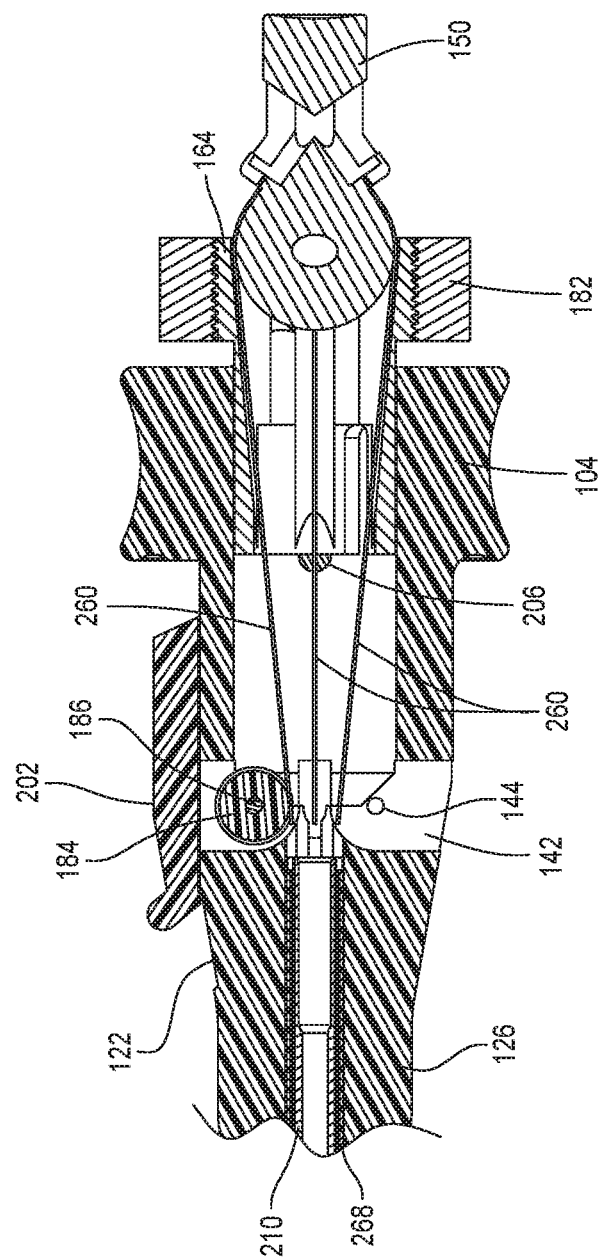
FIG. 4 is a cross sectional view of the proximal end of the surgical tool of FIG. 1 taken along a plane perpendicular to the plane of the cross section of FIG. 3.

Four rollers 184, one seen in FIG. 16, are rotatably mounted to the tool handle 102. Each roller 184 is generally disc shaped. Each roller 184 is formed to have a groove 183 that extends circumferentially around the outer cylindrical side wall of the roller. The roller is further formed to have opposed bosses 185 that extend away from the opposed top and bottom surfaces of the roller (one boss shown). Bosses 185 are centered on the axis that extends top to bottom through the roller. An axially extending through bore 186 extends through the bosses 185 and the body of the roller. Each roller 184 is rotatably mounted to the housing so as to be located in the end of a separate one of the bores 142. A pin 188 rotatably holds each roller in the associated bore 142. The opposed ends of each pin 188 are seated in the opposed portions of each bore 144 that intersects the bore 142 in which the roller is disposed. Collectively, the components forming tool 110 are arranged so that the rollers 184 do not abut. For ease of illustration, only a single roller 184 is seen in FIG. 4.

FIG. 17 provides a detailed view of the lock lever 190. The lever 190 is a single piece unit that has a center plate 198. Generally, the center plate 198 is shaped so that the proximal end of the plate is longer in length than the distal end. Legs 196, one leg seen, extend proximally and outwardly from the opposed sides of the center plate 198. A planar-shaped foot 195 extends proximally from each leg 196. Feet 195 are parallel to each other. The lever 190 is shaped so that when tool 110 is assembled the inner surface of each foot 195 can be disposed against one of the flat surfaces 108 integral with the handle 102. At the proximal end each foot 195 areas two proximally directed surfaces that are contiguous and angled relative to each other. The edges of one pair of these surfaces are called out in FIG. 17. One surface is a relief surface 194. Relief surface 194 angles proximally and downwardly away from the top surface of the foot with which the surface 194 is integral (top surface not identified). The second surface, a lock surface 193, extends downwardly from the proximal end of the relief surface 194. The lock surface 193 is essentially perpendicular to the opposed top and bottom surfaces of the foot 195.

A tab 202 extends forward from the distal end of the lever center plate 198. In the depicted version of the invention the distal end tip of tab 202 is flared upwardly. The lock lever 190 is further formed to have two coaxial through bores 204. Each bore 204 extends through a separate one of the feet 195.

Upon assembly, each foot 195 is located adjacent a separate one of the handle flat surfaces 108. The center plate 198 is located over one of the flat surfaces 114. Two pins 206, seen only in FIG. 17, pivotally hold the lock lever to handle 102. Each pin 206 extends through one of the tabs bores 204 into an adjacent one of the handle bores 135. The components forming the tool 110 are arranged so that when the lever is positioned so that the lever relief surfaces 194 are the surfaces of the lock lever closest to collar 182 the surfaces 194 are spaced from the collar. When the lever is pivoted so the lock surfaces 193 are the closest lever surfaces to the collar 182, the lock surfaces press against the distally directed face of the collar.

The tool shaft 210, seen best in FIGS. 18-20, is typically formed from a single piece of metal. The shaft 210 is generally in the form of an elongated cylindrically shaped tube. Not identified is the lumen that extends through the shaft 210. At the proximal end, the shaft 210 has a rim 212 that extends circumferentially around and radially outwardly from the main body of the shaft. Collectively the components forming tool 110 are formed so that the outer perimeter of rim 212 abuts the inner cylindrical wall of the handle 102 that defines distal bore 140.

Tool shaft 210 is further formed so that four equiangularly spaced apart grooves 214, two seen in FIG. 18, extend longitudinally along the length shaft. Each groove 214 terminates at notch 216 formed in the rim 212. Shaft 210 is further formed to have at the distal end a socket 218. The socket 218 is a void space that is the form of a slice section through a sphere.

Figure 22:
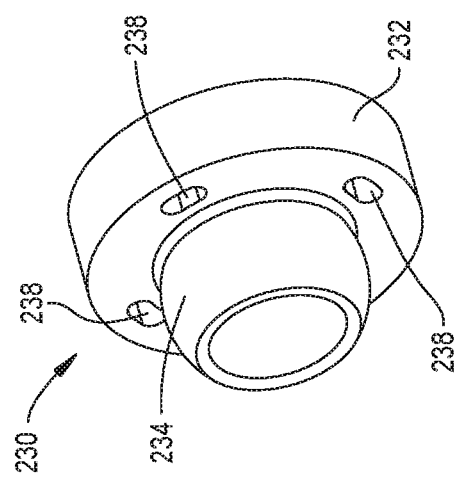
FIG. 22 is a perspective view of a link that is located forward of the distal end of the shaft.
Figure 23:
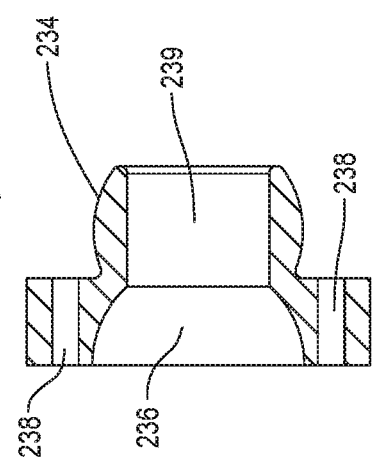
FIG. 23 is a cross sectional view of the link.
Figure 26:
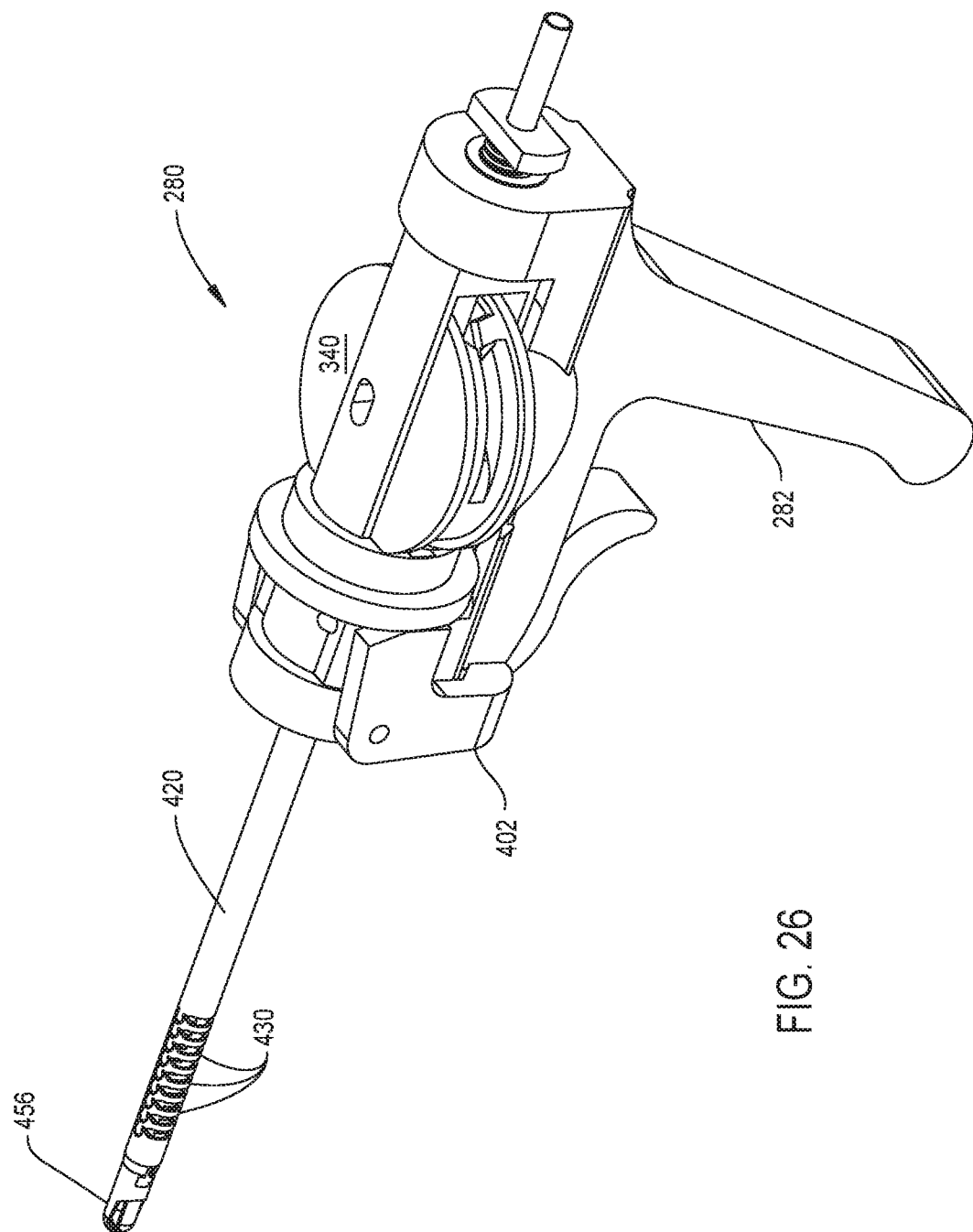
FIG. 26 is a perspective view of a first alternative surgical tool of this invention.

FIGS. 22 and 23 illustrate a single one of the links 230. In many versions of the invention, links 230 are formed from metal. A link 230 is shaped to have a disc shaped base 232. A foot 234 extends proximally from the base 232. The foot 234 is in the shape of a truncated sphere. More particularly the foot is in the form of a sphere slice wherein the proximal and distal polar regions of the sphere are absent. The equator, widest diameter slice section of foot 234, is parallel to the plane of the base 232. The radius of the sphere at the equator is less than the outer radius of the base 232.

Each link 230 is further shaped to have a void space, a socket 236, that extends proximally from the distally directed face of the base 232. Socket 236 is defined by a surface 235 and is semi-spherical in shape. More specifically each socket 236 is dimensioned to receive the foot 234 of the distally adjacent link 230. Foot 234 is thus a protuberance that extends into socket 236. The depth of the sockets is such that when a foot of one link is seated in the socket of an adjacent link and the two link heads are parallel, the link heads are spaced longitudinally apart from each other. This spacing of the link heads from each other means that, when the links are so arranged, each link 230 is able to pivot relative to the extension of the longitudinal axis from the proximally adjacent link.

Each link 230 is further formed to have four equiangularly spaced apart through bores 238, three bores 238 seen in FIG. 22. Through bores 238 are oval in cross section and extend through sections of the base 232 spaced from the socket 236. In the depicted version of the invention, the foot 234 is formed to have a cylindrically shaped through hole 239.

The previously described socket 218 internal to shaft 210 has the same shape and dimensions as the lock sockets 236. This allows the foot of the proximal most link 230 to be seated in the shaft socket 218. By extension, this allows the proximal most link 230 to pivot relative to the longitudinal axis of the shaft 210.

Figure 24:
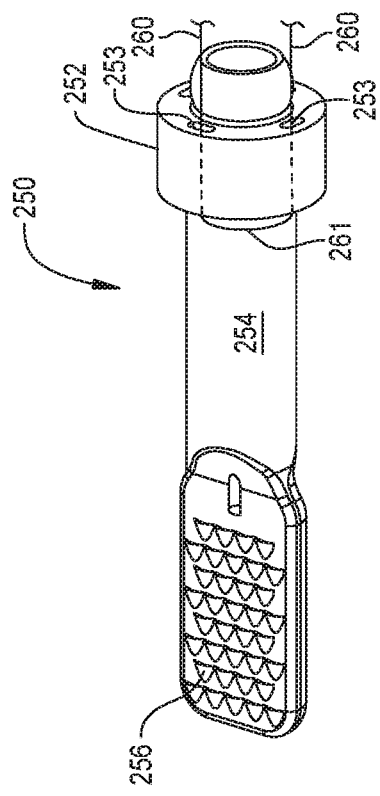
FIG. 24 is a perspective view of one tissue working member that can be disposed forward of the shaft of the tool of FIG. 1.

An exemplary tissue working member 250 that can be integrated into surgical tool 110 is now described with reference to FIG. 24. The tissue working member 250 includes a proximally located foot 252. The foot has the same general shape as the previously described links 230. A difference in the two components is that the cylindrical, ring shaped section of the foot is slightly large in length than the base 232 of a link 230. Bores 253, two shown, are analogous to link bores 238. A cylindrical leg 254 extends distally forward from the foot 252. Leg 254 has an outer diameter that is less than the outer diameter of the ring-shaped portion of the foot 252.

The tissue working component 256 is attached to the distal end of leg 254. In the depicted version of the invention the tissue working member is a rasp. This is understood to be exemplary, not limiting. The tissue working member can be any device intended to perform a procedure on the tissue to which it is applied. These devices for example include electrodes, ultrasonic vibrators, mechanical cutting and boring devices and devices that emit photonic (light) energy. A tissue working member of this invention is further understood a device that may be position on or adjacent tissue to perform a diagnostic function. This type of tissue working member can include a lens at the distal end of fiber optic cable or a pressure transducer.

When a surgical tool 110 of this invention is assembled, the shaft 210 is disposed in and extends forward out of the handle distal bore 140. More particularly, the shaft 210 is positioned so that the rim 212 is seated in the step that defines the transition between second torso bore 139 and handle distal bore 140. Shaft 210 is further positioned so each rim notch 216 is in registration with one of the grooves 141 that extend radially outwardly from the second torso bore 139. A number of links 230 are arranged in series to extend forward from the distal end of the shaft 210. The foot 234 of the proximal most link 230 seats in shaft socket 218. The spherical distal end of the tissue working member foot 252 seats in the socket 236 of the distal most link 230. The components are arranged so that each link bore 238 is aligned with the link bore of the adjacent link. The proximal most link bores 238 are each aligned with a separate one of the shaft grooves 214. The tissue working member is set so that each bore 253 is aligned with a bore 238 of the distal most link 230.

The described version of the invention has four steering cables 260. The cables 260 are paired such that the distal ends of two cables are connected by a bend 261. A first crimp 262, seen in FIG. 10, extends over the end of one cable 260. The first crimp 262 is seated in one of the recesses 158 formed in the steering arm 150. The cable 260 extends distally forward through the slot 160 in the ring 154 integral with the steering arm. Cable 260 then extends over the surface of ball 156 as seen in FIG. 4. When the first cable 260 passes through the slide 164, the cable extends through one of the grooves 174 formed in the slide.

Figure 21:
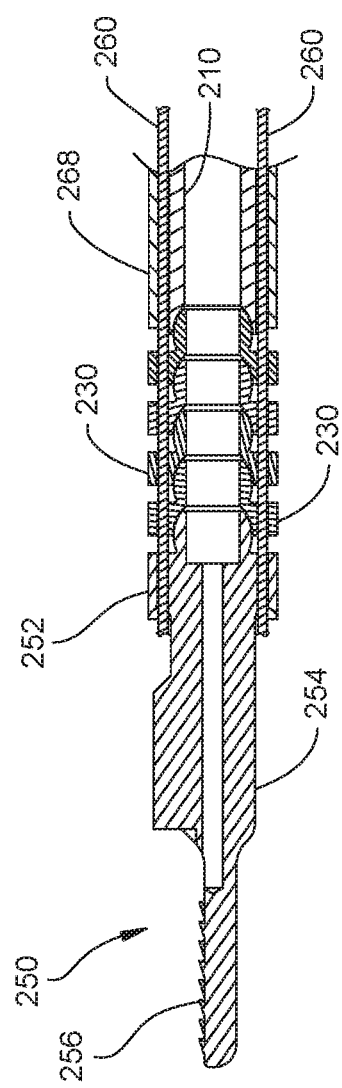
FIG. 21 is a cross sectional view of the tool shaft, links and tissue working member

From the slide 164, the cable 260 passes through the portion of the handle proximal bore 136 forward of the slide. The cable 260 then enters the torso first bore 138. As the cable 260 extends through bore 138, the cable presses against one of the rollers 184. More specifically, the cable 260 is seated in the groove 183 that extends around the roller. As a result of the cables 260 bending around the rollers 184, distal to the rollers, the cables are essential parallel to each other. Once a cable 260 curves around a roller, the cable enters an adjacent groove 141. From the groove 141 contiguous with the second torso bore 139, the cable 260 extends through the shaft groove 214 contiguous with the notch 216. Cable 260 then passes through the link bores 238 that are in registration with the shaft groove 238 as seen in FIG. 21. From the distalmost link 230 the cable extends through the adjacent bore 253 internal to the shaft foot. Upon exiting the bore 253, the first cable 260 meets the bend 261 located at the distal end of a second cable 260 as seen in FIG. 24. Bend 261 extends over the distally directed face of the foot 252 integral with tissue working member 250. The second cable 260 extends proximally from the bend 261 into the radially adjacent bore 253. The second cable 260 then passes through the link bores 238, the shaft groove 214 and rim notch 216 associated with this second bore 238. From the rim notch 216, second cable 260 transits through a groove 141, around an adjacent roller 184, and into the handle proximal bore 136. From bore 136, the cable extends back into slide 164. In the slide 164, the second cable 260 extends through one of slide grooves 174 and over the ball 156. The cable extends through the ring slot. The proximal end of the second cable 260 terminates at second crimp 262 seated in one of the steering arm recesses 158 that is radially adjacent the recess 158 in which the first crimp is seated.

The third and fourth cables 260 extend through the remaining two sets of the above described void spaces in the components. The opposed ends of the second cable are understood to be retained by crimps seated in the remaining two recesses 158 of the steering arm 150.

A sleeve 268 extends over the shaft 210. The sleeve 268 extends over the portion of the shaft disposed in the handle distal bore 140. Sleeve 268 extends forward of the handle 102. The distal end of the sleeve 268 is located within 1 to 3 cm of the first link 230.

To ready the tool for use, the lock lever 190 is pivoted so that tab 202 is spaced from the handle 102. This is the bending enabled position. When lock lever 190 is in this state, the feet relief surfaces 194 are the surfaces closest to collar the collar 182. This means the slide 164 and collar are free to move relative to the handle 102. The collar 182 is rotated to set the longitudinal position of the slide 164 within handle proximal bore 136. More specifically the position of the slide 164 and, by extension, steering arm 150 relative to the handle is set so the cables 260 are slightly in tension. The placing of the cables 260 in tension results in the exposed cable bends 261 pressing proximally against foot 252 of the tissue working member 250. The distal ends of the cables 260 the ends of the cables immediately proximal to the bends 261 are thus held fast to the tissue working member 250.

A practitioner uses the surgical tool 110 of this invention to position the tissue working member 250 at a location internal to the patient that otherwise cannot be easily accessed. By holding the handle 102, the practitioner inserts the shaft 210 into a portal or passageway internal to the patient that leads to the site at which the tissue working member is to be applied. This portal or passageway may be a natural passageway in the patient such as a vein or an artery. Alternatively, the passageway may be defined by a device such as an access tube.

As the tool is positioned, it may be necessary to bend, curve, the tool to position the tissue working member at the site to which the member is to be applied. The practitioner so bends the tool by pivoting steering arm 150. More particularly arm stem 152 is pivoted. As a result of this movement of the stem 152, the ball 156 is rotated. Again, owing to the presence of pin 178 in groove 176, the ball 156 only rotates around two axes. The ball 156 is restrained from rotation around the longitudinal axis through handle 102.

Figure 25:
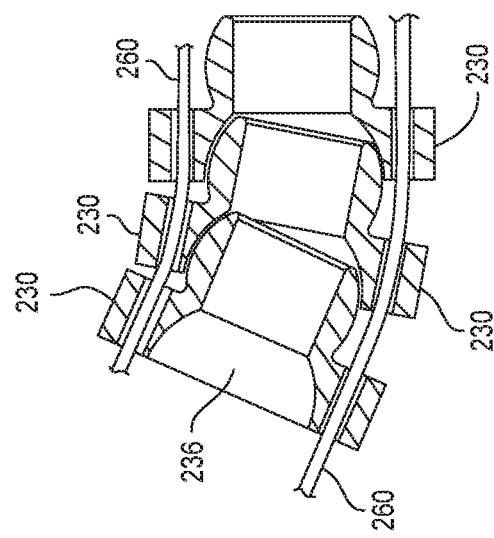
FIG. 25 is a cross sectional view depicting how as the result of the tensioning of a cable, the links form a curved or bent assembly.

The rotation of ball 156 increases the tension on at least one of the cables 260. At least one of the cables 260 is able to go slack. The cable/cables in tension is/are restrained from moving out of shaft groove/grooves 214 in which the cable/cables is/are seated. The cable/cables under tension pull the side of the foot 252 integral with the tissue working member towards the proximal end/ends of the tensioned cable/cables as seen in FIG. 25. As a consequence of the slackening of the at least one cable and the tensioning of at least one of the other cables. The asymmetric loading of the tissue working member causes the ball 257 of the foot to pivot in the link socket 236 in which the ball is seated. Depending on the degree of tension, the feet 234 of the links 230 are similarly pivoted in the sockets 236 in which the ball is seated. As a result of this pivoting motion, the links 230 and the tissue working member 250 develop the bend desired by the practitioner. In FIG. 25 it is the top located cable 260 that is pulled into tension. The disclosed version of the invention has four cables that can be selectively tensioned. Thus the links of the tool 110 can be pivoted so the tool acquires a bend that has components that are both up down relative to the longitudinal axis of the tool seen in FIG. 21 and in and out of the plane of the tool of FIG. 21. As a result of the tool bending, the tissue working member 250 aligned along an axis different from the axis along which the member is aligned when the tool is not bent.

Once tool 110 is so bent, the practitioner may want to lock the tool to prevent the curve of the bend from shifting. To perform this action, the practitioner pivots the lock leaver 190 downwardly. This results in lever lock surfaces 193 pressing against the distally directed face of collar 182. At this time, lever 190 is in the locked position. The component-against-component abutment caused by placement of the lever in the locked position displaces the collar 182 proximally rearward. By extension, the movement of the collar 182 results in a like displacement of the slide 164 and lever arm 150. This movement of the lever arm places a tension each of the cables 260. This includes the cables 260 that previously went slack as a result of the rotation of the ball 156.

The tensioning of the cables 260 causes the cables to pull the tissue working member 250 towards the handle 102. This displacement of the tissue working member 250 compresses the links 230 together. More precisely the ball 257 integral with the tissue working member 250 is pushed against the surface of the adjacent link that defines the socket 236 in which the ball is seated. Each link foot 234 is pushed against the socket-defining surface of the link socket 236 in which the foot is seated. The foot 234 of the proximal most link is pressed against the shaft socket 218 in which the link is seated.

Thus, the links 230, while angled relative to each other, are compressed between, at one end, shaft 210 and, at the other end, tissue working member 250. This compression prevents the links 230 from pivoting relative to each other. This means that when the tool of this invention is in the lock state, the bend formed by the links 230 is held static. The bend is held static even when the links are exposed to some side loading.

After the tool 110 is bent to have a specific curvature, it may be necessary to reshape the bend. This may be necessary to withdraw the tool from the portal in which the tool is seated. Alternatively, this may be necessary to facilitate the new positioning of the tissue working member 250. Whatever the reason, the recurving of the bend starts with the pivoting of the lock lever 190 back to the bend enable position. This makes it possible for the collar to move distally forward. As a result of the cable 260 being in tension when this invention occurs, the cables slightly pull the steering arm 150, collar 182 and slide 164 forward. This movement takes the tension out of the cable/cables 260 placed in tension by the movement of the lever 190 to the locked position. Once the tension is released on the cables, by the pivoting of the steering arm stem 152, the practitioner can again selectively tension the cable so the links form the bend desired by the next step of the procedure. The practitioner can then reset the lock lever 190 to the locked state if it is desirable to hold the links 230 to the shape of the new curve.

II. First Alternative Embodiment

An alternative surgical tool 280 of this invention is now described by initial reference to FIGS. 26-29. Tool 280 includes a handpiece 282 that is analogous to the previously described handle 102. An outer tube 420 that is analogous to the previously described shaft 210 extends distally forward from the handle. A set of links 430 are located forward of the outer tube 420. A tip 456, that is analogous to the tissue working member 250, is attached to the distalmost link 430. Two reins 468 (seen symbolically in FIG. 29), analogous to the steering cables 260, extend forward from the handpiece 282. Reins 468 are attached to the tube tip 456. A steering wheel 340 is mounted to handpiece 282 so to be able to rotate. Steering wheel 340 is also able to move longitudinally along the handpiece 282. The reins 468 are mounted to the steering wheel 340 to be selectively tensioned by the rotation of the steering wheel. A lock lever 402 controls the position of the steering wheel 340 along the handpiece 282.

Figure 28:
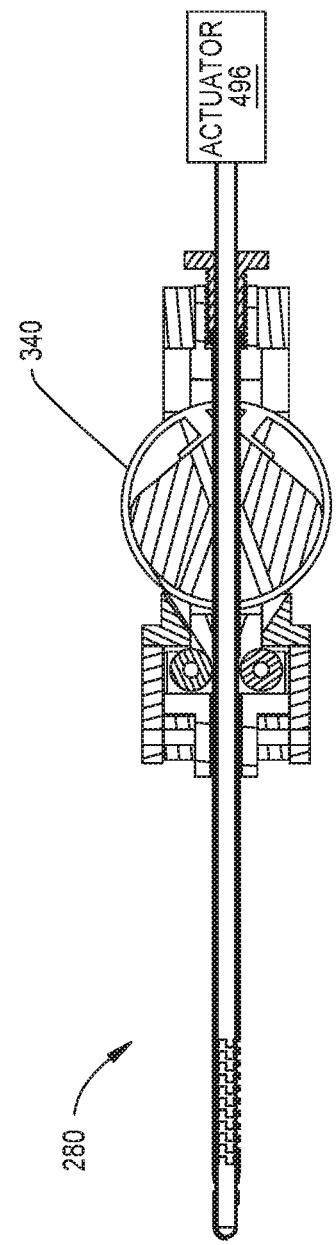
FIG. 28 is a cross sectional view of the first alternative surgical tool.
Figure 35:
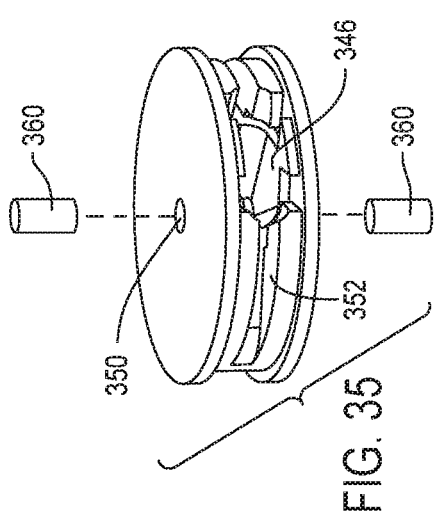
FIG. 35 is an exploded view of the steering wheel of the first alternative surgical tool and the pins that hold the steering wheel to the rest of the tool.
Figure 36:
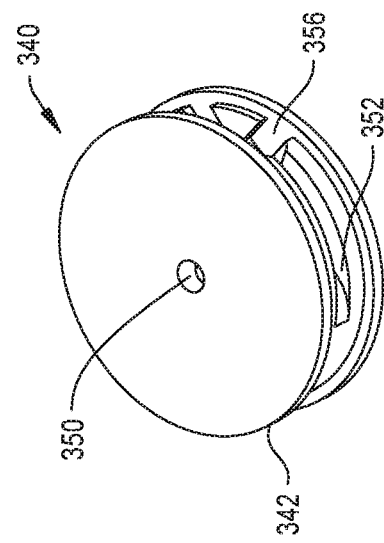
FIG. 36 is a perspective view of the steering wheel.

Tool 280 also has an inner tube 482 that is disposed in the outer tube 420. A cutting feature 490 is mounted to the distal end of the inner tube 482. An actuator 496, seen only as a block element in FIG. 28, is attached to the proximal end of the handpiece 282. The actuator 496 rotates the inner tube 482 to cause a like rotating of the tube cutting feature 490.

Figure 30:
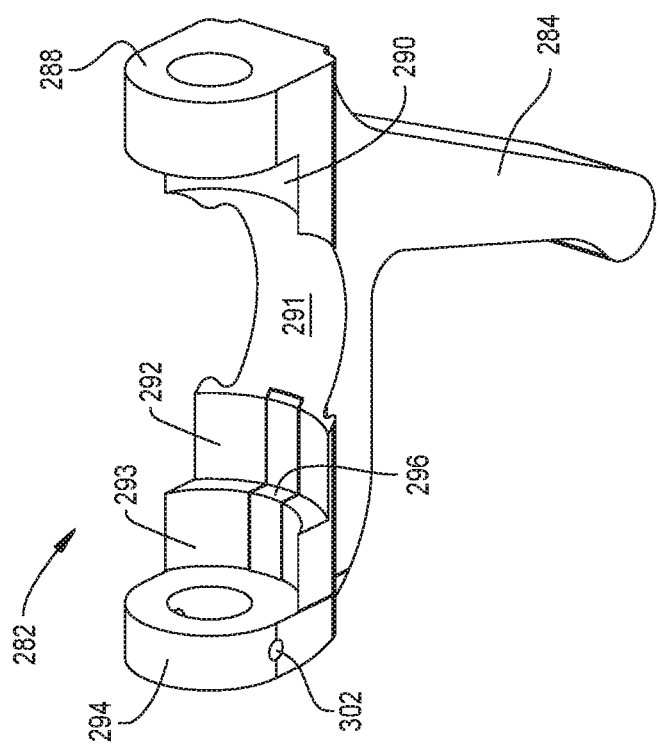
FIG. 30 is a perspective view of the body of the first alternative surgical tool.
Figure 32:
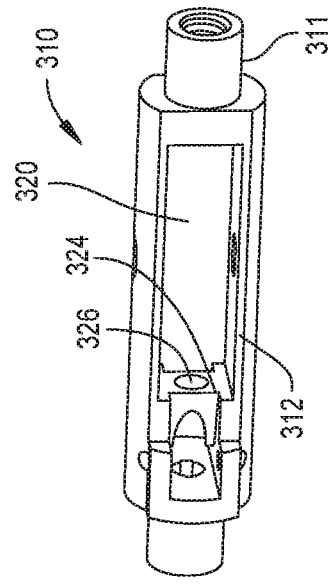
FIG. 32 is an alternative perspective view of the core.
Figure 34:
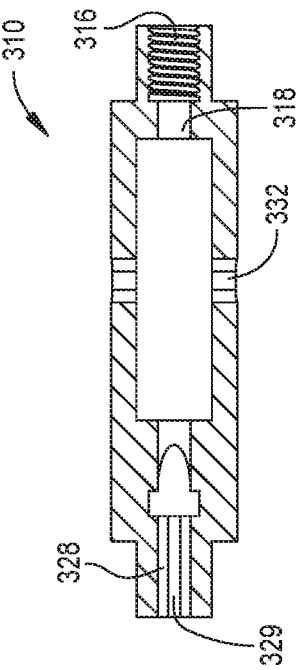
FIG. 34 is a cross sectional view of the core in a plane perpendicular to the plane of FIG. 33.
Figure 31:
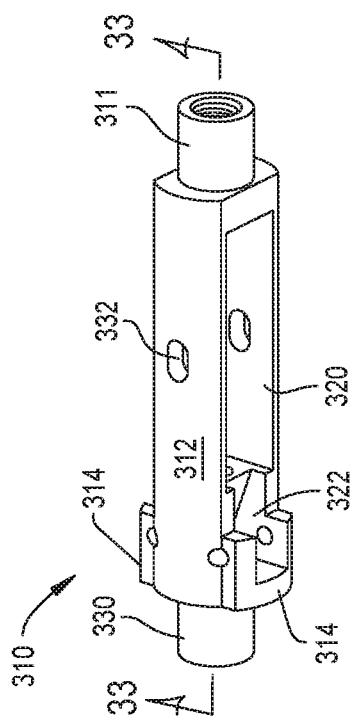
FIG. 31 is a perspective view of the core in which the steering wheel of the first alternative surgical tool is held.
Figure 33:
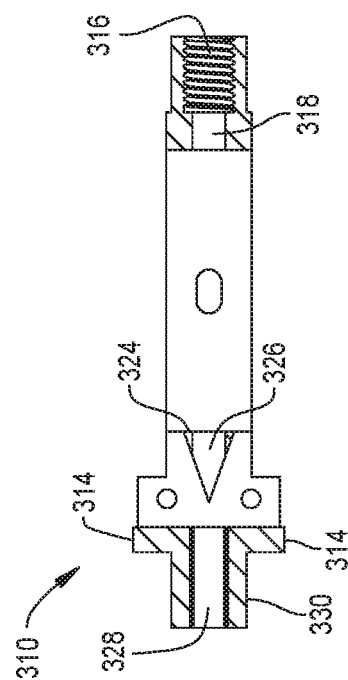
FIG. 33 is a cross sectional view of the core of FIG. 31 taken along line 33-33.

The handpiece 282, as seen in FIG. 30, is pistol shaped so as to have a grip 284. A beam 286 extends forward from a top end of the grip 284. Two brackets 288 and 294 are mounted to the beam 286 so as to extend above the top surface of the beam. A first bracket, bracket 288, is mounted to the beam 286 adjacent the proximal end of the beam. Bracket 294 is mounted to the beam 286 adjacent the distal end of the beam. Both brackets 288 and 294 have outer top surfaces that are semi-circular in shape. Each bracket is formed with a through hole that extends proximally to distally through the bracket (through holes not identified). The bracket through holes are coaxially aligned.

Proximal bracket 288 is integrally formed with the rest of the handpiece. Distal bracket 294 is formed separately from the rest of the handpiece. When the distal bracket 294 is formed, a stepped proximally extending tab 296 is formed with the bracket. The handpiece 282 is formed so as to have a stepped slot (not identified) that extends inwardly from the exposed face of the beam 286 adjacent the distal end of the beam. As part of the process of assembling tool 280, the tab 296 is seated in the complementary slot so as to secure the distal bracket 294 to the rest of the handpiece 282. In some versions of the invention, pins that extend laterally through coaxial bores in the beam 286 and tab 296 hold the tab to the rest of the handpiece. (Pins and bores not illustrated.)

Handpiece 282 is further formed so immediately forward of bracket 288 beam 286 has a surface 290 and immediately rearward of bracket 294 there is a surface 293. Immediately proximal to surface 293 the beam has a surface 292 that is stepped below surface 293. Surfaces 290 and 292 are curved around a common axis that is parallel to the longitudinal axis of the handpiece 282. Between surface 290 and surface 292 the handpiece has a surface 291 that is located below both surfaces 290 and 292. Surface 291 is curved around an axis that is perpendicular in a horizontal plane to the longitudinal axis through the handpiece.

The handpiece is further formed to have two bores 302 one seen in FIG. 30. Each bore 302 extends inwardly from a side surface of the distal bracket 294. Bores 302 are coaxial.

The steering wheel 340 is rotatably mounted in a case 310 seen best in FIGS. 31-34. Case 310 is shaped to have a center core 312 that is generally in the form of cylinder that opposed longitudinally extending sides of which have been removed. Wings 314 extend laterally outwardly from the opposed ends of the core 312. Opposed trunnions 311 and 330 extend longitudinally outwardly from, respectively, the opposed proximal and distal end of the core 312. Trunnions 311 and 330 are cylindrically shaped and coaxial. The diameter of trunnions 311 and 330 is less than the diameter of the circle defined by the core 312. More specifically, trunnion 311 is designed to fit the through bore formed in the handpiece proximal bracket 288. Trunnion 330 is designed to fit in the through bore internal to the handpiece distal bracket 294.

Case 310 is further formed to have a threaded bore 316 that extends distally forward from the proximal end of trunnion 311. Bore 316 opens into a bore 318 formed in the wall that forms the proximal end of core 312. Within core 312 there are two void spaces 320 and 322. Both void spaces 320 and 322 are open to the opposed longitudinally extending sides of the core 312. Void space 320, the void into which bore 318 opens, is in terms of length, the longer of the two void spaces 320 and 322. Void space 320 has a length that is between one-half and three-quarters the whole length of the core 312. Void space 320 opens into the adjacent distally located void space 322. Void space 322, in addition to being shorter in length than void space 320, is shorter in top-to-bottom height. Case 310 is formed so that the void space 322 extends from the outer side of one wing 314 to the opposed outer side of the opposed wing.

The case 310 is further formed so that a post 324 extends between the opposed top and bottom interior surfaces of the core 312 that define void space 322. In a horizontal cross-sectional plane perpendicular to the longitudinal axis through the case 310, the post 324 would appear triangular in shaped. The apex of the post triangle is both directed to and spaced longitudinally away from the surface internal to the core 312 that defines the distal end of void space 322. A bore 328 extends proximally rearward from the distal end of trunnion 330. Bore 328 opens into the distal end of void space 322. Bore 328 is generally cylindrical in shape. Case 310 is, however, formed so to have two opposed grooves 329, one seen in FIG. 34, that extend outwardly from the inner wall of the case that defines bore 328. The case 310 is formed so that grooves 329 are located on longitudinal axes that are in or at least parallel to the plane of case in FIG. 33. A bore 326 extends through post 324. Bores 316, 318, 326 and 328 are coaxial.

Case 310 is formed to have three additional bores each of which extends top-to-bottom through the case. A bore 332 extends through the top and bottom structural webs of the core 312 that define void space 320. Bore 332 thus intersects void space 320. The case 310 is formed so that bore 332 is oval in cross section and is aligned so the major axis of the bore 332 is parallel with the longitudinal axis of the case 310. There are two additional bores, bores 334. Each bore 334 extends top-to-bottom through the case 310 where one of the wings 314 extends outwardly from the core 312. Each bore 334 thus intersects void space 322.

FIGS. 35-40 provide the best views of the steering wheel 340. The steering wheel 340 is generally spool shaped so as to have a cylindrical base 344 from which rims 342 and 358 extend radially outwardly. More particularly rim 342 extends radially outwardly from and circumferentially around the base 344 around the top surface. Rim 358 extends radially outwardly from and circumferentially around the bottom of the base 344. The components forming tool 280 are dimensioned so that the top-to-bottom height of the steering wheel allows the wheel to seat in case void space 320. The diameter of the wheel rims 342 and 358 is approximately 0.5 cm less than the length of the case void space 320.

Steering wheel base 344 is formed to have a number of bores and voids. A proximal bore 346 extends inwardly from the proximal end of the base to the top-to-bottom center axis through the wheel 340. When the steering wheel is in the center position bore 346 is centered along the longitudinal axis of the handpiece. Steering wheel 340 is formed so that bore 346 is tapered such that, extending distally forward from the outer surface of base 344, the width across the bore decreases. Bore 346 terminates at the center axis of the steering wheel 340. A distal bore, bore 348, is contiguous with and extends distally forward from bore 346. Bores 346 and 348 share a common longitudinal axis. From the center axis of the steering wheel, the base 344 is formed so that extending distally forward, the width of bore 348 increases. The steering wheel is further formed so that inner side walls of the base 344 that define bores 346 and 348 are concave in shape. Thus, in cross section, in planes perpendicular to the longitudinal axis through the bores 346, 348, each bore 346 and 348 appears oval in shape. A cylindrical though bore 350 extends top to bottom through the steering wheel 340. Bore 350 thus intersects the interface between bores 346 and 348.

The steering wheel 340 is further formed to have grooves 352 that extend inwardly from the outer arcuate surfaces of the base 344. From FIG. 39 it can be seen that each groove 352 starts at location that is on a line that extends from the interface between bores 346 and 348. Extending proximally from this location, as the groove 352 extends proximally, the depth of the groove increases. Adjacent the proximal end of proximal bore 346, the base 344 is further formed to define two notches 356. Notches 356 are symmetric with respect to the longitudinal axis through bore 346. The notches 356 are L-shaped. The steering wheel 340 is formed so that each notch 356 intersects the adjacent side of the proximal bore 346 and the base of the groove 352 that extends to that side of the bore 346.

When tool 280 is assembled, steering wheel 340 is disposed in void space 320 internal to the case 310. Two axially aligned pins 360, seen only in FIG. 35, rotatably hold the steering wheel 340 to the case 310. Each pin 360 is mounted in a separate end of bore 350 and extends outwardly away from the steering wheel 340. One pin 360 extends upwardly from the steering wheel 340 to seat in the top portion of case bore 332. The second pin 360 extends downwardly so as to seat in the bottom portion of case bore 332. Owing to the dimensioning of the components, pins 360 are able to engage in rotation movement on case bore 332 and move longitudinally in the bore 332.

A lock ring 364, seen best in FIG. 41, is slidably disposed over the case 310. Lock ring 364 includes a circularly shaped core 366 that has a through opening (not identified). The core through opening is defined by opposed top and bottom inner surfaces 368 and 370, respectfully. Top and bottom inner surfaces 368 and 370, respectively, are arcuate in shape and symmetric with respect to each other around the longitudinal axis that extends proximally to distally through the through opening. Two opposed inner side surfaces 372, one side surface identified, extend between the adjacent ends of the top and bottom inner surfaces, 368 and 370, respectively. Lock ring inner surfaces 368, 370 and 372 are collectively shaped relative to the case 310 to allow the longitudinal slip movement of the ring 364 over the case core 312 while preventing the rotation of the ring around the core.

Lock ring 364 is further formed so that rearward of the distal end of each side surface 372 there is a recessed face 374 (one identified). Faces 374 are curved. More particularly both faces 374 are curved around a slice section of a cylinder that has a diameter essential equal to the common radius of steering wheel rims 342 and 348. The faces 374 are curved so that, from the location where each face 374 starts, extending proximally, the face curves outer away from the longitudinal axis through the ring through hole. Each face 374 has a top-to-bottom length that facilitates the seating of a section of the steering wheel, from the top of rim 342 to the bottom of rim 358 against the beveled face. The lock ring 364 is further formed to have opposed grooves 376, one groove identified. Each groove 376 extends inwardly from the proximal end of the associated curved face 374. Each groove 376 is located inwardly from the beveled face 374 and the adjacent portion of the inner side surface 372 adjacent the distal end of the beveled face. Lock ring 364 is formed so that, as the groove 376 extends distally, the base of the groove tapers inwardly towards the longitudinal axis through the ring through bore. The lock ring 364 is further formed to have at the distal end a lip 378 extends radially outwardly from the ring core 366.

When tool 280 is assembled, the lock ring 364 is slipped over case 310 so the distally outer flat surface of the ring lip 378 is directed towards the adjacent proximally directed faces of the case wings 314. Ring faces 374 are thus generally directed proximally. The steering wheel 340 is disposed the case void space 320 and held to the case 310 by pins 360. The components forming tool 280 are dimensioned so that both the steering wheel 340 and lock ring 364 are able to engage in some longitudinal movement along the longitudinal axis of case 310.

Two rollers 380, one seen in FIG. 42, are also rotatably mounted to case 310. Each roller 380 is cylindrical in shape and has an axially extending through bore 384. A rim 382 extends circumferentially around the through bore 384 adjacent each circular face of the roller 380 (one rim seen in FIG. 42). Each roller 380 is seated in case void space 322 defined by one of the wings 314. A pin 386, seen only in FIG. 42, rotatably holds the roller to the wing 314 in which the roller is seated. The ends of the pin 386 that extend outwardly of the roller 380 seat in the opposed ends of the adjacent bore 334 that lead into the case void space.

As part of the process of assembling tool 280, the steering wheel 340 is mounted in case void space 320 so as to be able to rotate in and move longitudinally in the void space 320. Lock ring 364 is slip fit over the distal portion of the case core 312 so that beveled faces 374 are directed towards the steering wheel 340. Case 310 is mounted to handpiece 282 by seating case proximal trunnion 311 in the through bore internal to the handle proximal bracket 288. The handle distal bracket 294 is then attached to handle beam 286. As part of this assembly step, case distal trunnion 330 is seated in the through bore that extends through the handle distal bracket 294. When tool 280 is so assembled, the opposed proximal and distal sections of the case core 312 seat on, respectively, beam surfaces 290 and 293. Lock ring 364 is disposed above beam surface 292.

FIG. 43 illustrates a set screw 390 that is also coupled to case 310. Set screw 390 has a threaded base 392. Base 392 is dimensioned to be screw secured in the case threaded bore 316. A bar 394 extend radially outward from opposed sides of the base 392 at the proximal end. Set screw 390 is further formed to have an axially extending through bore 396. Bore 396 extends through the whole of base 392 and bar 394.

The lock lever 402 of tool 280 of this invention is seen best in FIG. 44. Lock lever 402 has a center plate 408. An L-shaped leg 404 extends proximally and then downwardly from the proximal end of center plate 408. An L-shaped arm 409 extends first upwardly and then proximally from each side of center plate 408. Arms 409 are in planes that are parallel to each other. The lock lever 402 is further formed so that the planes the arms 409 lie in are perpendicular to the planes in which the proximal and downwardly directed portions of the leg 404 are disposed. Each arm 409 has two generally proximally directed surfaces. Extending upwardly from the bottom of the arm there is a lock surface 410 (one identified). Lock surface 410 is perpendicular to the bottom surface of the leg, the surface of the leg from which the lock surface 410 extends upwardly. The second proximally directed surface of each arm 409 is the relief surface 411. The relief surface 411 extends diagonally upwardly and distally forward from the lock surface 410.

Each arm 409 is formed with a through bore 413. Bores 413 are coaxial. Lock lever 402 is pivotally mounted to the handpiece distal bracket 294. Specifically, the lock lever 402 is positioned so that the opposed inwardly directed surfaces of lever arms 409 are each located adjacent an outer side surface of the bracket 294. Pins 414, seen only in FIG. 44, extend through each lever bore 413 into an adjacent one of the bores 302 formed in the distal bracket 294. When tool 280 is assembled, the lock lever leg 404 is located forward of the handpiece grip 284. The lock lever leg 404 is the portion of the lever 402 that is manually set to transition the tool between the bend enabled and locked states.

The components forming surgical tool 280 are further formed so that when the lock lever 402 is pivoted so that the arm relief surfaces 411 are the closest lever surface to the lock ring 364, the relief surfaces are spaced from the lock ring. The lock lever 402 can be pivoted so that the arm lock surfaces 410 are the closest surfaces to the lock ring 364. When the lock lever 402 is in this position, the locked position, the lock surfaces 410 abut the lock ring 364.

Figure 46:
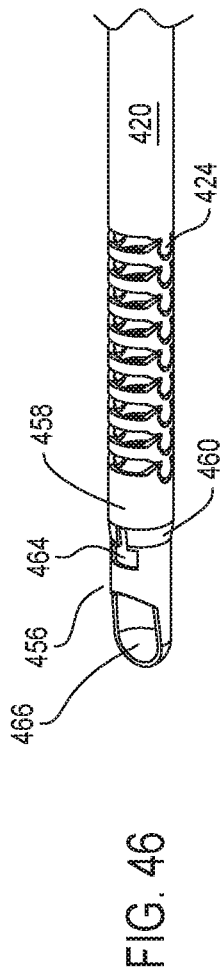
FIG. 46 is an enlarged perspective view of the distal portion of the tube of FIG. 45.
Figure 47:
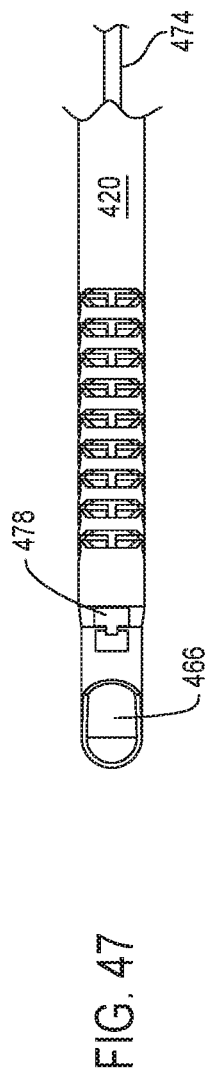
FIG. 47 is a plan view of the front facing surface of the tube of FIG. 45.
Figure 48:
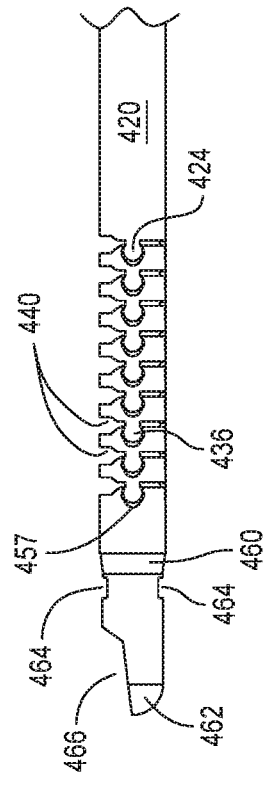
FIG. 48 is a plan view of a side facing surface of the tube of FIG. 45.
Figure 49:
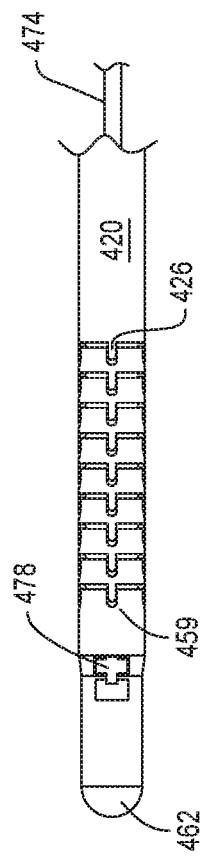
FIG. 49 is a plan view of the rear facing surface of the tube of FIG. 45 and one of the reins that extends out of the tube.

FIGS. 45 and 46 depict how the outer tube 420, links 430 and tube head 462 are fitted together. Outer tube 420, as implied by its name, is a tube-shaped structure. Not identified is the lumen that extends axially through the tube 420. The tube 420 is formed to have two diametrically opposed arms 424, one identified in FIG. 48, that extend forward from the distal end of the tube. At a location equiangularly spaced from both arms 424 a leg 426, seen in FIG. 49, also extends forward from the distal end of tube 420. Arms 424 are identical in shape so to the below discussed link arms 436. Leg 426 is identical in shape to the below discussed link leg 438. Accordingly, the shape of arms 424 and leg 426 will be understood from the below description of the elements of a link 430.

Outer tube 420 is further formed to have two windows 428, one window seen in FIG. 45. Windows 428 are diametrically opposed to each other around the longitudinal axis of the tube 420. The windows 428 are rectangularly shaped and are arranged so that their major axes are parallel with the longitudinal axis through the tube 420. Each window 428 opens into the lumen that extends through the tube.

The structure of a link 430 and the relationship of the link to the adjacent links is understood from FIGS. 48-51. A link 430 is shaped to have a frame 432. Frame 432 is generally tube shaped and has the same inner and outer diameters as outer tube 420. Two arms 436 protrude distally forward of the frame. Each arm 436 is generally circular in shape. A shoulder 434 is located between each arm 436 and the adjacent section of the frame 432 from which the arm extends. The width across a shoulder 434 is less than the diameter of the adjacent arm 436. A leg 438 also extends distally forward from the frame 432. Leg 438 is equiangularly spaced from the opposed arms 436. The leg 438 is in the form of an elongated beam with a rounded distal end tip (tip not identified).

The link 430 is further formed to define opposed cutouts 440 in frame 432. In FIG. 50, the Cutouts are formed in the frame in the section of the frame opposite the section from which leg 438 extends. One cutout 440 extends forward from the adjacent proximal end of the frame. The second cutout 440 extends rearward from the distal end of the frame 432.

Each link 430 is further formed to define void spaces for receiving the arms 436 and leg 438 of the proximally adjacent link 430. The arms 424 and leg 426 integral with the outer tube 420 seat in the below described void spaces of the proximal most link 430. Two of the void spaces are diametrically opposed sockets 450, two sockets identified in FIG. 50. Each socket 450 has a distalmost perimeter defined by a concave shaped base surface 442 in the link frame 432. Extending proximally rearward, the perimeter of the socket is defined by two symmetrically opposed surfaces 444 in the frame 432. (In FIG. 50 only the edges of surfaces 442 and 444 are seen.) Surfaces 444 are linear in shape and taper away from the base edge. The maximum width across the socket between surfaces 444 is greater than the diameter of the arm 436 seated in the socket 450. The link 430 is further formed to have what appear as two opposed tabs 446 each of which is located proximal to a separate one of the surfaces 444. Tabs 446 have opposed edges that are concave in shape (tab edges not identified). More particularly, the tab edges are disposed on a circle that has a diameter approximately equal to the diameter of the arms 436.

The additional void space formed in the tab frame 432 is a slot 452, seen best in FIG. 51. Slot 452 is shaped to slidably receiver the leg 438 of the proximally adjacent link 430. Slot 452 has a length that is approximately 2 mm greater in length than the length of the leg 438.

Tube tip 456, as seen in FIGS. 46-49, includes a cylindrical hollow base 458. Base 458 has the same inner and outer diameters and the outer tube 420 and the links. Extending forward from the base 458, tip 456 has a neck 460. Neck 460 is tapered such that the diameter of the neck decreases as the neck extends distally. A head 462 with a rounded nose extends forward from neck. Head 462 thus has a diameter less than that of the base. Tube base 458 is formed with sockets 457, one identified in FIG. 48, identical in shape to link sockets 450. Arms 436 of the distalmost link 430 seat in sockets 457. Tube base 458 is also formed to have a slot 459, seen in FIG. 49, identical to link slots 452. Leg 438 of the distalmost link 430 seats in slot 459.

The tube tip 456 is also formed to have two T-shaped windows 464, one of which is seen in FIG. 46. Windows 464 are diametrically opposed from each other. The center portion of each window 464 extends longitudinally through the tip neck 460. The cross portion of each window 464 extends through a proximal portion of the tube head 462. Tip 456 is further formed to define a cutout 466. Cutout 466 extends from the distal end of the nose, to where tip head 462 has a constant diameter. In the depicted version of the invention, the cutout subtends an angle of close to 180° around the longitudinal center axis of the tip 456. In some versions of the invention, the edges of tip 456 that define cutout 466 have teeth or other cutting surfaces.

Outer tube 420, links 430 and tool tip 456 are collectively arranged so that the link arms 436 and sockets 450 are in planes perpendicular to the planes along in which tube windows 428 are disposed. Link legs 438, cutouts 440, and slots 452 are located along planes parallel to if not the same planes as the planes in which windows 428 are disposed. Also disposed in planes parallel to the planes of windows 428 are tube tip windows 464.

In some methods of assembling outer tube 420 and the associated components, this sub-assembly is fabricated by first providing a closed end tube. The tube is swaged or otherwise formed to define tip neck 460 and tip head 462. The tube is then machined or cut define tube 420, links 430 and tube tip 456. This cutting can be performed by a laser cutting process. During this cutting process, windows 428 and 464 and cutout 466 are formed.

FIG. 52 is a plan view of one of the steering reins 468 of surgical tool 280. The rein 468 is in the form of elongated strip of flexible material. In one version of the invention, each rein is formed from stainless steel and has a thickness of approximately 0.08 to 0.15 mm. The rein 468 has a rectangularly shaped foot 470. Foot 470 is the widest component of the rein 468. A leg 472 extends distally forward from the foot. The leg 472 has a width, the length on the axis perpendicular to the longitudinal axis of the rein that is less than the width of the adjacent foot 470. Distal to the leg 472, the rein has a mid-section 474. The width across the mid-section 474 is less than the width across the leg 472. The rein mid-section 474 is dimensioned to extend through and move within a window 428 in the outer tube 420. Not identified is the tapered transition section between leg 472 and mid-section 474. The distal end of the mid-section 474 tapers inwardly to form an elongated neck 476. Neck 476 has a width that allows the neck to slip through the center, proximal-located portion of a tip window 464. A rectangular shaped head 478 is located at the distal end of the neck 476. The width across rein head 478 is greater than the width of neck 476 and the center portion of the tip window 464. The rein head is able to pass through the distally located large width portion of the window 464.

Figure 53:
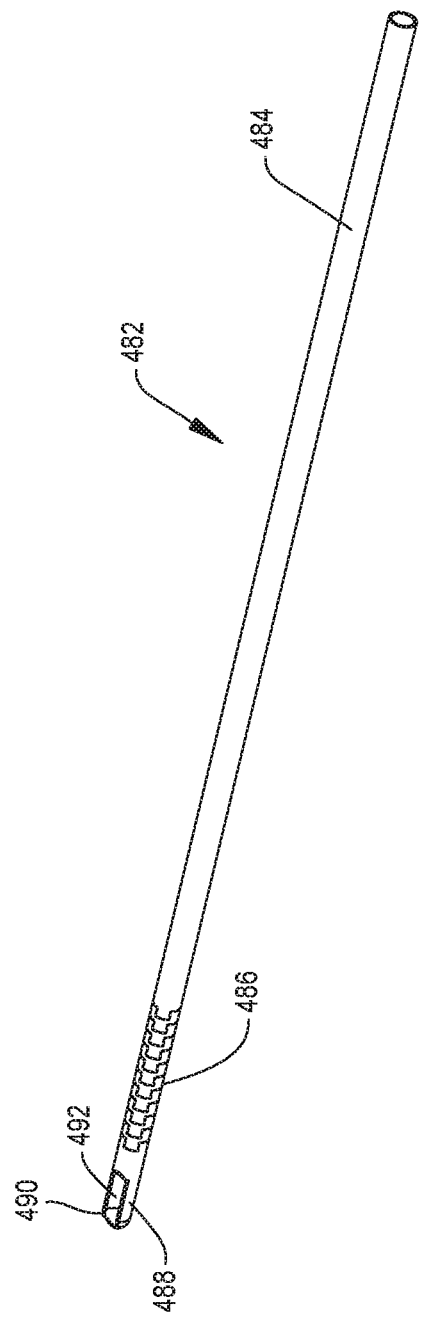
FIG. 53 is a perspective view of an inner tube of the first alternative tool.
Figure 56:
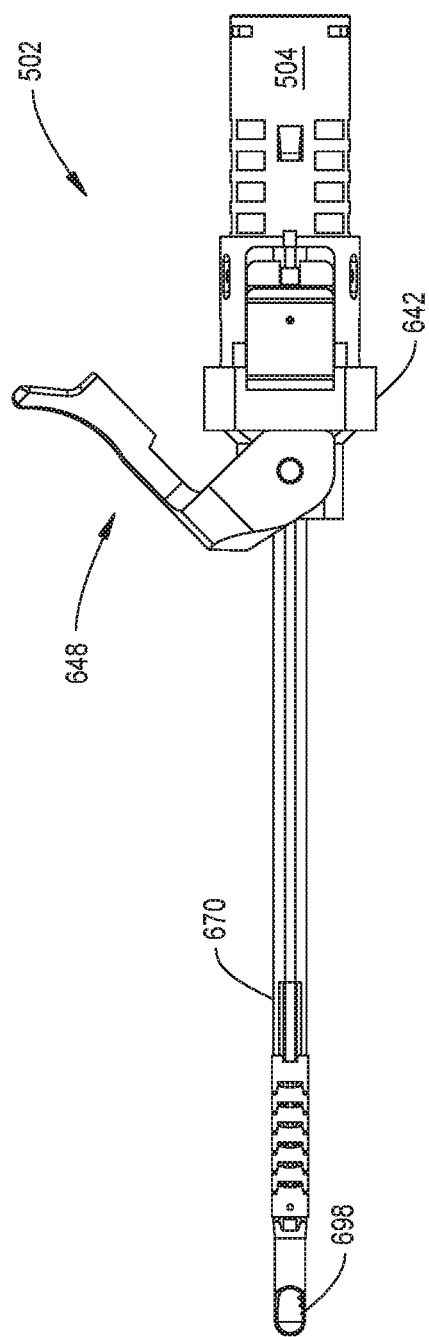
FIG. 56 is a side plan view of the tool of FIG. 54.

Tool inner tube 482, now described by reference to FIG. 53, is dimensioned to seat and rotate in the outer tube 420. More particularly, inner tube 482 is dimensioned to have an outer diameter that is approximately 0.1 mm less than inner diameter of head 462 integral with outer tube tip 456. Inner tube 482 has a main section 484. Tube main section 484 is longest section of the tube 482. While not illustrated, a hub is often attached to the proximal end of the tube main section 484. The hub has geometric features that facilitate the attachment of the inner tube 482 to a drive component of the actuator 496. This drive component is often a spindle capable of rotating the inner tube 482 or a link capable of reciprocating the inner tube 482.

Forward of the main section 484, the inner tube 482 has a flexible neck 486. A tip 488 is secured to the distal end of the neck 486 and is the most distal component of the inner tube 482. Tip 488 of the inner tube 482 is similar in shape to tip 456 of outer tube 420. The tip 488 has a cutout 492 similar in shape to cutout 466 of outer tube 420. The edge of tip 488 that defines cutout 492 is formed with a sharp edge or teeth (not illustrated). In this embodiment of tool 280, this sharp edge is the cutting feature 490 of the inner tube.

In some versions of the invention, the inner tube 482 is fabricated from a closed end tube. Slots and openings are formed in the tube so as define the neck 486 and cutout 492. More particularly, the neck 486 may be formed by providing a slot that is generally helical in shape. The slot while extending helically is further formed to define interlocking teeth (slot and teeth not identified). The exact structure of the inner tube with flexible neck is not part of the present invention. It should however be appreciated that when tool 280 is assembled, and the inner tube 482 is seated in the outer tube 420, inner tube flexible neck 486 is disposed within bendable links 430 that extend forward from the outer tube 420. Also, inner tube tip 488 is disposed in tip 456 attached to the outer tube so that inner tube tip cutout 488 is in registration with cutout 466 integral with outer tube tip 456.

When surgical tool 280 is assembled, the outer tube 420 is positioned so as to extend through the case trunnion 311 and through bores 346 and 348 of the steering wheel 340. The outer tube 420 is further positioned so that each tube window 428 is adjacent one of the rollers 380. Outer tube 420 extends through the through opening of the lock ring 364 and through and distally forward away from case bores 326 and 328. Set screw 390 is adhesively or otherwise secured to a portion of the outer tube 420 that extends through the case trunnion 311. The set screw 390 is threadedly fitted to case bore 316. The rotation of the set screw 390 thus allows the setting of the position of the distal end of the tube 420 relative to the front face of tool handpiece 282.

The proximally located foot 470 of the reins is located in the opposed notches 356 formed in the steering wheel 340. One rein 468 is seen in cross section in FIG. 39. The leg 472 of the rein seats in groove 329 immediately adjacent the notch. Thus, each rein 468 extends distally forward and laterally outwardly from the notch in which the rein foot 470 is seated. Upon exiting the distal end of groove 329, the rein 468 curves distally and inwardly around the adjacent arcuate surface of base 344 of the steering wheel.

When steering wheel 340 is in the center position, reins 468 do not curve completely around the adjacent arcuate surfaces of wheel base 344. Instead, proximal to the distal open end of surfaces of the portion of the reins extend diagonally both forwardly and inwardly toward each other. The reins 468 which are located adjacent the outer surface of the outer tube 420, extend along the opposed outer surfaces of post 324 internal to case 310. Each rein 468 partially wraps around one of the rollers 380.

From the roller 380 the neck 460 of the rein 468 enters the outer tube 420 through the window 428 adjacent the roller. The rein 468 then extends along the outer inner surfaces of the links 430. (For ease of illustration, this is not seen in FIGS. 45, 47 and 49.) The rein neck 460 extends out of the window 464 formed in the tube tip 456. The rein head 478, which extends out of the tool tip 456, is folded proximally and welded or otherwise secured to the adjacent exposed surface of the tip neck 460.

The inner tube 482 is disposed in the outer tube 420. Proximal to the outer tube windows 428, the steering reins 468 are disposed in the annular space between the outer tube 420 and the inner tube 482. When tool 280 is so assembled, the inner tube tip 488 is disposed in tip 456 integral with the outer tube 420. The window defined by inner tube edge is in registration with the window 464 associated with the outer tube 420.

While not seen, the proximal end of inner tube main section 484 projects proximally from the handpiece 282. The hub attached to the inner tube main section 484 is attached to the actuator 496. Actuator 496 is a device capable of appropriately displacing the inner tube 482 so the tool can perform the intended surgical procedure. In the described version of tool 280, the inner tube 482 is rotated within the outer tube 420. A suction is drawn through the inner tube 482. As a result of tips 456 and 488 having sharp edges or teeth around their windows, tissue drawn into the inner tube through windows is sheared away as a result of the rotation of the inner tube. One possible actuator is based on the Applicant's ESSX Handpiece. The structure of the ESSX Handpiece is the subject of U.S. Pat. No. 6,958,071 B2, SURGICAL TOOL SYSTEM, issued 25 Oct. 2005, the contents of which are explicitly incorporated herein by reference.

The surgical tool 280 of this invention is prepared for use by setting lock lever 402 to the bending enabled position in which relief surfaces 411 are the lever arm surfaces closest to the lock ring 364. Set screw 390 is set to adjust the position of the distal end of the outer tube 420 relative to handpiece 282. More particularly the outer tube 420 is set so that when the steering wheel 340 is in the center position, both reins 468 are slightly in tension. At this time, the longitudinal axes through the outer tube 420, links 430 and tube tip 456 are lineally aligned. Actuator 496 can be coupled to the tool 280 before or after these steps.

Surgical tool 280 of this invention is initially directed to the site to which the distal end of the tubes 420 and 482 are to be applied using the same technique used to start the placement of tool 110. Tubes 420 and 482 are bent by rotating the steering wheel 340. It is noted that it is possible to rotate steering wheel 340 even though the outer and inner tubes 420 and 482, respectively, extend through the steering wheel. This rotation is possible because steering wheel bores 346 and 348 function as void spaces for accommodating the tubes as the steering wheel 340 is rotated.

Figure 27:
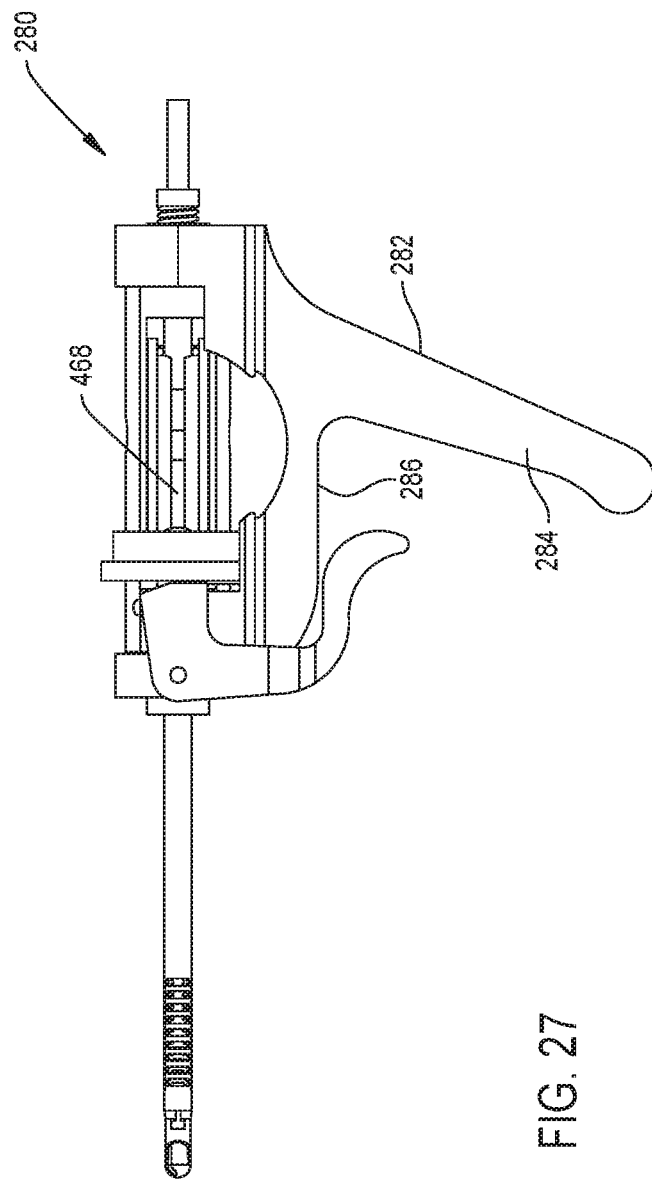
FIG. 27 is a side view of the first alternative surgical tool.

The rotation of the steering wheel 340 results in the simultaneous tensioning of one of the reins 468 and the slacking of the other rein 468. As a result of this tensioning/slacking of the reins an asymmetric load is placed on the tip 456 of the outer tube 420. This results in the tip 456 and, by extension, links 430 pivoting. More particularly, the tip/each link pivots about the axis that extends through the centers of the arms seated in the tip/link sockets. By the selectively movement of the arms, the outer tube 420 is bent in and out of the plane of the tool 280 as depicted in FIG. 27. Owing to the flexibility of neck 486 integral with inner tube 482, the neck bends with the bending of the outer tube links 430.

Links 430 may be subjected to side loading. This would be the imposition of a vertical force on the links 430 as seen in the plane of FIG. 27. The presence of the link legs 438 in the distally adjacent slots 452 prevent a link when subjected to side loading from moving out of engagement with the adjacent links. The leg in slot arrangement thus allows the adjacent links to pivot up and down in the plane of FIG. 50 but not in and out of the plane of FIG. 50. Each link can thus pivot around the axis around which the link is supposed to pivot while being restrained from pivotal movement in at least one second axis perpendicular to the axis around which the link is intended to pivot. This is especially useful prior to the seating of the inner tube 482 and attached neck 486 in the outer tube. Once the inner tube 482 is so positioned, the inner tube prevents the links 430 from moving out of engagement with each other.

After links 430 are bent so the outer and inner tubes 420 and 482, respectively, have the desired curvature, the practitioner locks the links into position relative to each other. This step is performed by pivoting the lock lever 402 so the arm lock surfaces 410 press against the distally directed face of the lock ring 364. Lock ring 364 is thus urged proximally rearwardly. The lock ring 364 abuts against and displaces the steering wheel 340 in the same direction. The rearward movement of the steering wheel 340 causes both reins 468 to urge outer tube tip 456 proximally. This displacement of the tool tip 456 compresses the links 430 against each other. More particularly, each link 430 is displaced proximally rearwardly so that the socket-defining surfaces 444 of the link are pressed against the outer surface of the arm of the proximally adjacent link. The socket-defining surfaces of the tool tip 456 are pressed against the arms 436 of the most distal link 430. Surfaces 444 of the proximal most link 430 are pressed against the arms 424 that extend forward from the outer tube 420. The pressing of these surfaces together thus inhibits the pivoting of the links 430 relative to each other. The pressing of the outer tube 420, the links 430 and the tool tip 456 together thus holds the tubes into the curved position desired by the practitioner.

Once the position of the tubes 420 and 482 are appropriately curved and the components are locked together, tool 280 is ready for use to perform the procedure. Actuator 496 is turned on to drive the inner tube 482 and associated cutting feature 490. The application of the actuated cutting feature 490 against the tissue against which the tool tips are positioned results in the performance of the desired procedure.

Once the procedure is performed, it may be necessary to straighten the tubes 420 and 482 to withdraw the tool 280 from the patient. If this is necessary, the lock lever 402 is moved from the lock state back to the bending enabled state. This frees the lock ring 364 and, by extension, steering wheel 340 for movement. This takes the reins 368 out of tensions so as the links 430 are no longer urged together. The steering wheel is then rotated to place the tubes in a position to facilitate either recurvature or straightening of the tube 420 and 482.

Tool 280 is bendable on a single axis. A benefit of tool 280 is that the tool includes more than a single shaft. Instead, the tool 280 in addition to the selectively bendable outer tube 420 includes the inner tube 482. Inner tube 482, in addition to bending with outer tube 420, is able to move relative to the inner tube. This means the tubes 420 and 482 can be provided with the complementary cutting features that, when moved relative to each other, perform a desired medical task or diagnostic function.

III. Second Alternative Embodiment

FIGS. 54-58 illustrate a second alternative surgical tool 502 of this invention. Tool 502 includes a handle 504 from which a bendable outer tube 670 extends distally forward. A tip 698, functionally if not structurally similar to tip 456, is located at the distal end of the outer tube. Previously described flexible inner tube 482 with tip 488 is rotatingly disposed in the outer tube 670. Two steering reins 710, functionally, steering cables, are disposed along the opposed sides of outer tube 670. Reins 710 are connected to a steering bar 564 that is pivotally mounted to the handle 504. Steering bar 564 is pivoted to selectively tension/slacken reins 710 in order to control the curvature, the bend, of outer tube 670. Steering bar 564 is further mounted to handle 504 to move longitudinally along the handle. A lock lever 648 is pivotally mounted to the handle adjacent steering bar 564. Lock lever 648 sets the position of the steering bar 564 along the handle 504. More specifically, the lock lever 648 sets the position of the steering bar between the steering enabled and locked positions.

As seen in FIGS. 59-62 tool handle 504 is generally in the form of a cylinder with sections having different outer diameters. There is a proximal section 506. Proximal section 506 is formed with two lobes 508 that extend outwardly from opposed sides of the outer surface of the handle 504, one lobe 508 identified in each of FIGS. 59 and 60. The handle 504 has a middle section 510 located immediately forward of proximal section 506. Handle middle section 510 has a diameter greater than that of proximal section 506. Forward of the middle section 510 the handle 504 has a distal section 512 has a diameter that is less than that of the proximal section 1008. Not identified is the tapered transition section between middle section 510 and the distal section 512.

Handle 504 is further formed to have two diametrically opposed and parallel flats 514. Flats 514 extend proximally from the distal end handle distal section 512, one flat 514 identified in each of FIGS. 59 and 60. The flats 514 extend the whole length of the distal section 512 to form the opposed sides of the distal section. Flats 514 extend proximally so to extend approximately the distalmost portion of the handle middle section 510. The flats 514 extend one-half the length of the handle middle section 510.

Figure 60:
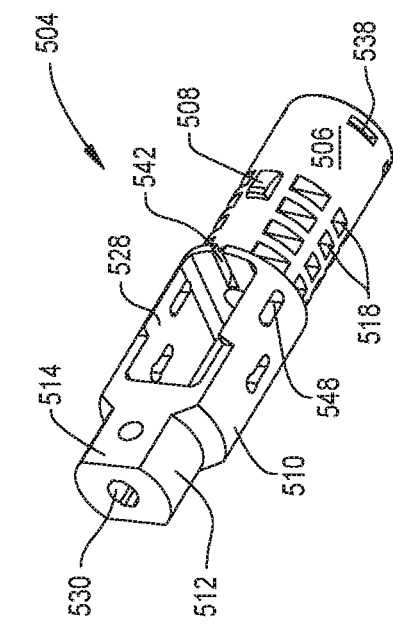
FIG. 60 is a second perspective view of the tool handle of FIG. 59.
Figure 59:
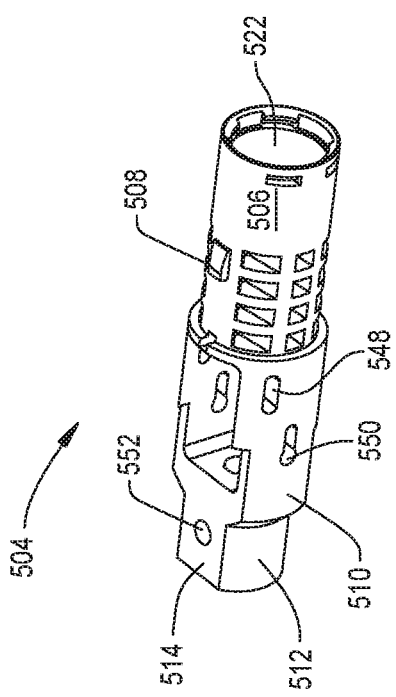
FIG. 59 is a first perspective view of the tool handle or tool body of the tool of FIG. 54.
Figure 62:
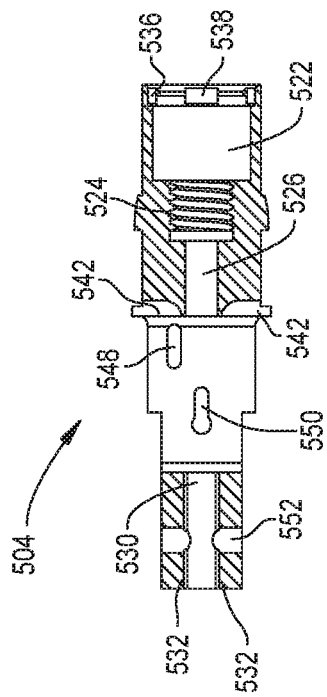
FIG. 62 is a cross sectional view of the tool handle of FIG. 59.
Figure 61:
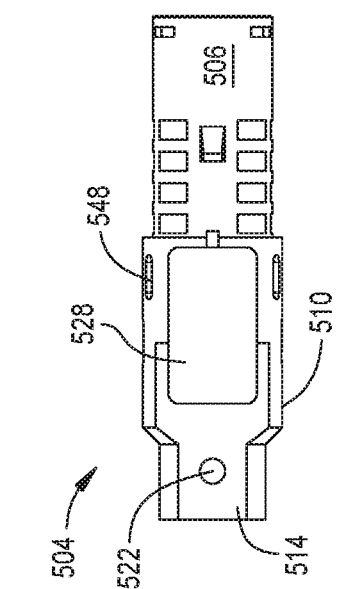
FIG. 61 is a plan view of the tool handle of FIG. 59.

The handle 504 is further formed so a number of recesses 518 extend inwardly from the outer surface of proximal section 506, two recesses identified in FIG. 60. Recesses 518 are present for manufacturing reasons only and are otherwise not relevant to this invention.

Handle 504 is formed to have bore 522 that extends distally forward from the proximal end of the handle. Bore 522 extends through approximately one-third to one-half of the proximal most portion of handle proximal section 506. A bore 524 extends forward from the distal end of bore 522. Bore 524 has a diameter less than that of bore 522. While not identified, the inner wall of handle that defines bore 524 is formed to be threaded. The distal end of bore 524 opens into a smooth walled bore 526. Bore 526 has a diameter less than that of bore 524. Bores 524 and 526 both extend through handle proximal section 504.

The distal end of bore 526 opens into a void 528 that extends laterally through handle middle section 510. The handle 504 is formed so void 528 extends side-to-side from one flat 514 to the opposed flat 514. Void 528 extends proximally from a location immediately distal to the proximal end of the middle section 510 and approximately through four-fifths of the overall length of the middle section. The distal end of void opens into a bore 530. Bore 530 extends through the distal part of the handle middle section 510 in which void 528 is not present and along the length of the handle distal section 512. Bore 530 opens at the distal end of the handle 504. Bores 522, 524, 526 and 530 are coaxial. Bores 526 and 530 have the same diameter. Handle 504 is further formed so that there are two longitudinally extending grooves 532 in the inner cylindrical wall of the handle that define bore 530. Grooves 532 thus are located radially outward from the outer perimeter of bore 530.

Figure 57:
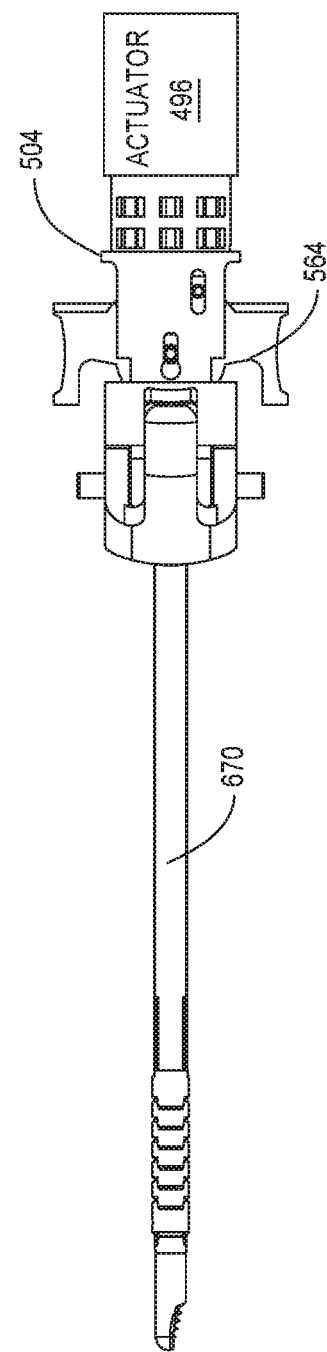
FIG. 57 is a bottom plan view of the tool of FIG. 54 with an actuator fitted over the proximal section of the tool handle.
Figure 58:
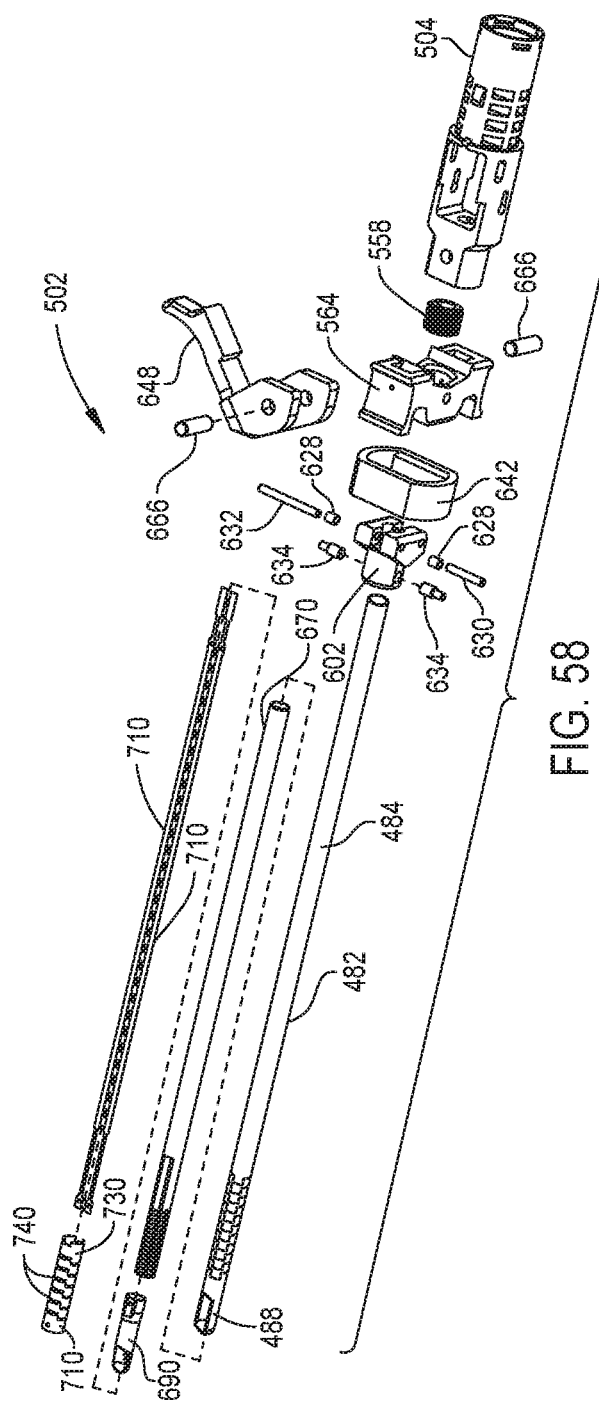
FIG. 58 is an exploded view of the tool of FIG. 54.

Handle 504 is further formed to have a groove 536 that extends circumferentially around the inner cylindrical wall of that defines bore 522. Groove 536 is located immediately distal to the proximal open end of bore 522. Side openings 538 extend outwardly from the base of groove 536 to the outer surface of handle proximal section 506. Lobes 508, groove 536 and side openings 538 are provided to facilitate the securing of actuator 496 to handle proximal section 506 as seen in FIG. 57. While not illustrated it should be appreciated that the actuator 496 includes features complementary to the features of the handle 504 to facilitate the releasable attachment of the actuator to tool 502. These features, both the handle features and actuator features, are not part of the present invention.

The handle is further formed to have two diametrically opposed slots 542. Each slot 542 extends outwardly from a location that is spaced from the location where bore 526 opens into void 528. Each slot 542 extends radially from this location adjacent the longitudinal axis of the handle to the outer perimeter of the handle middle section 510. Each slot 542 extends through the proximal portion of the handle that forms the step between the handle proximal and distal sections 506 and 510, respectively.

Handle middle section 510 is formed to have two pairs of openings. A first pair of openings is openings 548. Each opening 548 is oval shaped. Openings 548 open into the portion of void 528 that is not intersected by flats 514. The handle 504 is shaped so the major axes, the longitudinal axes, of openings 548 are parallel to the longitudinal axis through the handle. Openings 548 are not diametrically opposed to each other relative to the longitudinal axis of the handle. Instead the longitudinal axes of the openings 548 are located on a plane that is spaced away from the longitudinal axis of the handle. The second pair of openings are the openings 550. Openings 550 are located forward of openings 548 and open into the distal portion of void 528, the portion of the void that intersects flats 514. Each opening 550 can generally be described as being keyhole shaped. The major axes of openings 550 are parallel to the major axes of openings 548. Handle 504 is further formed so that the wide diameter circular portions of the openings 550 are the most distal portions of the openings 550. The handle is further formed so that openings are diametrically opposed to each other relative to the longitudinal axis through the handle 504.

A bore 552 extends side-to-side through handle distal section 512. The bore 552 extends between flats 514. Bore 552 is perpendicular to and intersects bore 530. Bore 552 also intersects grooves 532 integral with bore 530. It should be understood that the axis of bore 552 is perpendicular to the major axes of openings 548 and 550.

Figure 63:
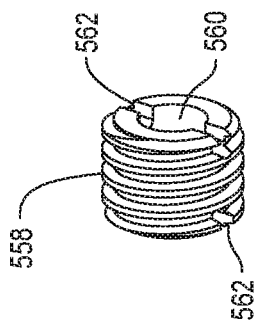
FIG. 63 is a perspective view of the set screw internal to the tool of FIG. 54.

A set ring 558, seen best in FIG. 63, is disposed in the handle proximal section 506. The set ring 558 is sleeve like in shape with a threaded outer surface (threading not identified). A bore 560 extends axially through the ring 558. The outer faces of the set ring are formed to have a slot 562. Slot 562, which intersects bore 560 is dimensioned to receive the blade of a screwdriver. Both ends of the set ring 558 are formed with slots 562 to facilitate ease of assembly of tool 502. When the tool is assembled, set ring 558 is threaded into handle bore 524.

Steering bar 564, as seen best in FIGS. 64-67, is a single piece component. The steering bar 564 is dimensioned to slip fit in void 528 internal to handle middle section 510. Steering bar 564 is formed have a base 566. Base 556 has a flat distally directed face 568. Two side surfaces 570 curve away from the opposed ends of face 568. More specifically, side surfaces 570 are the surfaces of the base that extend outwardly away from handle 504. As the side surfaces 570 extend away from face 568, the surfaces 570 curve proximally rearward. Steering bar 564 has two arms 572 that, relative to the proximal to distal longitudinal axis through base 566, are diametrically opposed to each other. Each arm 572 extends outwardly from the end of an adjacent base side surface 570. Arms 572 thus project outwardly from opposed sides of void 528 on opposed sides of the handle 504. A tab 574 extends distally forward from the free end of each arm 572. Steering bar 564 is shaped so that when the bar is in the neutral position, the axis along which arms 572 is perpendicular to the longitudinal axis of the handle 504 and each tab 574 extends on an axis that is parallel to the longitudinal axis of the handle 504.

The steering bar 564 is further formed so as to have an opening 576 that extends proximally rearward from face 568. Opening 576 is oval in shape. The curved ends of opening 576 extend through the ends of surfaces 560 immediately adjacent face 568. Opening 576 opens into a void 578 formed within bar base 566. Void 578 is generally oval in shape such that the major and minor axes of void 578 are aligned with, respectfully, the major and minor axes of opening 576. Steering bar 564 is formed so that the width and length of void 578 are greater than the associated dimensions of opening 576. Void 578 extends to the proximal end of bar base 566. Two holes 580 extend inwardly from the opposed sides of base 566 into void 578. Holes 580 are coaxial. The axis on which holes 580 are centered is collinear with the minor axis of void 578 in a cross-sectional plane perpendicular to the longitudinal axis through handle 504.

Each arm 572 of steering bar 564 is formed with an interior channel 584 that extends proximally-to-distally through the arm. The proximal opening into each channel 584 is located immediately outwardly of the adjacent proximal opening into void 578. The distal opening into the channel 584 is located at the distal end of the arm 572, adjacent where the associated tab 574 is extends distally forward of the arm. The proximal opening into each channel 584 is longer in width than the width of the complementary distal opening. Here "width" is understood to be along the vertical axes of the channels 584 seen in FIG. 67. Internal to the steering bar 564 each channel 584 is defined by two inner surfaces of the arm. One inner surface, surface 586 is curved such that extending proximally to distally, the surface curves outwardly. The opposed inner surface that defines a channel 584, surface 588, is planar.

Steering bar 564 is further formed to have two additional bores 589. (One bore 589 identified in each of FIGS. 64 and 67.) Bores 589 are diametrically opposed to each other relative to the longitudinal axis through the bar base 566. Each bore 589 extends inwardly from an outer surface of a tab 574, through the adjacent arm 572 and opens into void 578. Each bore 589 intersects the channel 584 formed in the arm through which the bore extends. The steering bar 564 is further formed so that as each bore 589 extends inwardly towards the bar base 566, the bore extends distally forward.

A tensioner 602, seen in detail in FIGS. 68-71, is seated in void 578 internal to the steering bar 564. Tensioner 602 has a generally cylindrical stem 604. Opposed flats 606 interrupt the curved profile of stem 604, only one flat 606 seen in FIG. 68. The stem is the portion of the tensioner that seats in steering bar void 578. Collectively, the steering bar 564 and the diameter of the stem is less than the length along the major axis of void 578. Proximal to stem 604, the tensioner 602 has a head 608. The most distal portion of head 608 is a crown 610 with a convex shape. The crown 610 is centered along an axis that is perpendicular to the longitudinal axes through flats 606. Two opposed surfaces 612 extend outwardly and proximally from the opposed proximal ends of the crown. Proximal to surfaces 612, head 608 is generally in the form of a rectangular block.

A bore 616 extends axially through tensioner 602. Bore 616 starts at the distal end of stem 604 and extends through both the stem and head 608. Internal to the tensioner 602 there are also two grooves 618 that extend longitudinally through the tensioner. Grooves 618 extend radially outwardly from the inner cylindrical wall internal to the tension that defines bore 616. The grooves 618 are diametrically opposed to each other relative to the proximal-to-distal longitudinal axis through the bore 616. Each groove 618 is radially spaced 90° from the flats 606 on the outside of the stem. Two coaxial bores 620, one identified in each of FIGS. 68 and 71, extend laterally into stem 604. Each bore 620 opens inwardly from the base of one of the flats 606. The axis along which bores 620 are centered is perpendicular to the longitudinal axis through bore 616. Each bore 620 opens into bore 616.

The head 608 of tensioner 602 is formed to have an elongated slot 624. Slot 624 extends inwardly from the proximally directed face of head 608. The slot 624 extends side-to-side across the head 608. More specifically, slot 624 extends along a line that is in line with the axis that bisects grooves 618. Tensioner head 608 is further formed to have two bores 626. Each bore 626 extends along an axis that is perpendicular to the longitudinal axis along slot 624. Bores 626 intersect slot 624. The tensioner 602 is further formed so that bores 626 are located inwardly of the opposed surfaces of head 608 into which the opposed ends of slot 624 open.

Figure 68:
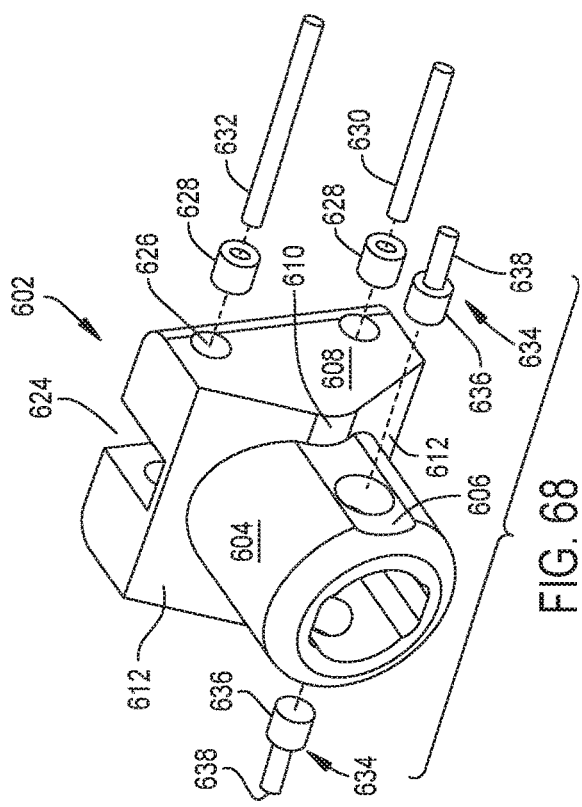
FIG. 68 is an exploded view of the rein tensioner internal to the tool of FIG. 54 and some of the components attached to the tensioner.
Figure 71:
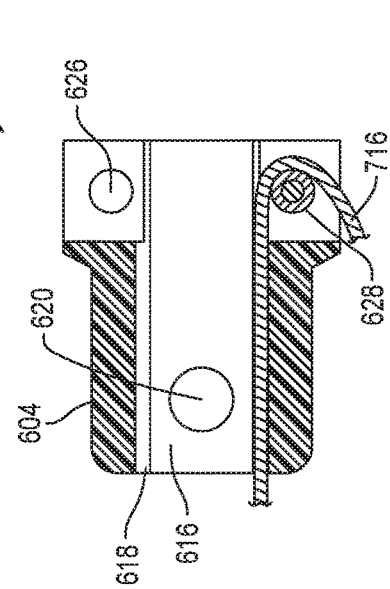
FIG. 71 is a cross sectional view of the tensioner and one of the steering reins threaded in the cable.
Figure 70:
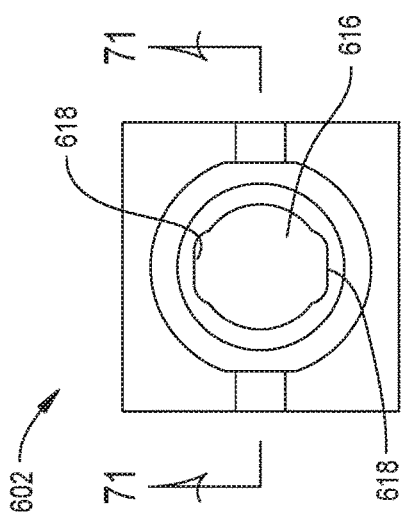
FIG. 70 is a plan view of the distally directed end of the tensioner.

Two rollers 628, seen best in FIG. 68, one seen in FIG. 71, are rotatably mounted in slot 624. Each roller 628 is held in place by a pin. Specifically, a first pin, pin 630, extends through one of the bores 626 and the portion of slot 624 that intersects the bore. A roller 628 is rotatably mounted over the portion of pin 630 that extends through slot 624. A second pin, pin 632 extends through the second bore 626. The second roller 628 is rotatably mounted to the portion of pin 632 that extends through slot 624. Pins 630 and 632 are of the same diameter. Pin 630 is however, smaller in length than pin 632. Specifically pin 630 does not project out of the tensioner head 608. Pin 632 is longer than pin 630 and extends out of the tensioner head. The diameter of pins 630 and 632 is such that the ends of pins 632 are able to slide in handle openings 548.

Figure 64:
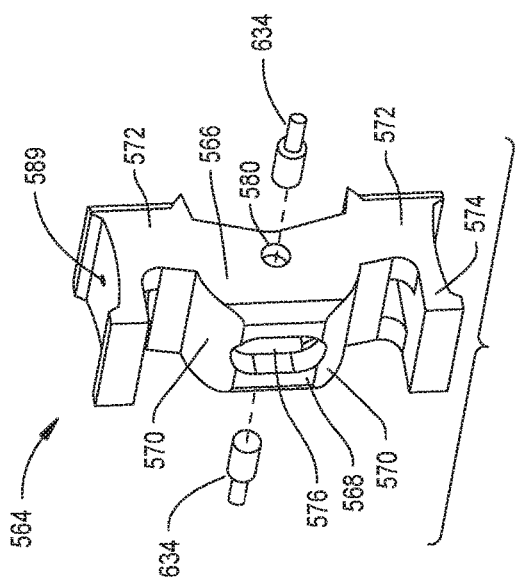
FIG. 64 is an exploded view of the steering bar of the tool of FIG. 54 and the retaining pins that are seated in the steering bar.
Figure 66:
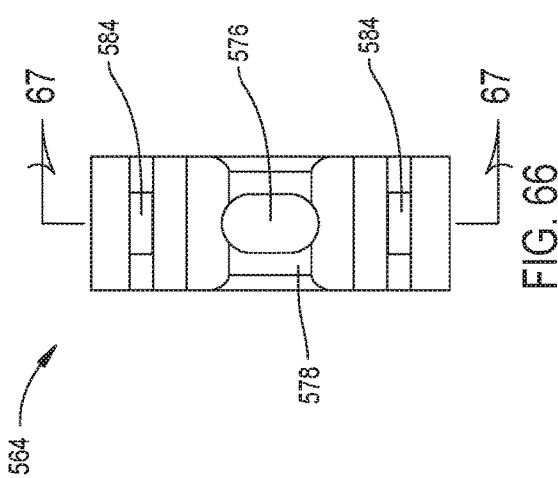
FIG. 66 is a plan view of the proximally directed face of the steering bar.
Figure 69:
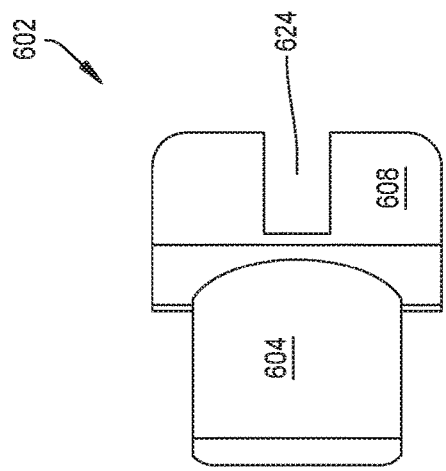
FIG. 69 is a side plan view of the rain tensioner.

Two pins 634 best seen in FIGS. 64 and 68, hold both the steering bar 564 and the tensioner 602 to the tool handle 504. Each pin 634 has a cylindrical head 636 from which a cylindrical shaft 638 extends. Pin heads 636 are dimensioned to seat in bores 620 integral with tensioner stem 604. Pin shafts 638 are dimensioned to seat and extend outwardly from the holes 580 formed in base 566 of the steering bar 564. The components forming tool 502 are further constructed so that the pin heads 636 can extend through the wide diameter distal ends of openings 550 formed in handle middle section 510. Pin shafts 638 are able to slide in the narrow width elongate portions of openings 550.

When tool 502 is assembled, the tensioner 602 is positioned so that the tension stem 604 is seated in the void 578 internal to the steering bar 564. More particularly, the steering bar 564 and tensioner 602 are positioned so that bores 620 integral with the tensioner are in registration with holes 580 formed in the steering bar. Tensioner head 608 is disposed against the proximal end of the base 566 of the steering bar 564. Pin 630 is used to seat one of rollers 628 in the slot 624 internal to the tensioner 602. The sub assembly is placed in void 528 internal to the handle 504. As discussed below, the steering reins 710 may then be threaded through the tensioner 602 and steering bar 564 and secured to the steering bar. Pins 634 are inserted in the wide diameter distal ends of openings 550 so that each pin head 636 seats in a separate one of the tensioner bores 620 and the adjacent bore 589 internal to the steering bar 564. Each pin shaft 638 extends through away the steering bar. Pin shafts 638 are dimensioned to seat and slide in the narrow with elongated portions of the handle openings 550. The second roller 628 is then rotatably mounted in tensioner slot 624 with pin 632. More particularly, pin 632 is slipped into position through handle openings 548 and the bores 626 formed in tensioner head 608. Owing to the dimensioning of the components forming the tool 502, the opposed ends of pin 632 seat in the opposed openings 548 formed in the handle middle section 510.

Thus, owing to the arrangement and dimensioning of the above components, pins 634 are able to translate in handle openings 550. By extension, this means that both the steering bar 564 and tensioner 602 will engage in simultaneous translation motion in the handle void 528 between the opposed proximal and distal ends of void 528. Steering bar 564 is able to pivot around the pins 634. However, pin 632 extends from the tensioner into handle openings 548. This seating of pin 632 in the handle openings 548, while allowing the translational motion of the tensioner 602, prevents the tensioner from pivoting.

Figure 73:
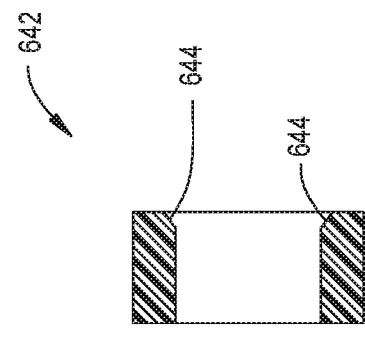
FIG. 73 is a cross sectional of the lock ring of FIG. 72.
Figure 72:
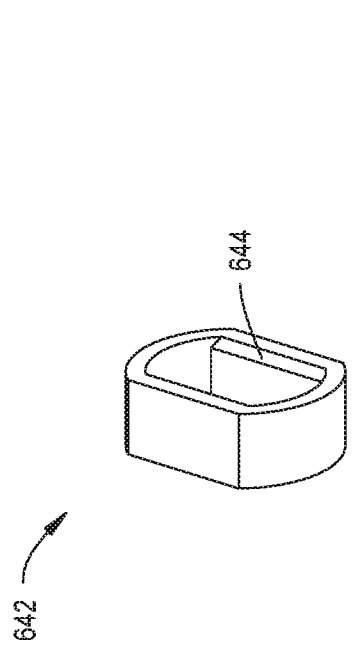
FIG. 72 is a perspective view of the lock ring of the tool of FIG. 54.

FIGS. 72 and 73 illustrate a lock ring 642 that is slidably mounted to the handle 504 forward of the steering bar 564. Lock ring 642 is approximately oval in shape. The curved portions of the ring 642 each subtend an arc of approximately 135°. The lock ring 642 has an internal width of between the opposed inner faces of the straight portions of the ring is sufficient to allow straight portions of the ring slip move over the flats 514 that extend proximally from the front end of handle 504. The lock ring 642 is further formed so that the straight portions of the ring are formed with opposed curved surfaces 644. As each surface 644 extends distally from the proximally directed end of the ring 642, the surface curves inwardly, towards the center of the ring so that extending distally from the proximal end of the ring, the thickness of the straight section of the ring in which the taper is formed increases. Surfaces 644 have a radius of curvature that is equal to or slightly greater than the radius of curvature of steering bar side surfaces 570.

When tool 502 is assembled, the lock ring 642 is slip fit over handle flats 514. More particularly, the lock ring 642 is positioned over the portion of flats 514 that extend to the handle middle section 510. Each tapered surface 644 faces an adjacent one of the curved side surfaces 560 of steering bar 564.

Figure 75:
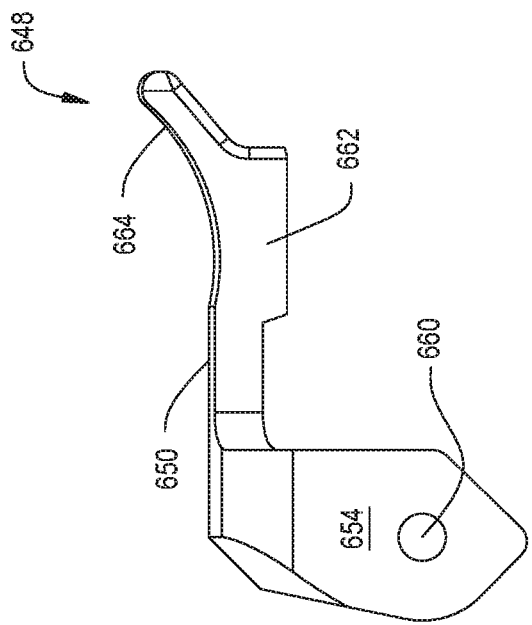
FIG. 75 is a side plan view of the lock lever.
Figure 74:
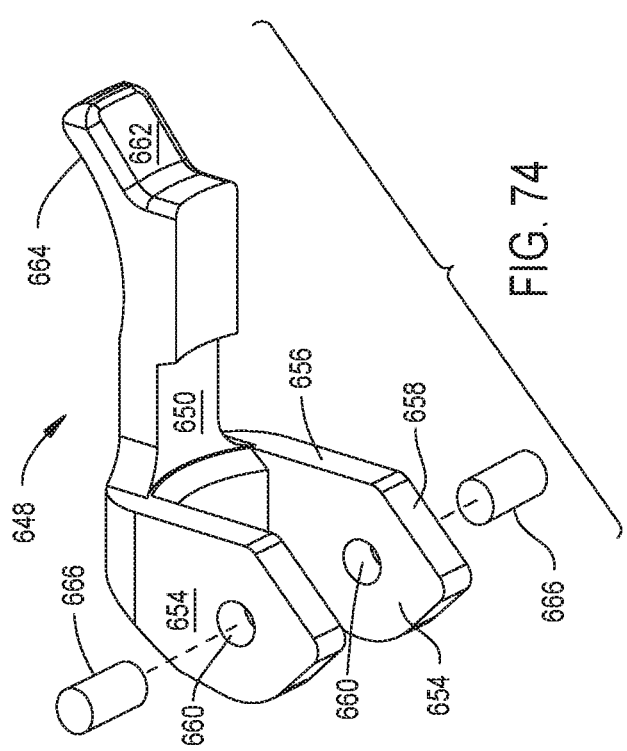
FIG. 74 is an exploded view of the lock lever of the tool of FIG. 54 and the pins attached to the lock lever.

The lock lever 648, as seen in FIGS. 74 and 75, includes a core 650 that is generally rectangular in shape. Two legs 654 extend outwardly and downwardly from the dist. The lock lever 648 is dimensioned so that legs 654 can seat over the opposed handle flats 514. Each leg 654 is formed with a lock surface 656 and a relief surface 658, one of each identified in FIG. 74, both of which are generally proximally directed. The lock surface 656 is the surface of the leg 654 closest to core 650. Lock surfaces 656 are located on a plane that is perpendicular to the plane in which the lever core 650 is disposed. Each relief surface 658 is located immediately below the associated lock surface 656. Specifically, extending downwardly from the lock surface 656 the associated relief surface 658 extends proximally forward. Each lock leg 654 is further formed with a though hole 660 that extends between the opposed outer and inner faces of the leg. Leg holes 660 are coaxial.

Lock lever 648 is further formed to have a pad 662. Pad 662 extends downwardly from the proximal end of core 650. A finger/thumb tab 664 flares upwardly from the proximal end of core 650.

When tool 502 is assembled, the lock lever 648 is positioned so that legs 654 seat over the portion of the flats 514 that extend along the handle distal section 512 and pad 662 is directed towards the handle middle section 510. Pins 666, seen best in FIG. 74, pivotally hold the lock lever 648 to the handle 504. Each pin 666 extends through a separate one of the leg holes 660 into one end of the underlying bore 552 internal to the handle distal section. Owing to how the components are dimensioned, when the lever is in the locked position, the lever pad 662 abuts the handle middle section 510 at position proximal to where lock ring 642 is located.

Figure 78:
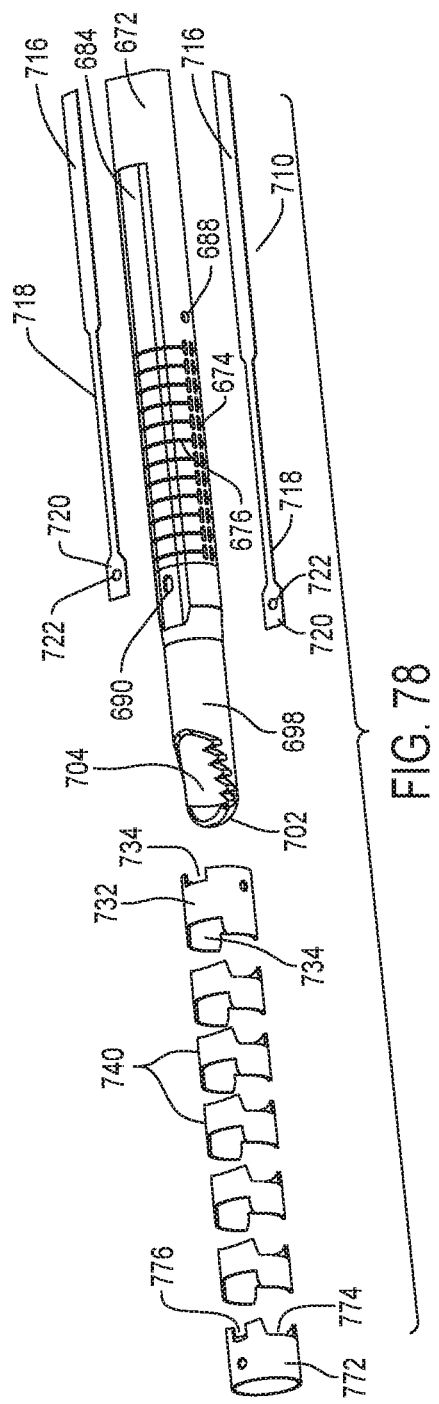
FIG. 78 is an exploded view of the assembly present at the outer shaft of FIG. 76.
Figure 79:
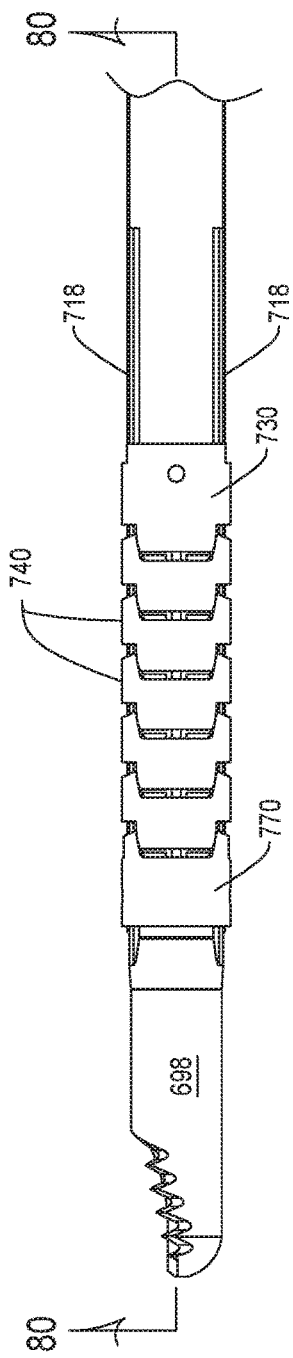
FIG. 79 is a side view of the distal end of the outer shaft of FIG. 76.

A basic understanding of the structure of outer tube 670 is obtained in part by reference to FIGS. 76-78. Outer tube is formed from stainless steel and has a wall thickness of approximately 0.25 mm. The outer tube 670 has a rigid trunk 672 that is the proximal most portion of the tube. Typically, the trunk 672 has a length that is 70 to 80% of the overall length of the tube. Formed integrally with and immediately forward of the trunk 672, outer tube 670 has a flexible neck 674. Neck 674 is formed by providing the workpiece forming the tube with a number of slots 676, best seen in FIG. 80. Each slot 676 in the outer tube of FIG. 80 has a main section 678 that extends arcuately around the tube. Each slot main section 678 subtends an arc of approximately 100°. An end cut 680 is located at each end of the slot mean section 678. Each end cut 680 is centered on an axis that is perpendicular to the plane of the slot main section.

Figure 80:
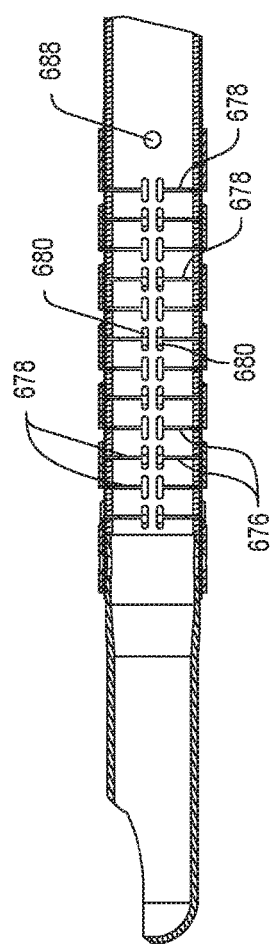
FIG. 80 is a cross sectional view of the outer shaft taken along line 80-80 of FIG. 76.

Slots 676 are further formed so that one slot is, relative to the proximal-to-distal longitudinal axis through the tube symmetric with respect to a second slot 676. Since the slots do not extend 180° around the tube, each end cut 680 is arcuately spaced from the adjacent end cut 680 of the symmetrically opposed slots 676. The slots 676 are further arranged so that that each end cut 680 is longitudinally aligned with the end cut of the proximally and/or distally adjacent slot. Owing to this arrangement of the slots it should be understood that neck 674 is formed with two arcuate sections that extend longitudinally along the neck that are slot free. Owing to this arrangement of the slots the neck 674 of FIG. 80 is able to flex up and down in the plane of the Figure. However, owing to the presence of the slot-free sections of the neck, the neck 674 is constrained from movement in and out of the plane of FIG. 80.

Outer tube 670 is further formed to have two gutters 684 that extend inwardly from the outer surface of the tube, one channel identified in FIG. 78. Gutters 684 are diametrically opposed to each other around the proximal-to-distal longitudinal axis through the tube 670. Each gutter 684 extends proximally forward from a location in the tube trunk 672 approximately 2 to 4 cm proximal to the neck 674. The channels extend across tube neck 674. Each gutter 684 terminates immediately forward of the neck 674. The outer tube 670 also has two through holes 688, one seen in FIG. 78. Each through hole 688 is formed in tube trunk 672 immediately proximal of one of the slot free sections of flexible neck 674. Holes 688 are coaxial. Forward of neck 674 the outer tube 670 has two additional through holes 690. Each through hole 690 extends inwardly from the base of one of the channels and more particularly the portion of the channel located immediately forward of tube neck 674. Holes 690 are coaxial. The axis around which holes 690 are aligned in perpendicular to the axis around which holes 688 are aligned.

Tube tip 698 is formed integrally with the rest of outer tube 670. The tube tip 698 has an outer diameter less than of the tube trunk 672 and neck 674. A transaction ring 685 is the portion of the tube that connects the tip 698 to the distal end of neck 674. Transition ring 685 is tapered such that as the ring extends distally from neck 674, at least the outer diameter of the ring decreases. Tube tip 698 is formed with a head 702 similar if not identical in shape to tube tip 698. The tube tip 698 is formed with a cutout 704 similar if not identical to cutout 466 of tube tip 456.

Each steering rein 710, seen initially in FIGS. 76, and 78 is in the form of an elongated strip of flexible metal. At the proximal end, each steering rein 710 is formed to have a foot 712. Forward of the foot 712 the steering rein has a leg 714. Leg 714 has a side-to-side with less than the width of the foot 712. Forward of leg 714, the rein 710 has a trunk 716. The trunk 716 has a width greater than that of the leg. The width of the trunk 716 is such that the trunk can seat in one of the gutters 684 formed in the outer tube 670. Trunk 716 occupies more than one-half of the overall length of the rein 710. A neck 718 extends forward from the trunk 716. Neck 718 has a width less than that of trunk 716. A head 720 is contiguous with and located immediately forward of the neck 718. The head 720 has a width greater than the width of neck 718.

Each steering rein 710 is formed to have two openings. Each opening extends between the opposed inner and outwardly directed faces of the rein. An opening 717 is located in the trunk 716 immediately forward of the distal end of the trunk. An opening 722 is located in the head 720.

When tool 502 is assembled, each rein head 720 is secured in the distal portion of one of the tube gutters 684, the portion of the channel from which hole 690 extends. The rein 710 extends proximally through the gutter 684. The rein 710 then extends proximally over outer tube trunk 672. The proximal portion of the outer tube trunk, it is understood extends through handle bore 530, opening 576 into the steering bar 564 and tensioner bore 616. The steering reins 710 extend longitudinally proximally with the tube trunk 672. More particularly, each steering rein is seated in one of the grooves 532 contiguous with handle bore 530 and one of the grooves 618 contiguous with tensioner bore 616.

Figure 67:
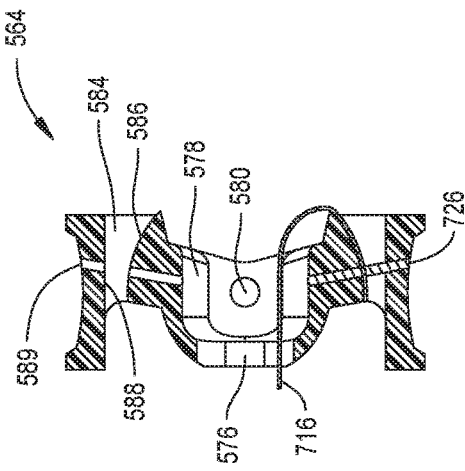
FIG. 67 is a cross sectional view of the steering bar taken along line 67-67 of FIG. 66 as well as one of the steering reins disposed in the bar.

The proximal end of the rein trunk 716 is looped around the roller 628 adjacent the tensioner groove 618 through which the rein 710 extends, one seen in FIG. 71. From the roller 628, the rein extends distally through the adjacent channel 584 formed in the steering bar. The rein 710, one seen in cross section in FIG. 67, is disposed against the curved surface 586 internal to the arm that defines the channel 584. A pin 726 is seated in one of the bores 589 formed in the steering bar and extends through the opening 717 formed in the proximal end of the rein trunk 716. Pins 726 thus hold the reins 710 to steering bar 564.

During the process of assembling the components forming tool 502 as described above, it is necessary to thread the rein 710 through the channel 584 in the steering bar 564 and position the rein so pin 726 can extend through rein opening 717. A tool, such as pliers, is used to grasp the rein foot 712 so the rein can be so positioned. Rein feet 712 and legs 714 do not have any other function than being useful for the above described tool assembly. Accordingly, after the tool is so assembled, the rein feet 712 and legs 714 are removed.

Collars 730, 740 and 770 are disposed over outer tube 670 and the distal portion of the reins 710. Specifically, there is a proximal collar 730 that is secured to the tube trunk 672 immediately proximal to the tube neck 674. Plural shifting collars 740 are disposed over the tube neck 674. A distal collar 770 is secured over the tube 670 at a location forward of the most forward pair of slots 676.

Figure 81:
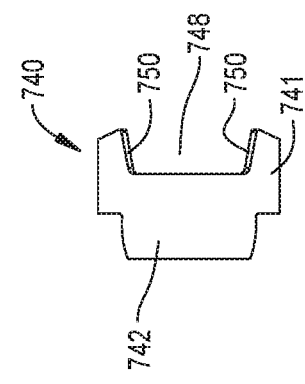
FIG. 81 is a plan view of one of the links integral with shaft of FIG. 76.
Figure 83:
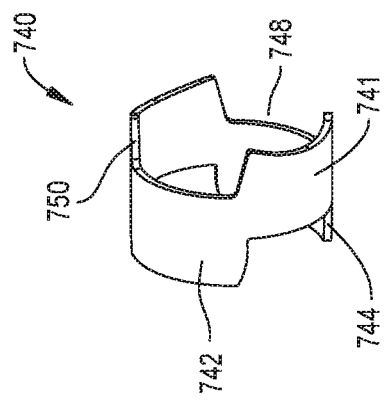
FIG. 83 is a perspective view of the link wherein the distally directed face of the link is visible.
Figure 82:
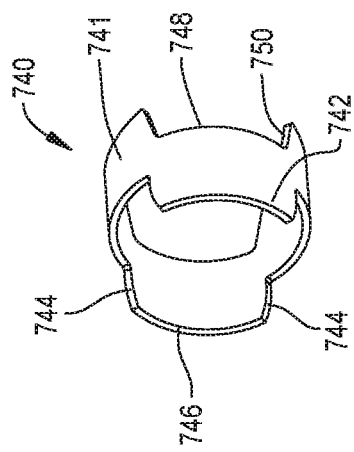
FIG. 82 is perspective view of the link wherein the proximally directed face of the link is visible.
Figure 65:
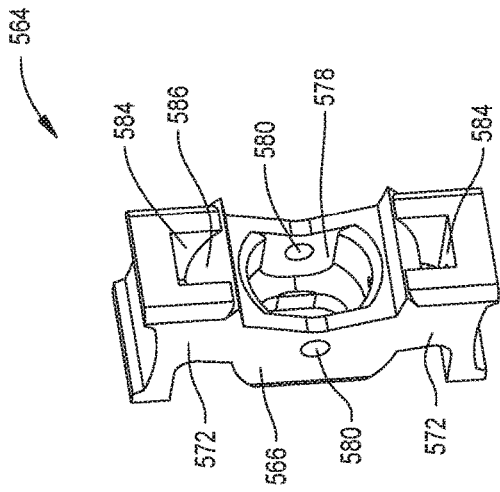
FIG. 65 is a perspective view of the steering bar of FIG. 64 wherein the distally directed face of the bar is seen.

An understanding of the structure of collars 730, 740 and 770 begins with the understanding of the structure of one of the shifting collars 740 seen best in FIGS. 81-83. Each shifting collar 740 has a tube-like base 741. Two tabs 742 extend, protrude, distally forward from base 741. Tabs 742 are diametrically opposed to each other relative to the proximal-to-distal longitudinal axis through the collar 740. Each tab 742 is formed to have a pair of opposed curved side surfaces 744, seen in FIG. 82. Each side surface 744 extends distally forward from the front end, the distal end of the base 741. As the side surface 744 extends forward, the surface curves towards the opposed side surface 744. At the distal end of the tab, a leading surface 746 extends between the opposed distal ends of the side surfaces 744.

Each shifting restraining collar 740 is further formed to have two diametrically opposed notches 748. Notches 748 extend distally forward from the proximal end of the base 721. Each notch 748 is aligned with a separate one of the tabs 742. The sides of each notch 748 are defined by opposed side surfaces 750, seen best in FIG. 81. Side surfaces 750 are straight and tapered. Thus, extending distally forward from the proximal end of the base 741 each side surface 750 extends inwardly towards the opposed side surface 750. Each shifting collar 740 is further formed so that the proximal portion of each notch 748 is wide enough to accept the distal portion of tab 742 of a proximally adjacent collar 730 or 740. The profile of the collar tabs and notches is however such that as a tab extends into a notch the tab side surfaces 744 abut the adjacent notch-defining side surfaces 750 prior to the tab leading surface 746 abutting the surface of the base 741 that defines the distally located base of the notch 748. Thus, when a tab is fully seated in a notch, there is a separation between the tab leading surface 746 and the base of the notch in which the tab is seated as seen in FIG. 77.

From FIG. 77 it can be seen that the proximal restraining collar 730 is formed with a base 732 that is longer in length than the base 741 of the shifting collars 740. Two notches 734, one seen in FIG. 77, extend forward from the proximal end of base 732. Notches 734 are smaller in width than notches 748. Also notches 734 have side defining walls that are parallel, not angled relative to the proximal to distal longitudinal axis through the collar 730. Two diametrically opposed tabs 736 extend forward from collar base 732, one tab 736 seen in FIG. 77. Tabs 736 are geometrically identical to shifting collar tabs 742. The proximal collar 730 is further formed to have two diametrically opposed through holes 738 that extend through the base 732. Through holes 738 are coaxial. The axis around which through holes 738 are centered is perpendicular to the line that extends between notches 734.

Distal collar 770 has a base 772 that is generally the length of base 732 of the proximal collar 730. The distal collar 770 is formed with a first pair of diametrically opposed notches, notches 774, one seen in FIG. 77, that extend distally forward from the proximal end of the base 732. Notches 774 are geometrically identical to shifting collar notches 748.

The distal collar 770 also includes a second pair of diametrically opposed notches, notches 776, one notch 776 shown. Notches 776, like notches 774, extend forward from the proximal end of collar base 732. Notches 776 are shorter in width than notches 774. The line that extends between the center of notches 776 is perpendicular to the line that extends between the center of notches 774. Distal collar 770 is further formed to have two coaxial through holes 778, one hole shown. Each through hole 778 is longitudinally aligned and located distally forward of a separate one of the notches 776.

When tool 502 is assembled, proximal collar 730 is the first collar fitted over the outer tube 670 and reins 710. Proximal collar 730 is welded or otherwise secured to the tube trunk 672 so that the collar notches 734 are disposed over tube gutter 684 and the rein disposed in the tube gutter. The collar holes 738 are placed in registration with tube holes 688 to facilitate the securing of the collar 730 to the tube in the proper location and orientation relative to the tube.

The plural shifting collars 740 are slip fitted over the tube neck 670 and the underlying sections of the reins 710. The proximal most shifting collar 740 is positioned so that the proximal collar tabs 736 seat in the notches 748 of the shifting collar 740. The remaining shifting collars 740 are arranged so that the tabs 742 integral with the proximal shifting collar 740 are seated in the notches 748 integral with the distally adjacent shifting collars 740. Notches 748 are thus functionally similar to the previously described sockets 236 and 450.

Distal collar 770 is slip fitted over the slot free distal portion of the tube neck 674. The distal collar 770 is positioned so the tabs 742 integral with the distal most shifting collar 740 seat in the notches 774 integral with the distal collar 770. This results in distal collar notches 776 going into registration over the portions of rein necks 718 located immediately forward of the distal most shifting collar 770. Rein heads 720 are disposed below the body of distal collar 770. Once the distal collar 770 is in position, the rein heads 720 are secured to the inner cylindrical surface of the distal collar. Outer tube holes 690, rein openings 722 and collar holes 778 are provided to secure the temporary holding of the reins 710 to the distal collar 770 in order to facilitate the more permanent attachment of the reins 710 to the collar 770.

The components forming tool 502 are arranged so that the proximal end of outer tube trunk 672 seats in handle bore 524. As part of the initial set up of the tool the lock lever 648 is placed in the bending enabled position, the position depicted in FIG. 54. When the lock lever 648 is in the bending position, the lever relief surfaces 658 are the surfaces of the tool closest to the lock ring 642. As part of the process of readying tool 502 for use, set screw is threaded in the handle bore 524 so the distal end of the screw presses against the outer tube trunk 672. The distal ends of steering reins 710 are attached to the outer tube 670. Accordingly, distal movement of the outer tube places results in a like motion of the reins 710. Reins 710 are attached to steering bar 564. Accordingly, the distal movement of the reins causes a like distal movement of the steering bar 564. Since the tensioner 602 is attached to the steering bar to engage in longitudinal movement with the steering bar, the tensioner undergoes a like distal movement. The distal movement of the steering bar forces the bar against the lock collar and the lock collar against the lock lever relief surfaces 658. The blocking of the further distal movement of the steering bar 564 means that the continued distal movement of the outer tube and, the distal end of the reins 710 places both reins in tension. Reins 710 thus pull the distal end of the outer tube proximally rearward. This results in locking collars 730, 740 and 770 being pressed against each other. At this time though, the tension imposed on the reins is relatively small. By extension this means that the compressive force that holds the locking collars 730, 740 and 770 together is likewise relatively small. This means while collars 730, 740 and 770 abut, each collar is able to pivot relative to the proximally adjacent collar.

As part of the process of assembling the tool 502, the inner tube 482 is slid distally through the handle 504 to seat in the outer tube 670. When tubes 482 and 670 are so positioned, inner tube flexible neck 486 is seated within outer tube flexible neck 674. Inner tube tip 488 is seated in outer tube tip 698. While not illustrated it should be understood that the proximal end of the inner tube 482 is disposed in handle bore 526. Also not illustrated and not part of the present invention are the components integral with the inner tube 482 and actuator 496 that releasably hold the inner tube to the actuator. Again, in many versions of the invention, actuator 496 rotates the inner tube. This rotation results in a like rotation of inner tube tip 482 relative to outer tube tip 698.

Once tool 502 is so configured, the tool is ready for use. By manipulating handle 504, inner and outer tubes 482 and 670 are inserted in the portal that lead to the site to which the distal end of the tool, inner and outer tube tips 488 and 690, respectively, are to be applied.

As part of the process of positioning the distal end of tool 502, it may be desirable to curve or bend the tool. This bending is performed by the pivoting of the steering bar 564. To bend tool 502 so the tips 488 and 690 are directed downwardly in FIG. 57, steering bar 564 is pivoted so the downwardly directed arm 572 is pivoted distally forward. This pivoting of the steering bar pulls the portion of the steering rein 710 attached to the arm forward. Most of the rein 710, it is recalled, extends forward from the associated roller 628 to the distal end of the outer tube 670, the portion of the tube located forward of flexible neck 674. The pulling forward of the portion of the rein 710 pin to the steering bar 564 thus results in a proximal, rearward displacement of the distal end of the rein, the end of the rein connected to the distal end of the outer tube 670. The tension imposed on this rein is thus increased.

The forward pivoting of the bottom located steering arm 572 in the tool as depicted in FIG. 57, results in the simultaneously rearwardly directed pivoting of the top located steering arm 572. This results in the like rearward movement of the portion of the rein 710 pinned to the top located arm. This rein displacement slackens, reduces the tension of the portion of this rein 710 that extend between the associated roller 628 and the distal end of the of the outer tube 670.

Figure 84:
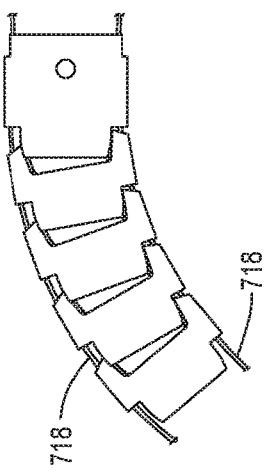
FIG. 84 is a side view of depicting how, as a result of the tensioning of the reins, the links develop a bend or a curve.

This simultaneous tensioning of the bottom located rein 710 and slackening of the top located rein 710 causes the reins to place an asymmetric force on the distal end of the outer tube 670. This force, which is proximally directed, to the right in FIG. 57, is imposed on the portion of the rein below the longitudinal axis through the tube 670. As a result, the tube flexible neck 674 will tend to flex downwardly. As mentioned above, while at this time, collars 730, 740 and 770 abut, the collars are free to pivot relative to each other. Thus, the collars when the tool is in this state do not opposed the flexing of the neck 674. The neck then flexes downwardly to provide the inner and outer tubes 482 and 670, respectively, with desired curvature as depicted in FIG. 84.

After the tubes 482 and 670 are bent to take on the desired curvature, the tool 502 is locked to ensure that the tubes hold this curvature. Tool 502 is so locked by pivoting the lock lever 648 so that the lever pad 662 abuts the handle middle section 510. This results in the rotation of the lever legs 654 so that the lock surfaces 656 press against the distally directed face of lock ring 642. Owing to the shaping of the components forming tool 502, This movement of the lever lock surfaces 656 against the lock ring 642 pushes the lock ring proximally rearward.

The proximal displacement of the lock ring 642 results in the like proximal movement of both steering arm 572 and tensioner 602. The movement of the tensioner simultaneously pulls the sections of both reins 710 that extend forward from the tension to the distal end of the outer tube 670 proximally. The distal ends of these reins 710 it will be recalled are attached to opposed sides of distal collar 770. Thus, this displacement of the reins 710 causes the collars to move proximally against each other. This proximal most shifting collar 740 is understood to press against the adjacent locked in place proximal collar 730. More specifically, the notch-defining side surfaces 750 of each collar 730 and of collar 770 is pressed against the tab-defining side surface 744 of the proximally adjacent collar 740 or of collar 730. This force applied by this collar-against-collar compression inhibits each collar 740 and collar 770 from pivoting relative to the adjacent collar 730 and 740.

As a consequence of the collars 730, 740 and 770 being inhibited from pivoting relative to each other, the collars prevent the further flexing of the tube flexible neck 674. Thus, when the collars are so compressed together the collars inhibit additional bending of the neck 674. The collars once locked, thus substantially reduce the likelihood that when either the neck 674 or tip 698 are subject to side loading that such force will result in the tube 670 from bending away from the curve desired by the practitioner.

Once the outer tube 670 is locked, the practitioner can selectively turn on the actuator 496. This result in the desired actuation of the inner tube in order to perform the desired procedure on the patient. When outer tube tip 698 is pressed against the tissue to perform the procedure, the tip is subjected to side loading. As discussed above, at this time the compression of the collars against each other prevent this side loading from bending out of the curved shaped set by the practitioner.

IV. Alternative Tube Assembly

Figure 85:
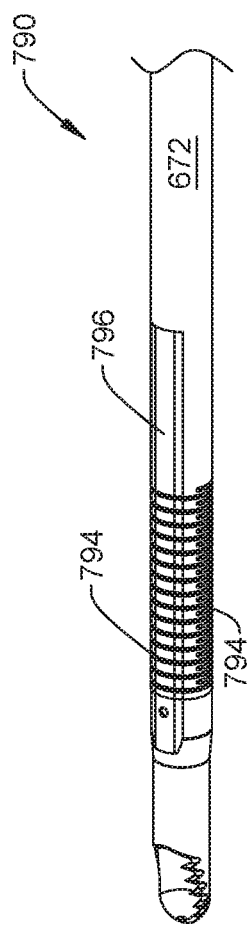
FIG. 85 is a perspective view of an alternative outer tube.
Figure 86:
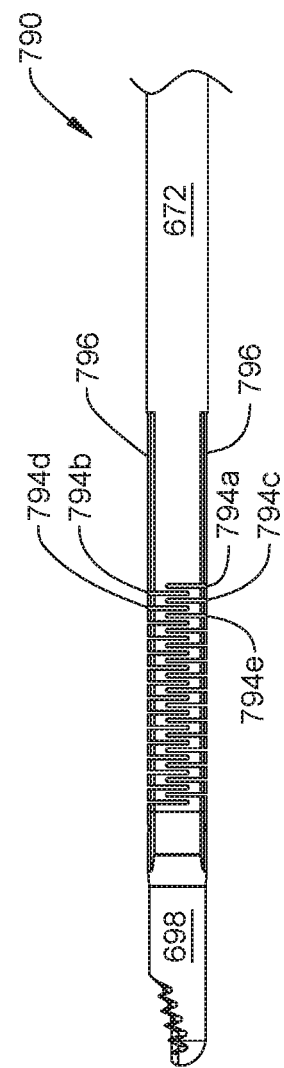
FIG. 86 is a cross sectional view of the outer tube of FIG. 85.
Figure 87:
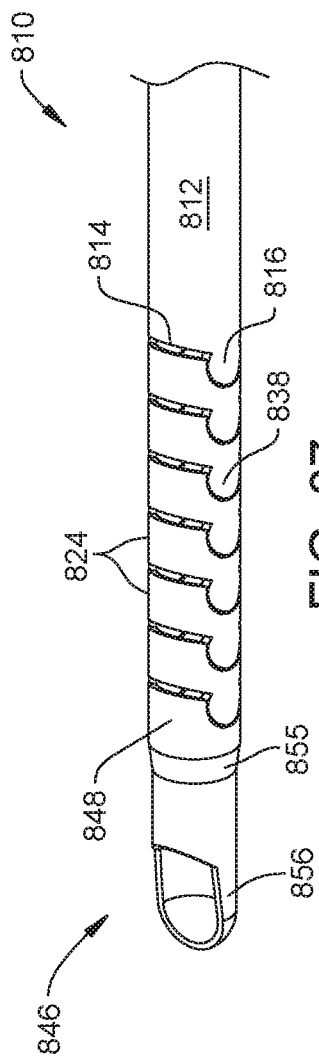
FIG. 87 is a perspective view of an alternative outer shaft or outer tube of this invention.
Figure 88:
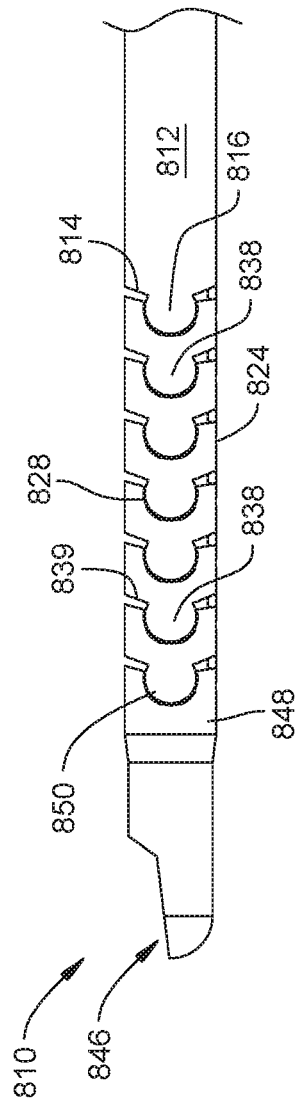
FIG. 88 is a plan view of the side of the outer shaft of FIG. 87.
Figure 89:
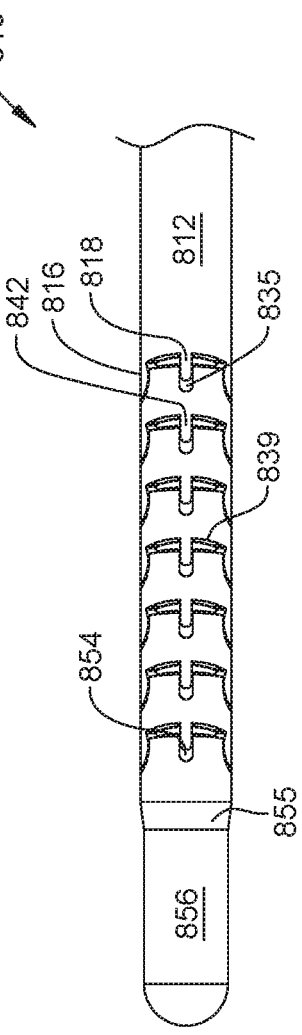
FIG. 89 is a plan view of the underside of the outer shaft of FIG. 87.
Figure 90:
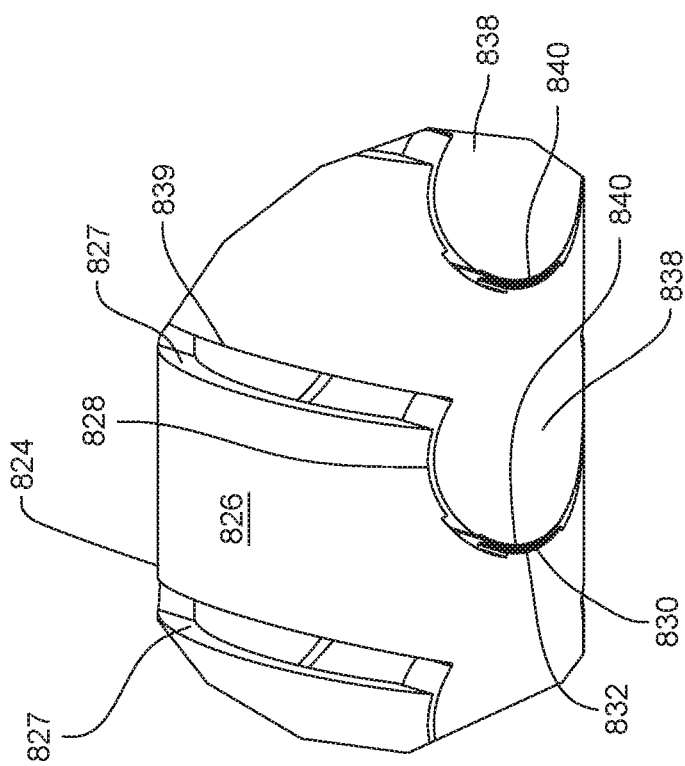
FIG. 90 is an enlarged perspective view of a portion of the shaft of FIG. 87.

FIGS. 85 and 86 illustrate an alternative bendable outer tube 790 of this invention. Outer tube 790 can substitute for tube 670. Outer tube 790 is provided with the previously described tube trunk 672 and tube tip 698.

A flexible neck 792, connects the tip 698 to the trunk 672. Neck 792 is formed to have a number of parallel slots 794. Each slot 794 is located in a plane perpendicular to the proximal-to-distal longitudinal axis through the tube 790. Each slot 794 subtends an angle around the tube 790 of between 190 and 220°. Slots 794 are also interleaved. Here "interleaved" means that a first set, of slots, slots 794a, 794c, 794e in FIG. 86, curve outwardly from a line that extends along the bottom of the tube 790. Slots 794b and 794d are the second set of slots, alternate with slots 794a, 794c and 794e. Slots 794b and 794d curve outwardly from a line that extends along the top of the tube. Slots 794 provide neck 792 with the flexibility that slots 676 provide neck 674.

Tube 790 is further formed to have two opposed gutters 796. Gutters 796 perform the same function as gutters 684 integral with tube 670. The gutters function as voids for receiving reins 710.

V. Second Alternative Tube Assembly

FIGS. 87-90 illustrate another alternative bendable tube assembly 810 of this invention. Tube assembly 810 can substitute for the outer tube 420 and associated components of tool 280. Tube assembly 810 includes an outer tube 812 analogues in basic shape and function to outer tube 420. Plural links 824 extend forward from outer tube 812. A tip 846, analogues to tip 456 is attached to the distal most link 824.

An understanding of the structures of the components forming outer tube assembly 810 starts with the understanding of the structure of a single link 824. Each link 824 includes a tube-like base 826. Base 826 is formed to have a bottom two arcuately spaced apart bottom surfaces 827 one identified in FIG. 90. Each bottom surface 827 has a nadir, not identified, which is the most proximal portion of the bottom surface. Extending away from the opposed sides of the nadir, the opposed sides of the bottom surface 827 curve distally forward. Bottom surfaces 827 are diametrically opposed to each other around the longitudinal proximal-to-distal axis through tube assembly 810. Sockets 828 separate the opposed surfaces. Each socket 828 has a circular shape similar to that of sockets 450. A difference between the two sockets 450 and 828 is that link 824 is formed to have teeth 832 that project into socket 828. Teeth 832 are formed on the surface of an arcuately ridge 830 that extends inwardly from the curved surface of the link base 826 that defines the socket 828. Link 824 is further formed so as to have a slot 835 that extends inwardly from one of the bottom surfaces 827. Slot 835 is similar to previously described slot 452 (FIG. 51).

Two diametrically opposed arms 838 extend forward from link base 826. Arms 838 are generally similar in shape to link arms 436. Arms 436 and 838 are different in that the outer distalmost curved face of each arm 838 is formed with teeth 840. Arm teeth 840 are dimensioned to engage teeth 832 integral with the base of the distally adjacent link 824. The base 826 of each link 824 is further formed to have two distally directed face surfaces 839. The edges of one face surface 839 each is called out in each of FIGS. 88-90. Each face surface 839 is an arcuately shaped surface in that the surface curves from the shoulder associated with one arm to the adjacent shoulder associated with the other arm 838. Each face surface 839 is concave in that as the surface extends away from one arm, the surface curves proximally rearward. The face surface 839 extends has a nadir, not identified, that is in line with the nadir of the underlying bottom surface 827 of the base 826. From this proximally located nadir, the face surface 839 curves distally forward to the shoulder integral with the other arm 838.

A leg 842 analogues to leg 438 extends forward from the base 826 of each link 824. Each leg 842 seats in the complementary slot 835 of the distally adjacent link.

Outer tube 812 is formed to have two diametrically opposed arms 816. Arms 816 are identical in shape to link arms 838. Face surfaces 814 with a shape similar if not identical to that of link face surfaces 839 extend between arms 816. The edges of faces surfaces are called out in FIGS. 87 and 88. The outer tube 812 also has a leg 818 analogues to a link leg 842.

Tip 846 has a base 848, a neck 855 and a head 856 essentially identical to base 458, neck 460 and head 462 of tube tip 456. Not illustrated are features provided to facilitate the securing of steering reins to the tip 846. Base 848 is formed with two sockets 850, one socket identified in FIG. 88. Each socket 850 is identical to a link socket 828. Thus, while not distinctly illustrated teeth project into each socket 850. Tip base 848 also has a slot 854 essentially identical to a link slot 835.

When components forming tube assembly 810 are put together, outer tube arms 816 seat in the sockets 828 of the proximal most link 824. Outer tub leg 818 is seated in slot 835 of the proximal most link 824. The arms 838 and leg 842 of each link 824 are seated in the sockets 828 and slot 835 of the distally located adjacent link. The arms 838 and leg 842 of the distal most link 824 are seated in the sockets 850 and slot 854 formed in the tip 846. Not shown is the means by which the steering reins 468 (FIG. 52) are attached to the tip 846.

Outer tube 812, links 824 and tip 846 function in the same general manner as the previously described tube 420, links 430 and tip 456. As long as both reins are not in tension, each link 824 is able to pivot about the proximally adjacent link. Specifically, the pivot axis of the link is the axial line that extends through the center of the link sockets 828 and the sockets 850 of the tip 846. This pivoting is possible in part because the bottom surface 827 of each link 824 is longitudinally spaced from the adjacent face surface 839 of the proximally adjacent link.

Once the tool with which tube assembly 810 is associated is curved appropriately, the links are locked in position. Links 824 are locked by placing both steering reins in tension. This simultaneous tensioning of the steering reins compresses the links 824 between, at one end outer tube 812, and at the opposed end tip 846. Each arm 816 and 838 abuts the surface of the respective socket 828 and 850 in which the arm is seated. More specifically, the arm teeth engage the teeth that extend into the socket 828 or 850. This meshing of teeth reduces the likelihood that, when exposed to side loading, a link or the tip will pivot relative to the arm 816 or 838 against which the link or tip is pressed.

VI. Third Alternative Tube Assembly

FIGS. 91-94 illustrate another alternative outer tube 870 of this invention. Tube 870 is a second substitute for tube 670. Tube 870 is a single piece tube that has a trunk 872, a flexible neck 876 and a tip 890. Trunk 872 is tube like in shape.

Neck 876 is a helical wrap that extends forward trunk 872. Each 360° turn of the neck 876 is similar but not identical in shape to one of the previously described links 824. Thus, each 360° turn of the neck is shaped to define two sockets 878 and two arms 880. Each socket 878 is similar in to one of the previously described sockets 828. Each arm 880 is similar in shape to one of the previously described arms 838. The neck 876 is formed so that while not illustrated, teeth project into the sockets 878 and the arms 880 are provided with teeth able to mesh with the teeth disposed in the socket. These teeth are understood to be similar in shape to previously described socket teeth 832 and arm teeth 838.

Sockets 878 are disposed in two rows. The plane in which the longitudinal axes of the socket rows are disposed extends through the longitudinal axis that extends proximally-to-distally through tube 870. Arms 880 are disposed in the same rows in which the sockets 878 are aligned. While the socket/arm rows are diametrically opposed from each other relative to the longitudinal axis of the tube 870, owing to the helically shape of the neck each socket/arm pair is spaced longitudinally from the closest opposed socket/arm pair.

Flexible neck 876 is further formed so that between each pair of arcuately adjacent arms 880, there is a gap 882 between the front, distally directed surface of the proximal turn of the neck and the adjacent rear, proximally directed surface of the distally adjacent turn. This gap 882 allows each turn of the neck 876 to flex or pivot relative to the proximally adjacent turn. There is a similar gap 881 between the distal end of trunk 872 and the initial turn of the neck. Gap 881 allows the proximal turn of the neck to flex relative to trunk 872. A like gap 883 exists between the distal end of the neck and the proximal end of tip 890. Gap 883 allows tip to flex relative to the neck. It is understood that these flexures are along axes perpendicular to the coplanar axes around which the slot/arm rows are centered.

The distal end of the helical wrap forming neck 876 terminates at tip 890. Tip 890 has essentially the same features as previously described tip 846. Not identified are the sockets in the tip base in which the distal most arms 880 are seated. Not illustrated are the features of tube 870 that hold the steering reins to the tube tip Flexible neck 876 of tube 870 performs the same function as the previously described links 430 and 824. As long as the steering reins of the tool with which tube 870 is integral are not both in tensions, the individual turns of the neck are able to pivot, flex, relative to each other. Once the flexible neck develops the desired curvature, both reins are tensioned. The tensioning of the reins drives each socket 878 defining surface of the neck against the arm seated in the socket. More particularly, the teeth that project into the socket are driven into engagement, with the adjacent arm teeth. This abutment of the wraps with the arms of the proximally adjacent wraps inhibits further flexing of the neck 876. Thus, when the neck or tip are subjected to side loading, the neck resists being flexed away from the curved shape desired by the practitioner using the tool with which tube 870 is integral.

VII. Alternative Embodiments

The foregoing is directed to specific versions of the invention. Other versions of the inventions may have features different from what has been described.

From the above it should be clear that the features of the different embodiments of the invention can be combined.

Not all versions of the invention may have all the features of the described versions of the invention. Thus, in some tools of this invention may be constructed so that between the shaft and the working member there are two links wherein the distal end of the shaft is shaped to function as a first link and the proximal end of the working member has a features that enable the working member to function as the second link.

Likewise, the invention is not limited to the disclosed steering units for selectively tensioning/slacking the cable (or reins) to cause the desired shaft (or tube) bend. Thus, the invention further encompasses steering units wherein linked but separate drive elements causes the selective cable tensioning and slacking. Further in some versions of the invention, electrically driven components as opposed to manually driven components may be employed to tension/slacking the steering cables. Thus, there is no requirement that in all versions of the invention the member that simultaneously tensions at least one steering cable while slacking at least one other steering cable be rotatably mounted to the handle.

Other assembles different from what has been disclosed may be employed to lock the bendable links in place. For example, not all assemblies that tension the cables to cause the compression of adjacent links function by moving or displacing the steering assembly. In some versions of the invention, selectively moveable tabs move between positions in which the tabs are spaced from and abut the steering cables or reins. When the tabs are spaced from the steering cables, it is possible to tension/slacken the cables in order to bend the shaft. When it is desirable to lock the bend, the tabs are forced against the cables. This places the cables in tension so as to result in the compressing of the links. It is also within the scope of this invention that electrically displaced components, as opposed to a manually actuated components tension the cables to inhibit buckling of the curved shaft. It is likewise within the scope of this invention that to move the steering member between the bending enabled and locked positions the steering member is rotated in the selected position. Thus, this invention is not limited to assemblies that, to so lock the links in position, it is necessary to have the steering assembly undergo a translational movement.

The shape of the components is likewise not limited to what is described above. Thus, in an alternative version of the first embodiment of the invention a pistol like handpiece can substitute for the disclosed handle. In the first and second alternative embodiments of the invention, a handle can substitute for the disclosed pistol like handpiece body.

The means of actuating the tool may not always be a powered actuator. For example, some tools of this invention, even tool 110, may include a manually actuated cable that functions as the actuating unit. This cable is selectively tensioned/slackened to cause the pivoting movement of the jaw of a forceps of a cutting arm of a pair of scissors. A finger grip moveably attached to the handle or handpiece of the tool is moved to cause the selective tensioning/slacking of the cable. Alternatively, this cable may be rotated.

The structure of the link sockets and complementary link protuberances that seat in the sockets are likewise not limited to the disclosed arrangements. For example, it may be desirable to provide the links such that the at least some of the socket-defining surfaces are angled relative to each other. The outer surfaces of the complementary protuberances may have complementary angled surfaces. When the socket-defining surfaces are pressed against the adjacent surfaces of the protuberances, one pair of flat abutting surfaces may be adjacent another pair of flat abutting surfaces such that these two pairs of surfaces are angled relative to each other. A benefit of this arrangement is that it would further inhibit unwanted pivotal movement of one link relative to the other link.

In some versions of the invention, only one of the socket-defining surfaces or the protuberances are provided with teeth. When the links are urged together the teeth embed in the outer of the protuberance or socket-defining surface to inhibit relative rotation of the links.

Links 230, 430, and 824 and neck 876 are described as having per link pair two protuberances and complementary sockets. This should not be interpreted as limiting. In other versions of the invention, each pair of longitudinally adjacent links may be constructed so one link has three or more arms or other protuberances. The adjacent link would have three or more sockets. Each protuberance would seat in its own socket.

Likewise, the invention is not limited to tools wherein when the steering unit is in the neutral position, the working member is axially aligned with the shaft. In some versions of the invention, owing to the design of the links, the dimensions of the steering cables or other design feature, a tool of this invention may be constructed so that when the steering unit is in the neutral position, the working member is centered on an axis that is angled relative to the longitudinal axis of the shaft. Upon the actuation of the steering unit, the cables may be tensioned and slacked to at least one of bend the working member back towards the shaft longitudinal axis or bend the working member is oriented along an axis that is angled further away from the longitudinal axis of the shaft.

Likewise, in some versions of the invention, it may be desirable to provide the steering assembly with three or five or more steering cables.

Further while the invention is described as being useful as a surgical tool, this invention may have other applications. Thus, the bendable tool of this invention Accordingly, it is an object of the appended claims to cover all variations and modifications that come within the true spirit and scope of the invention.

What is claimed is:

1. A surgical tool comprising:
   a handle;
   an outer tube coupled to said handle and defining a longitudinal axis, wherein said outer tube comprises a flexible neck;
   links coupled together so as to be pivotable relative to each other, wherein a proximal one of said links coupled to said outer tube;
   an inner tube rotatably disposed in said outer tube, said inner tube comprising a flexible neck, and a tissue working member capable of manipulating tissue, wherein said flexible neck of said inner tube is aligned with said flexible neck of said outer tube;
   a steering assembly comprising steering cables, and a steering unit coupled to said handle and said steering cables, wherein said steering unit is configured to be actuated to simultaneously tension at least one of said steering cables and slacken at least another one of said steering cables to cause relative pivoting of at least two of said links so as to bend or curve said flexible neck and orient said tissue working member on an axis that is offset from said longitudinal axis; and
   a lock assembly mounted to said handle to move between from a bending enabled position in which said steering cables may be tensioned or slackened with actuation of said steering unit, and a locked position in which simultaneous tension is placed on said steering cables to compress said links against each other and inhibit further pivoting of said links during rotation of said inner tube within said outer tube and against side loading from the tissue,
   wherein said steering cables extend along opposing outer sides of said outer tube, and wherein said links are collars disposed over said flexible neck of said outer tube and further disposed over a distal portion of said steering cables.

2. The surgical tool of claim 1, further comprising a powered actuator coupled to said handle and said inner tube, said powered actuator configured to rotate said inner tube relative to said outer tube.

3. The surgical tool of claim 1, wherein each of said links is shaped to have a frame that is tube-shaped with said frames of said links have the same inner and outer diameters as said outer tube.

4. The surgical tool of claim 1, wherein said tissue working member comprises a first cutout defined within said inner tube, and a second cutout defined within said outer tube and in axial registration with said first cutout, wherein sharp edges of said first or second cutouts are configured to cut the tissue during rotation of said inner tube within said outer tube.

5. The surgical tool of claim 4, wherein each of said links comprise a leg seated within a slot of an adjacent one of said links so to prevent adjacent pairs of said links from moving out of engagement when subjected to the side loading.

6. The surgical tool of claim 1, further comprising a steering bar that is pivotally mounted to said handle and coupled to said cables, said steering bar configured to be pivoted to simultaneously tension at least one of said steering cables and slacken at least another one of said steering cables.

7. The surgical tool of claim 1, further comprising a steering wheel mounted within a void space of said handle and coupled to said steering handles, said steering wheel configured to be rotated in one of two directions to simultaneously tension at least one of said steering cables and slacken at least another one of said steering cables.

8. The surgical tool of claim 1, wherein said tissue working member is a mechanical cutting device.

9. A surgical tool comprising:
   a handle formed with a bore extending distally forward from a proximal end of said handle;
   an outer tube coupled to said handle and defining a longitudinal axis, wherein said outer tube comprises a tube trunk, a flexible neck, and a tube tip, and wherein said outer tube further defines tube gutters extending longitudinally along an outer surface of said outer tube and across said flexible neck;

links coupled together so as to be pivotable relative to each other, wherein a proximal one of said links coupled to said outer tube;

an inner member disposed in said outer tube and comprising a tissue working member capable of manipulating tissue;

a steering assembly comprising steering cables, and a steering unit coupled to said handle and said steering cables, wherein said steering unit is configured to be actuated to simultaneously tension at least one of said steering cables and slacken at least another one of said steering cables to cause relative pivoting of at least two of said links so as to bend or curve said inner member and orient said tissue working member on an axis that is offset from said longitudinal axis; and a lock assembly mounted to said handle to move between from a bending enabled position in which said steering cables may be tensioned or slackened with actuation of said steering unit, and a locked position in which simultaneous tension is placed on said steering cables to compress said links against each other and inhibit further pivoting of said links against side loading from the tissue, wherein each of said steering cables is disposed in a respective one of said tube gutters, and wherein said links are disposed over said flexible neck of said outer tube.

10. The surgical tool of claim 9, wherein said tissue working member comprises one of an electrode, an ultrasonic vibration, mechanical cutting devices, boring devices, and devices that emit photonic energy.

11. The surgical tool of claim 9, wherein said inner member is rotatably disposed within said outer tube.

12. The surgical tool of claim 11, further comprising an actuator, wherein said actuator is a powered actuator coupled to said handle and said inner member, said powered actuator being configured to rotate said inner member relative to said outer tube.

13. The surgical tool of claim 9, wherein each of said links is shaped to have a frame that is tube-shaped with said frames of said links have the same inner and outer diameters as said outer tube.

14. The surgical tool of claim 9, wherein said links are shaped such that said outer tube is selectively curvable in a single direction relative to said longitudinal axis.

15. A surgical tool comprising:
a handle;
a shaft coupled to said handle and defining a longitudinal axis, said shaft comprising an outer tube, and an inner tube rotatably disposed in said outer tube and comprising a cutting feature capable of cutting tissue, wherein each of said outer tube and said inner tube comprise a region configured to bend or curve;

a powered actuator coupled to said handle and said inner tube, said powered actuator configured to rotate said inner tube relative to said outer tube;

a steering assembly comprising steering cables, and a steering unit coupled to said handle and said steering cables, wherein said steering unit is configured to be actuated to simultaneously tension at least one of said steering cables and slacken at least another one of said steering cables so as to bend or curve said regions to orient said cutting feature on an axis that is offset from said longitudinal axis; and a lock assembly mounted to said handle to move between from a bending enabled position in which said steering cables may be tensioned or slackened with actuation of said steering unit, and a locked position in which simultaneous tension is placed on said steering cables to inhibit further bending or curving of said regions during rotation of said inner tube within said outer tube, wherein said outer tube further defines tube gutters extending longitudinally along an outer surface of said outer tube and across said region, and wherein said wherein each of said steering cables is disposed in a respective one of said tube gutters.

16. The surgical tool of claim 15, wherein said inner tube comprises a tip comprising said cutting feature, and wherein said region of said inner tube is a flexible neck configured to be aligned with said region of said outer tube.

17. The surgical tool of claim 15, wherein said region of said outer tube comprises links coupled together so as to be pivotable relative to each other, and wherein said links are collars disposed over a distal portion of said steering cables.

18. The surgical tool of claim 17, wherein each of said links is shaped to have a frame that is tube-shaped with said frames of said links have the same inner and outer diameters as said outer tube.

19. The surgical tool of claim 15, wherein said shaft is selectively curvable in a single direction relative to said longitudinal axis.

20. The surgical tool of claim 16, wherein said flexible neck comprises a helical slot with interlocking teeth.

* * * * *